US008987258B2

(12) United States Patent
Oalmann et al.

(10) Patent No.: US 8,987,258 B2
(45) Date of Patent: Mar. 24, 2015

(54) CHROMENONE ANALOGS AS SIRTUIN MODULATORS

(76) Inventors: Christopher Oalmann, Watertown, MA (US); Robert B. Perni, Marlborough, MA (US); Chi B. Vu, Arlington, MA (US)

( * ) Notice: Subject to any disclaimer, the term of this patent is extended or adjusted under 35 U.S.C. 154(b) by 433 days.

(21) Appl. No.: 13/121,410

(22) PCT Filed: Sep. 29, 2009

(86) PCT No.: PCT/US2009/058862
§ 371 (c)(1),
(2), (4) Date: Jun. 22, 2011

(87) PCT Pub. No.: WO2010/037127
PCT Pub. Date: Apr. 1, 2010

(65) Prior Publication Data
US 2011/0257174 A1    Oct. 20, 2011

Related U.S. Application Data

(60) Provisional application No. 61/194,576, filed on Sep. 29, 2008.

(51) Int. Cl.
| C07D 417/12 | (2006.01) |
| C07D 417/14 | (2006.01) |
| C07D 405/12 | (2006.01) |
| C07D 405/14 | (2006.01) |
| A61K 31/5377 | (2006.01) |
| A61K 31/427 | (2006.01) |
| A61K 31/4439 | (2006.01) |
| A61K 31/4025 | (2006.01) |
| A61K 31/497 | (2006.01) |
| A61K 31/353 | (2006.01) |
| A61K 45/06 | (2006.01) |
| C07D 311/30 | (2006.01) |
| A61P 3/00 | (2006.01) |
| A61P 3/10 | (2006.01) |

(52) U.S. Cl.
CPC ............ *C07D 417/12* (2013.01); *A61K 31/353* (2013.01); *A61K 45/06* (2013.01); *C07D 311/30* (2013.01); *C07D 405/12* (2013.01); *C07D 417/14* (2013.01); *C07D 405/14* (2013.01)
USPC ........ 514/233.5; 514/365; 514/337; 514/422; 514/255.05; 548/200; 548/525; 546/269.7; 546/283.1; 546/276.4; 544/405; 544/131; 544/133; 544/120

(58) Field of Classification Search
USPC ................. 514/255.05, 241, 371; 544/405; 546/114
See application file for complete search history.

(56) References Cited

U.S. PATENT DOCUMENTS

| 4,525,356 A | 6/1985 | Itho et al. ........................ 514/234 |
| 4,594,345 A | 6/1986 | Enomoto et al. ............. 514/234 |
| 4,904,690 A | 2/1990 | Aono et al. .................... 514/456 |
| 4,939,141 A | 7/1990 | Toda et al. .................. 514/230.5 |
| 5,116,954 A | 5/1992 | Briet et al. ...................... 534/551 |
| 5,703,075 A * | 12/1997 | Gammill et al. ............ 514/233.5 |
| 6,187,779 B1 | 2/2001 | Pamukcu et al. .............. 514/259 |
| 7,345,178 B2 | 3/2008 | Nunes et al. .................. 548/154 |
| 7,829,556 B2 | 11/2010 | Bemis et al. ............... 514/233.2 |
| 7,855,289 B2 | 12/2010 | Nunes et al. .................. 544/235 |
| 7,893,086 B2 | 2/2011 | Bemis et al. .................. 514/301 |
| 8,088,928 B2 | 1/2012 | Nunes et al. .................. 548/218 |
| 8,093,401 B2 | 1/2012 | Nunes et al. ............... 548/309.7 |
| 2009/0163545 A1 | 6/2009 | Goldfarb ........................ 514/183 |
| 2011/0046110 A1 | 2/2011 | Vu et al. ......................... 544/106 |

(Continued)

FOREIGN PATENT DOCUMENTS

| DE | 1 108 698 | 6/1961 |
| EP | 0341104 B1 | 4/1989 |

(Continued)

OTHER PUBLICATIONS

Lakshmi et al. Current Science 1972, 41(18), 680-1.*
Stahura et al. "Molecular Scaffold-Based Design and Comparison of Combinatorial Libraries Focused on the ATP-Binding Site of Protein Kinases," *Journal of Molecular Graphics and Modelling*, 17(1) 1-9 and 51-52 (1999).
International Preliminary Report on Patentability dated Mar. 29, 2011, CAS registry No. RN 101949-99-9.

(Continued)

*Primary Examiner* — Joseph Kosack
*Assistant Examiner* — Amanda L Aguirre
(74) *Attorney, Agent, or Firm* — Grace C. Hsu; John Lemanowicz

(57) ABSTRACT

The present invention relates to novel chromenone analog sirtuin modulator compounds of Formula (I):

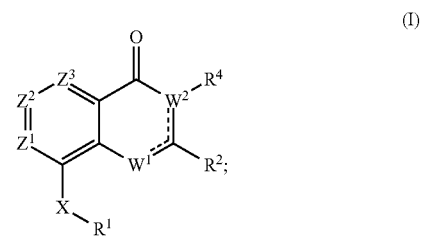

or
pharmaceutically acceptable salts thereof, corresponding pharmaceutical compositions and treatment methods and combination therapies thereof for use in increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

4 Claims, No Drawings

(56) References Cited

U.S. PATENT DOCUMENTS

| | | | |
|---|---|---|---|
| 2011/0077248 A1 | 3/2011 | Vu et al. | 544/106 |
| 2011/0124637 A1 | 5/2011 | Vu et al. | 544/106 |
| 2011/0263564 A1 | 10/2011 | Narayan et al. | 514/252.1 |
| 2011/0306612 A1 | 12/2011 | Vu et al. | 544/106 |
| 2011/0319411 A1 | 12/2011 | Vu et al. | 544/106 |
| 2012/0108585 A1 | 5/2012 | Vu et al. | 544/106 |

FOREIGN PATENT DOCUMENTS

| | | | |
|---|---|---|---|
| JP | 60246384 A | 12/1985 | |
| WO | WO 90/06921 | 6/1990 | |
| WO | WO 94/01408 | 1/1994 | |
| WO | WO 95/32199 | 11/1995 | |
| WO | WO 01/53266 | 7/2001 | |
| WO | WO 2004/016607 | 2/2004 | |
| WO | WO 2005/105764 | 11/2005 | |
| WO | WO 2006/035967 | 4/2006 | |
| WO | WO 2006/035967 A1 * | 4/2006 | C07D 213/75 |
| WO | WO 2006/094210 | 9/2006 | |
| WO | WO 2006/094233 | 9/2006 | |
| WO | WO 2006/094236 A1 | 9/2006 | |
| WO | WO 2006/094239 | 9/2006 | |
| WO | WO 2006/094246 | 9/2006 | |
| WO | WO 2006/094248 | 9/2006 | |
| WO | WO 2006/105403 | 10/2006 | |
| WO | WO 2006/105440 | 10/2006 | |
| WO | WO 2006/127987 | 11/2006 | |
| WO | WO 2007/008548 | 1/2007 | |
| WO | WO 2007/019344 A | 2/2007 | |
| WO | WO 2007/019345 A1 | 2/2007 | |
| WO | WO 2007/019416 A1 | 2/2007 | |
| WO | WO 2007/019417 A1 | 2/2007 | |
| WO | WO 2007/064902 | 6/2007 | |
| WO | WO 2007/102861 | 9/2007 | |
| WO | WO 2008/011476 | 1/2008 | |
| WO | WO 2008/027379 | 3/2008 | |
| WO | WO 2008/060400 | 5/2008 | |
| WO | WO 2008/073451 A2 | 6/2008 | |
| WO | WO 2008/100376 | 8/2008 | |
| WO | WO 2008/100423 | 8/2008 | |
| WO | WO 2008/115518 | 9/2008 | |
| WO | WO2008/156866 A1 | 12/2008 | |
| WO | WO 2008/156869 A2 | 12/2008 | |
| WO | WO 2009/058348 A1 | 5/2009 | |
| WO | WO 2009/061453 | 5/2009 | |
| WO | WO 2009/146358 | 5/2009 | |
| WO | WO 2009/085226 | 7/2009 | |
| WO | WO 2009/089011 | 7/2009 | |
| WO | WO 2009/134973 | 11/2009 | |
| WO | WO 2009/140562 | 11/2009 | |
| WO | WO 2010/003048 | 1/2010 | |
| WO | WO 2010/019606 | 2/2010 | |
| WO | WO 2010/037127 A1 | 4/2010 | |
| WO | WO 2010/037129 | 4/2010 | |
| WO | WO 2010/056549 | 5/2010 | |
| WO | WO 2010/071853 A1 | 6/2010 | |
| WO | WO 2010/077686 | 7/2010 | |
| WO | WO 2010/077947 | 7/2010 | |
| WO | WO 2010/088574 | 8/2010 | |
| WO | WO 2010/101949 | 9/2010 | |
| WO | WO 2011/059839 | 5/2011 | |
| WO | WO 2011/116176 | 9/2011 | |

OTHER PUBLICATIONS

CAS registry No. RN 174765-28-7, Entered STN: Apr. 4, 1996.
Database Caplus[Online] Chemical Abstracts Service, Columbus, Ohio, US; 1986, Database accession No. 1986:626356 ; & JP 60 246384 A (Hokuriku Pharmaceutical) Dec. 6, 1985. CAS registry Nos. 101949-97-7, 101949-98-8 and 101950-00-9.
Extended European Search Report dated Apr. 19, 2012, Application No. EP 09 81 7054.
Extended European Search Report dated Apr. 27, 2012, Application No. EP 09 81 7056.
Knight et al., "A Pharmacological Map of the PI3-K Family Defines a Role for p11[alpha] in Insulin Signaling," Cell, 125:733-747 (2005).
Milne, J. C. & Denu, J. M. The Sirtuin family: therapeutic targets to treat diseases of aging, Current Opinion in Chemical Biology, 12:11-17 (2008).
Porcu et al., "The emerging therapeutic potential of sirtuin-interacting drugs: from cell death to lifespan extension," Trends in Pharmacological Sciences, 26(2):94-103 (2005).
Baur, et al. Nature Reviews Drug Discovery, 11: 443-461 (2012).
Beher, et al. Chem. Biol. Drug Des., 74: 619-624 (2009).
Bemis, et al. Bioorg. & Med. Chem. Letters, 19: 2350-2353 (2009).
Blander, et al. J. Biol. Chem., 280(11): 9780-9785 (2005).
Blum, et al. J. Med. Chem., 54: 417-432 (2011).
Borra, et al. J. Biol. Chem., 280(17): 17187-17195 (2005).
Buchen, et al. Nature (2010). http://www.nature.com/news/2010/100119/full/news.2010.18.html.
Buck, et al. J. Leukocyte Biol., 75: 939-950 (2004).
Bundgaard. Design and application of prodrugs, Textbook of Drug Design and Development, pp. 113-191 (1991).
Burnett, et al. Nature, 477: 482-486 (2011).
Canto, et al. Nature, 477: 411 (2011).
ClinicalTrials.gov—Search of SRT2104—List results. http://clinicaltrials.gov/ct2/results?term=SRT2104 (retrieved on May 24, 2012).
ClinicalTrials.gov—Search of SRT2379—List results. http://clinicaltrials.gov/ct2/results?term=SRT2379 (retrieved on May 27, 2012).
ClinicalTrials.gov—Search of SRT3025—List results. http://clinicaltrials.gov/ct2/results?term=SRT3025 (retrieved on May 27, 2012).
Couzin-Frankel. Science, 334: 1194-1198 (2011).
Csiszar, et al. Am. J. Physiol. Heart Circ. Physiol., 294: H2721-H2735 (2008).
Dai, et al. J. Biol. Chem., 285(43): 32695-32703 (2010).
Dittenhafer-Reed, et al. ChemBioChem., 12: 281-289 (2011).
Feige, et al. Cell Metab., 8: 347-358 (2008).
Hoffman, et al, "Pharmacokinetics and Tolerability of SRT2104, a First-In-Class Small Molecule Activator of SIRT1, after Single and Repeated Oral Administraion in Man," Br J Clin Pharmacol, Electronic publication ahead of print, May 23, 2012, http://www.ncbi.nlm.nih.gov/pubmed/22616762.
Howitz, et al. Nature, 425: 191-196 (2003).
Huber, et al. Future Med. Chem. 2(12): 1751-1759 (2010).
Kaeberlein, et al. J. Biol. Chem., 280(17): 17038-17045 (2005).
Kaeberlein, et al. Aging Cell, 6: 415-416 (2007).
Keystone Symposia on Molecular and Cellular Biology "Sirtuins in Metabolism, Aging and Disease", Feb. 12-16, 2012.
Kubinyi. "3D QSAR in Drug Design Ligand-Protein Internations and Molecular Similarity", Springer, 800 pages, vol. 2-3: 243-244 provided (1998).
Ledford. Nature, 464: 480-481 (2010).
Lombard, et al. Nature, 477: 410 (2011).
Milne, et al. Nature, 450: 712-716 (2007).
Minor, et al. Scientific Reports, 1-48 (2011).
Pacholec, et al. J. Biol. Chem., 285(11): 8340-8351, Mar. 12, 2010.
Pacholec, et al. JBC Papers in Press, Manuscript M1 09.088682, Jan. 8, 2010.
Pacholec, et al. FASEB Summer Research Conferences; NAD Metabolism and Signaling, Jun. 21-26, 2009.
Papers of the Week. "A Resveratrol Reversal", DOI 10.1074/jbc.P109.088682. Mar. 10, 2010 (Abst).
Park, et al. Cell, 148: 421-433 (2012).
Park, et al. Toxicology Letters, 120: 281-291 (2001).
Pfister, et al. PLOS One, 3(12): 1-8 (2008).
Silverman. "The Organic Chemistry of Drug Design and Drug Action," Elsevier, 29-32 (2004).
Stünkel, et al., J. of Biomolecular Screening, 16(10): 1153-1169 (2011).
Terfloth, et al. "Electronic Screening: Lead Finding From Database Mining," Wermuth, The Practice of Med. Chem., 2nd Ed. Chapters 9-10, pp. 131-157 (2003).
Timmers, et al. Cell Metabolism, 14: 612-622 (2011).

(56) References Cited

OTHER PUBLICATIONS

Viswanathan & Guarente. *Nature*, 477: E1-E2 (2011).
Venkatasubramanian, et al., "Cardiovascular Effects of a Novel SIRT 1 Activator, SRT2104, in Otherwise Healthy Cigarette Smokers", Abstract for AHA 2012 Meeting.
Yamazaki, et al. *Am. J. Physiol. Endocrinol. Metab.*, 297: E1179-E1186 (2009).
Yamori, et al. *Drug Delivery System*, 18(4): 385-393 (2003). Abstract only.
Yoshizaki, et al. Am. J. Physiol. Endocrinol. Metab., 298: E419-E428 (2010).
Yoshizaki, et al. Molecular *and Cellular Biology*, 29(5): 1363-1374 (2009).
Zarse, et al. *Horm. Metab. Res.*, 42(12): 837-839 (2010).

\* cited by examiner

CHROMENONE ANALOGS AS SIRTUIN MODULATORS

REFERENCE TO RELATED APPLICATION

This application is a national stage filing under 35 U.S.C. 371 of International Application No. PCT/US2009/058862, filed Sep. 29, 2009, which claims the benefit of U.S. Provisional Application No. 61/194,576, filed Sep. 29, 2008, the disclosures of which are incorporated herein by reference thereto. International Application No. PCT/US2009/058862 was published under PCT Article 21(2) in English.

BACKGROUND

The Silent Information Regulator (SIR) family of genes represents a highly conserved group of genes present in the genomes of organisms ranging from archaebacteria to eukaryotes. The encoded SIR proteins are involved in diverse processes from regulation of gene silencing to DNA repair. The proteins encoded by members of the SIR gene family show high sequence conservation in a 250 amino acid core domain. A well-characterized gene in this family is *S. cerevisiae* SIR2, which is involved in silencing HM loci that contain information specifying yeast mating type, telomere position effects and cell aging. The yeast Sir2 protein belongs to a family of histone deacetylases. The Sir2 homolog, CobB, in *Salmonella typhimurium*, functions as an NAD (nicotinamide adenine dinucleotide)-dependent ADP-ribosyl transferase.

The Sir2 protein is a class III deacetylase which uses NAD as a cosubstrate. Unlike other deacetylases, many of which are involved in gene silencing, Sir2 is insensitive to class I and II histone deacetylase inhibitors like trichostatin A (TSA).

Deacetylation of acetyl-lysine by Sir2 is tightly coupled to NAD hydrolysis, producing nicotinamide and a novel acetyl-ADP ribose compound. The NAD-dependent deacetylase activity of Sir2 is essential for its functions which can connect its biological role with cellular metabolism in yeast. Mammalian Sir2 homologs have NAD-dependent histone deacetylase activity.

Biochemical studies have shown that Sir2 can readily deacetylate the amino-terminal tails of histones H3 and H4, resulting in the formation of 1-O-acetyl-ADP-ribose and nicotinamide. Strains with additional copies of SIR2 display increased rDNA silencing and a 30% longer life span. It has recently been shown that additional copies of the *C. elegans* SIR2 homolog, sir-2.1, and the *D. melanogaster* dSir2 gene greatly extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

In humans, there are seven Sir2-like genes (SIRT1-SIRT7) that share the conserved catalytic domain of Sir2. SIRT1 is a nuclear protein with the highest degree of sequence similarity to Sir2. SIRT1 regulates multiple cellular targets by deacetylation including the tumor suppressor p53, the cellular signaling factor NF-κB, and the FOXO transcription factor.

SIRT3 is a homolog of SIRT1 that is conserved in prokaryotes and eukaryotes. The SIRT3 protein is targeted to the mitochondrial cristae by a unique domain located at the N-terminus. SIRT3 has NAD+-dependent protein deacetylase activity and is ubiquitously expressed, particularly in metabolically active tissues. Upon transfer to the mitochondria, SIRT3 is believed to be cleaved into a smaller, active form by a mitochondrial matrix processing peptidase (MPP).

Caloric restriction has been known for over 70 years to improve the health and extend the lifespan of mammals. Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of a restricted calorie diet. Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway.

SUMMARY

Provided herein are novel sirtuin-modulating compounds and methods of use thereof.

In one aspect, the invention provides sirtuin-modulating compounds of Structural Formulas (I) to (IV) as are described in detail below.

In another aspect, the invention provides methods for using sirtuin-modulating compounds, or compositions comprising sirtuin-modulating compounds. In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, chemotherapeutic induced neuropathy, neuropathy associated with an ischemic event, ocular diseases and/or disorders, cardiovascular disease, blood clotting disorders, inflammation, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods comprise administering to a subject in need thereof a pharmaceutically effective amount of a sirtuin-modulating compound.

In certain aspects, the sirtuin-modulating compounds may be administered alone or in combination with other compounds, including other sirtuin-modulating compounds, or other therapeutic agents.

DETAILED DESCRIPTION

1. Definitions

As used herein, the following terms and phrases shall have the meanings set forth below. Unless defined otherwise, all technical and scientific terms used herein have the same meaning as commonly understood to one of ordinary skill in the art.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The term "bioavailable" when referring to a compound is art-recognized and refers to a form of a compound that allows for it, or a portion of the amount of compound administered, to be absorbed by, incorporated into, or otherwise physiologically available to a subject or patient to whom it is administered.

"Biologically active portion of a sirtuin" refers to a portion of a sirtuin protein having a biological activity, such as the ability to deacetylate. Biologically active portions of a sirtuin may comprise the core domain of sirtuins. Biologically active portions of SIRT1 having GenBank Accession No. NP_036370 that encompass the NAD+ binding domain and the substrate binding domain, for example, may include without limitation, amino acids 62-293 of GenBank Accession No. NP_036370, which are encoded by nucleotides 237 to 932 of GenBank Accession No. NM_012238. Therefore, this region is sometimes referred to as the core domain. Other biologically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238.

The term "companion animals" refers to cats and dogs. As used herein, the term "dog(s)" denotes any member of the species *Canis familiaris*, of which there are a large number of different breeds. The term "cat(s)" refers to a feline animal including domestic cats and other members of the family Felidae, genus *Felis*.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "$ED_{50}$" refers to the art-recognized measure of effective dose. In certain embodiments, $ED_{50}$ means the dose of a drug which produces 50% of its maximum response or effect, or alternatively, the dose which produces a pre-determined response in 50% of test subjects or preparations. The term "$LD_{50}$" refers to the art-recognized measure of lethal dose. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and bone loss, e.g. osteoporosis in particular.

The term "livestock animals" refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*.

The term "mammal" is known in the art, and exemplary mammals include humans, primates, livestock animals (including bovines, porcines, etc.), companion animals (e.g., canines, felines, etc.) and rodents (e.g., mice and rats).

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 10%, 20%, 30%, 40%, 50%, 60% or between 20% and 70%, 30% and 60%, 40% and 60% or more using methods described herein.

"Sirtuin-activating compound" refers to a compound that increases the level of a sirtuin protein and/or increases at least one activity of a sirtuin protein. In an exemplary embodiment, a sirtuin-activating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin protein" refers to a member of the sirtuin deacetylase protein family, or preferably to the sir2 family, which include yeast Sir2 (GenBank Accession No. P53685), *C. elegans* Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

"SIRT1 protein" refers to a member of the sir2 family of sirtuin deacetylases. In one embodiment, a SIRT1 protein includes yeast Sir2 (GenBank Accession No. P53685), *C. elegans* Sir-2.1 (GenBank Accession No. NP_501912), human SIRT1 (GenBank Accession No. NM_012238 or NP_036370 (or AF083106)), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT 5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In one embodiment, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In one embodiment, a SIRT3 protein includes a fragment of SIRT3 protein that is produced by cleavage with a mitochondrial matrix processing peptidase (MPP) and/or a mitochondrial intermediate peptidase (MIP).

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

2. Sirtuin Modulators

In one aspect, the invention provides novel sirtuin-modulating compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. Other compounds disclosed herein may be suitable for use in a pharmaceutical composition and/or one or more methods disclosed herein.

In one embodiment, sirtuin-modulating compounds of the invention are represented by Structural Formula (I):

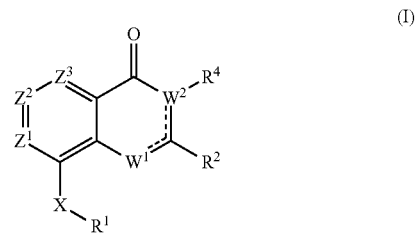

or a salt thereof, wherein:
  each of $Z^1$, $Z^2$, and $Z^3$, is independently selected from N and CR, wherein: no more than one of $Z^1$, $Z^2$ and $Z^3$ is N; and
  R is selected from hydrogen, halo, —OH, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —O—($C_1$-$C_4$) alkyl, —S—($C_1$-$C_4$) alkyl and $C_3$-$C_7$ cycloalkyl;
  ---- represents an optional bond,
  $W^1$ is selected from —O—, —NH— or —N═, such that when $W^1$ is —N═, $W^1$ is bound to $C(R^2)$ through a double bond,
  $W^2$ is —$CR^4$═ when $W^1$ is —NH— or —O—, such that when $W^2$ is —$CR^4$═, $W^2$ is bound to $C(R^2)$ through a double bond; and $W^2$ is —$NR^4$— when $W^1$ is —N═;
  $R^1$ is selected from a carbocycle and a heterocycle, wherein $R^1$ is optionally substituted with one to two substitutents independently selected from halo, —C≡N, $C_1$-$C_4$ alkyl, ═O, $C_3$-$C_7$ cycloalkyl, fluoro-substituted $C_1$-$C_4$ alkyl, —O—$R^3$, —S—$R^3$, —($C_1$-$C_4$ alkyl)-$N(R^3)(R^3)$, —$N(R^3)$ $(R^3)$, —O—($C_1$-$C_4$alkyl)-$N(R^3)(R^3)$, —($C_1$-$C_4$ alkyl)-O—($C_1$-$C_4$ alkyl)-$N(R^3)(R^3)$, —C(O)—$N(R^3)(R^3)$, and —($C_1$-$C_4$ alkyl)-C(O)—$N(R^3)(R^3)$, and when $R^1$ is phenyl, $R^1$ is also optionally substituted with 3,4-methylenedioxy, fluoro-substituted 3,4-methylenedioxy, 3,4-ethylenedioxy, or fluoro-substituted 3,4-ethylenedioxy, wherein
    each $R^3$ is independently selected from hydrogen and —$C_1$-$C_4$ alkyl; or
    two $R^3$ are taken together with the nitrogen atom to which they are bound to form a 4- to 8-membered saturated heterocycle optionally comprising one additional heteroatomic unit selected from NH, S, S(═O), S(═O)$_2$, and O, wherein the alkyl is optionally substituted with one or more —OH, fluoro, —$NH_2$, —$NH(C_1$-$C_4$ alkyl), —$N(C_1$-$C_4$ alkyl)$_2$, —$NH(CH_2CH_2OCH_3)$, or —$N(CH_2CH_2OCH_3)_2$ and the saturated heterocycle is optionally substituted at a carbon atom with —OH, —C$_1$-C$_4$ alkyl, fluoro, —NH$_2$, —NH(C$_1$-C$_4$ alkyl), —N(C$_1$-C$_4$ alkyl)$_2$, —NH(CH$_2$CH$_2$OCH$_3$), or —N(CH$_2$CH$_2$OCH$_3$)$_2$;

R$^2$ is selected from a carbocycle and a heterocycle, wherein R$^2$ is optionally substituted with one to two substitutents independently selected from halo, —C≡N, C$_1$-C$_4$ alkyl, C$_3$-C$_7$ cycloalkyl, C$_1$-C$_2$ fluoro-substituted alkyl, —O—R$^3$, —S—R$^3$, —(C$_1$-C$_4$ alkyl)-N(R$^3$)(R$^3$), —N(R$^3$)(R$^3$), —O—(C$_1$-C$_4$ alkyl)-N(R$^3$)(R$^3$), —(C$_1$-C$_4$ alkyl)-O—(C$_1$-C$_4$ alkyl)-N(R$^3$)(R$^3$), —C(O)—N(R$^3$)(R$^3$), —(C$_1$-C$_4$ alkyl)-C(O)—N(R$^3$)(R$^3$), —O-phenyl, phenyl, and a second heterocycle, and when R$^2$ is phenyl, R$^2$ may also be optionally substituted with 3,4-methylenedioxy, fluoro-substituted 3,4-methylenedioxy, 3,4-ethylenedioxy, or fluoro-substituted 3,4-ethylenedioxy, wherein any phenyl or second heterocycle substituent of R$^2$ is optionally substituted with halo; —C≡N; C$_1$-C$_4$ alkyl, fluoro-substituted C$_1$-C$_2$ alkyl, —O—(C$_1$-C$_2$) fluoro-substituted alkyl, —O—(C$_1$-C$_4$) alkyl, —S—(C$_1$-C$_4$) alkyl, —S—(C$_1$-C$_2$) fluoro-substituted alkyl, —NH—(C$_1$-C$_4$) alkyl and —N—(C$_1$-C$_4$)$_2$ alkyl;

R$^4$ is selected from hydrogen, C$_1$-C$_4$ alkyl, C$_1$-C$_4$ fluoro-substituted alkyl, C$_1$-C$_4$ alkyl-N(R$^7$)(R$^7$), C$_1$-C$_4$ alkyl-C(O)—N(R$^7$)(R$^7$), C$_1$-C$_4$ alkyl-O—R$^7$, and C$_1$-C$_4$ alkyl-NR$^7$—C(O)R$^7$, wherein each R$^7$ is independently selected from hydrogen and C$_1$-C$_4$ alkyl;

X is selected from —NH—C(═O)-†, —C(═O)—NH-†, —NH—C(═S)-†, —C(═S)—NH-†, —NH—S(═O)-†, —S(═O)—NH-†, —S(═O)$_2$—NH-†, —NH—S(═O)$_2$-†, —NH—S(O)$_2$—NR$^5$-†, —NR$^5$—S(O)$_2$—NH-†, —NH—C(═O)O-†, —OC(═O)NH-†, —NH—C(═O)NR$^5$-†, —NR$^5$—C(═O)NH-†, —NH—NR$^5$-†, —NR$^5$—NH-†, —O—NH-†, —NH—O-†, —NH—CR$^5$R$^6$-†, —CR$^5$R$^6$—NH-†, —NH—C(═NR$^5$)-†, —C(═NR$^5$)—NH-†, —C(═O)—NH—CR$^5$R$^6$-†, —CR$^5$R$^6$—NH—C(O)-†, —NH—C(═S)—CR$^5$R$^6$-†, —CR$^5$R$^6$—C(═S)—NH-†, —NH—S(O)—CR$^5$R$^6$-†, —CR$^5$R$^6$—S(O)—NH-†, —NH—S(O)$_2$—CR$^5$R$^6$-†, —CR$^5$R$^6$—S(O)$_2$—NH-†, —NH—C(═O)—O—CR$^5$R$^6$-†, —CR$^5$R$^6$—O—C(═O)—NH-†, —NH—C(═O)—NR$^5$—CR$^5$R$^6$-†, and —CR$^5$R$^6$—NH—C(═O)—O-†, wherein:

† represents where X is bound to R$^1$; and each R$^5$ and R$^6$ is independently selected from hydrogen, C$_1$-C$_4$ alkyl, —CF$_3$ and (C$_1$-C$_3$ alkyl)-CF$_3$.

In certain embodiments, compounds of Structural Formula (I) are characterized by one or more of the following characteristics:

when each of Z$^1$, Z$^2$ and Z$^3$ is CR; W$^1$ is —O—, W$^2$ is —C═, R$^4$ is H; and X is —NH—CR$^5$R$^6$-\ or —CR$^5$R$^6$—NH-†, then R$^2$ is other than optionally substituted pyridin-4-yl or unsubstituted morpholin-4-yl;

when each of Z$^1$, Z$^2$ and Z$^3$ is CH; W$^1$ is —O—; W$^2$ is —C═; R$^4$ is H or C$_1$-C$_4$ alkyl; R$^2$ is phenyl; and X is —C(═O)—NH-†, then R$^1$ is other than 1H-benzimidazol-2-yl, 2,3-dihydro-2-oxo-1H-benzimidazol-5-yl, 4-methylpiperazin-1-yl, 6-(morpholin-4-yl)-pyridin-3-yl, 5-(morpholin-4-yl)isoquinolin-8-yl, 5-chloro-2-(4-methyl-1-piperazinyl)phenyl, 7-fluoro-3,4-dihydro-4-oxo-6-quinazolinyl, 1-methyl-1H-pyrazol-3-yl, 1H-pyrazol-3-yl, tetrazol-5-yl, 5-(1-methylethyl)-1,3,4-thiadiazol-2-yl, 5-(ethylthio)-1,3,4-thiadiazol-2-yl, 5-ethyl-1,3,4-thiadiazol-2-yl, or 4-(pyrrolidin-1-ylmethyl)-thiazol-2-yl.

when each of Z$^1$, Z$^2$ and Z$^3$ is CH; W$^1$ is —O—; W$^2$ is —C═; R$^4$ is H or C$_1$-C$_4$ alkyl; R$^2$ is phenyl; and X is —C(═O)—NH-†, then R$^1$ is other than tetrazol-5-yl.

In certain embodiments, the compound of Structural Formula (I) is represented by the following structure:

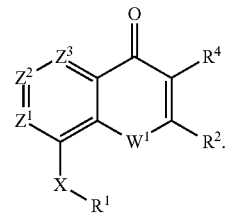

In certain embodiments, each of Z$^1$, Z$^2$ and Z$^3$ are independently CR. In certain embodiments, one of Z$^1$, Z$^2$, or Z$^3$ is N, such as Z$^1$ is N, or Z$^2$ is N, or Z$^3$ is N. In certain of these embodiments, R is H, such that in certain embodiments, each of Z$^1$ and Z$^2$ are —CH—, each of Z$^1$ and Z$^3$ are —CH—, each of Z$^2$ and Z$^3$ are —CH—, or all of Z$^1$, Z$^2$ and Z$^3$ are —CH—.

In certain embodiments, R is selected from hydrogen, —(C$_1$-C$_4$) alkyl-N(R$^7$)(R$^7$), —(C$_1$-C$_4$) alkyl-C(O)—N(R$^7$)(R$^7$), —(C$_2$-C$_4$) alkyl —O—R$^7$, and —(C$_2$-C$_4$) alkyl-N(R$^7$)—C(O)—R$^7$. In certain embodiments, R is hydrogen.

In certain embodiments, W$^1$ is selected from —O—, —NH—, or —N═. In certain embodiments, W$^2$ is selected from —NR$^4$— or —CR$^4$═. In other embodiments, when W$^1$ is —N═, then W$^2$ is selected from —NR$^4$— and —CR$^4$═. In certain embodiments, when W$^1$ is —O—, W$^2$ is —CR$^4$═. In certain embodiments, when W$^1$ is —NH—, W$^2$ is selected from —NR$^4$— and —CR$^4$═.

In certain embodiments, the compound of Structural Formula (I) is represented by the following structure:

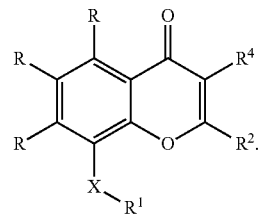

In certain embodiments, the compound of Structural Formula (I) is represented by the following structure:

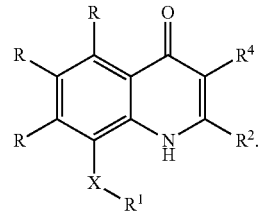

In certain embodiments, R$^4$ is selected from hydrogen, —C≡N, C$_1$-C$_4$ alkyl, and fluoro-substituted C$_1$-C$_4$ alkyl. In certain embodiments, R$^4$ is hydrogen. In certain embodiments wherein W$^1$ is —O— and W$^2$ is —CR$^4$═, R$^4$ is hydrogen. In certain embodiments, when Z$^1$, Z$^2$ and Z$^3$ are —CR—, R$^4$ is hydrogen.

In certain embodiments, X is —NH—C(═O)-† or —C(═O)—NH-†. In certain embodiments, X is —NH—C(═O)-†. In an exemplary embodiment, X is —NH—C(═O)-†, Z$^1$, Z$^2$ and Z$^3$ are CR, and R and R$^4$ are both H. In certain embodiments, $W^1$ is —O— and $W^2$ is —$CR^4$=, $Z^1$, $Z^2$ and $Z^3$ are all CR, R and $R^4$ are both H, and X is —NH—C(=O)-†.

In certain embodiments, the compound of Structural Formula (I) is represented by the following structure:

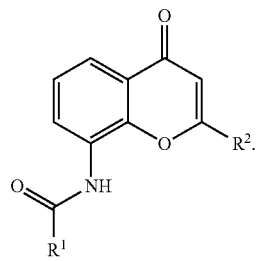

In certain embodiments, $R^1$ is selected from heterocycles (e.g., heteroaryls) comprising one or more heteroatoms selected from N, O and S. In particular embodiments, $R^1$ is selected from heterocycles (e.g., heteroaryls) comprising one or two nitrogens. In particular embodiments, $R^1$ is selected from heterocycles (e.g., heteroaryls) comprising up to three heteroatoms selected from S and N. In other embodiments, $R^1$ is selected from heterocycles (e.g., heteroaryls) comprising up to three heteroatoms selected from O and N.

Examples of $R^1$ include:

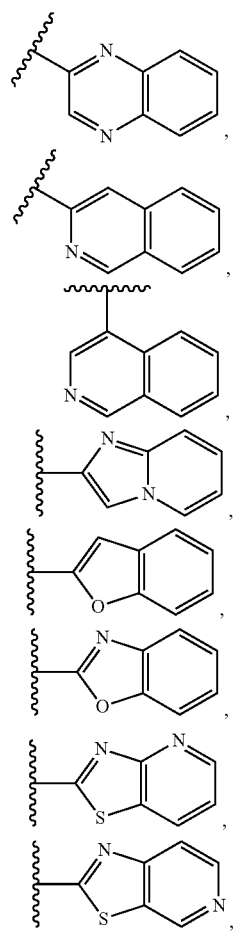

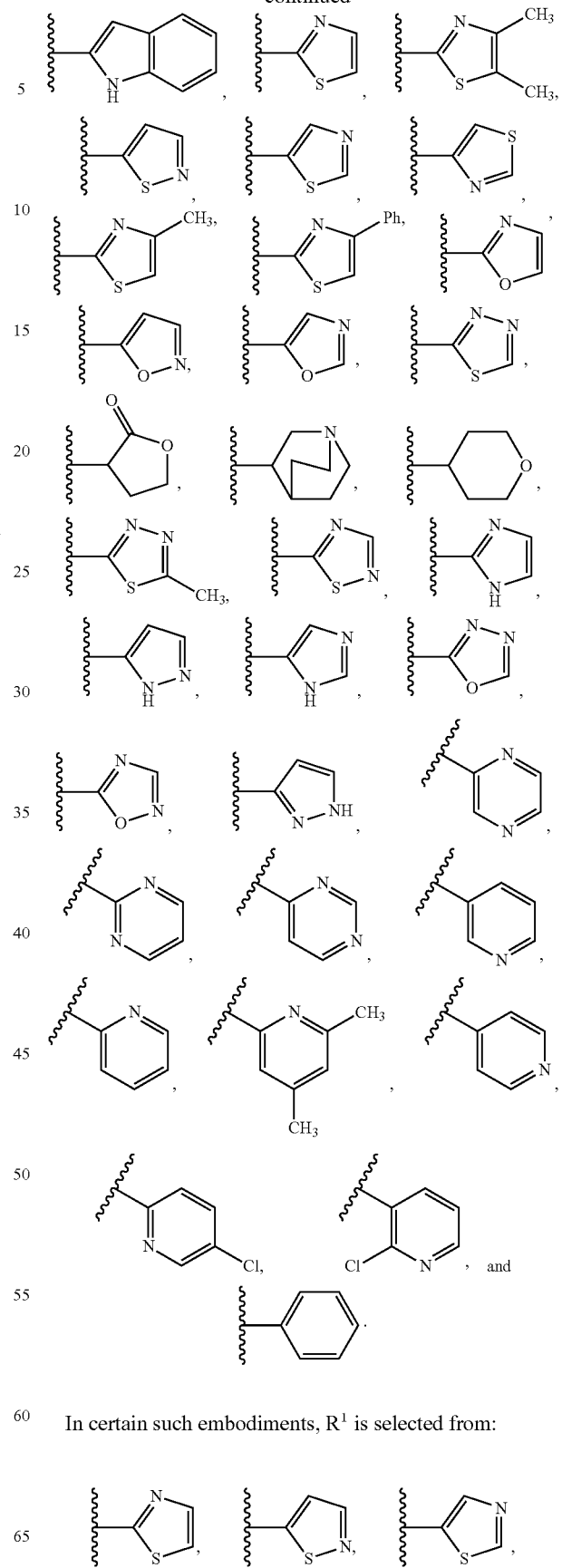

In certain such embodiments, $R^1$ is selected from:

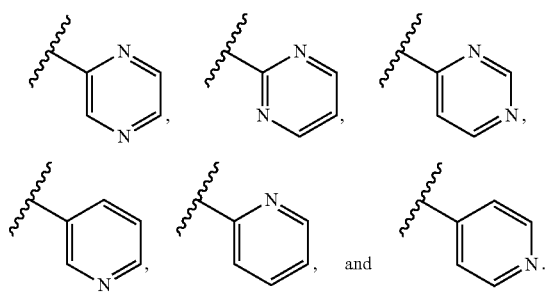

In the embodiments above, $R^1$ is optionally substituted by 1 or 2 substituents independently selected from halo, $(C_1-C_4)$ alkyl and =O. In certain embodiments, $R^1$ is thiazole or pyrazine optionally substituted with one or more substituents selected from halo and $(C_1-C_4)$ alkyl. In certain embodiments, $R^1$ is optionally substituted thiazole. In other embodiments, $R^1$ is optionally substituted pyrazine and X is —NH—C(=O)-†.

In certain embodiments, $R^2$ is selected from aryl and heteroaryl. In certain embodiments, $R^2$ is optionally substituted with one to two substituents independently selected from halo, —C≡N, $C_1-C_4$ alkyl, $C_1-C_2$ fluoro-substituted alkyl, —$OR^8$ wherein $R^8$ is alkyl optionally substituted with one or more halo substituents. In certain embodiments, $R^2$ is phenyl optionally substituted by one or more substituents independently selected from —Cl, —Br, —F, —C≡N, —$CF_3$ and —$OCF_3$.

Representative examples of $R^2$ include:

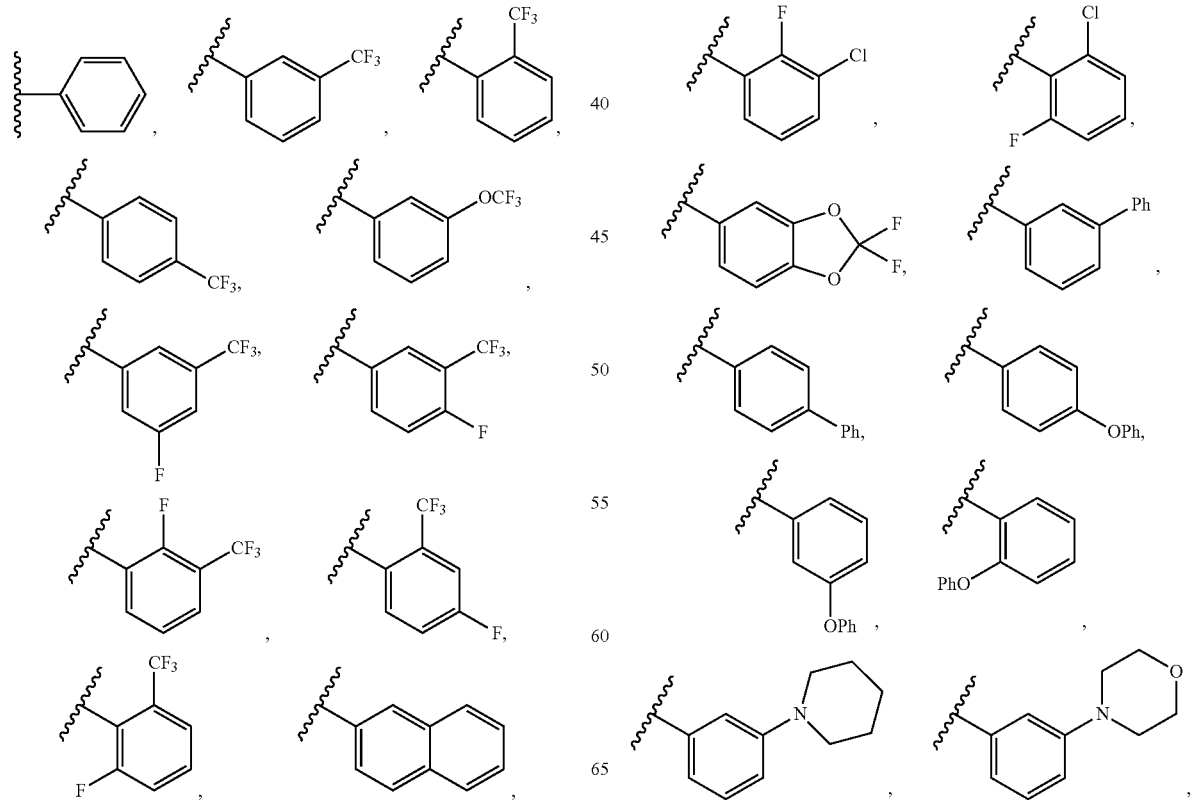

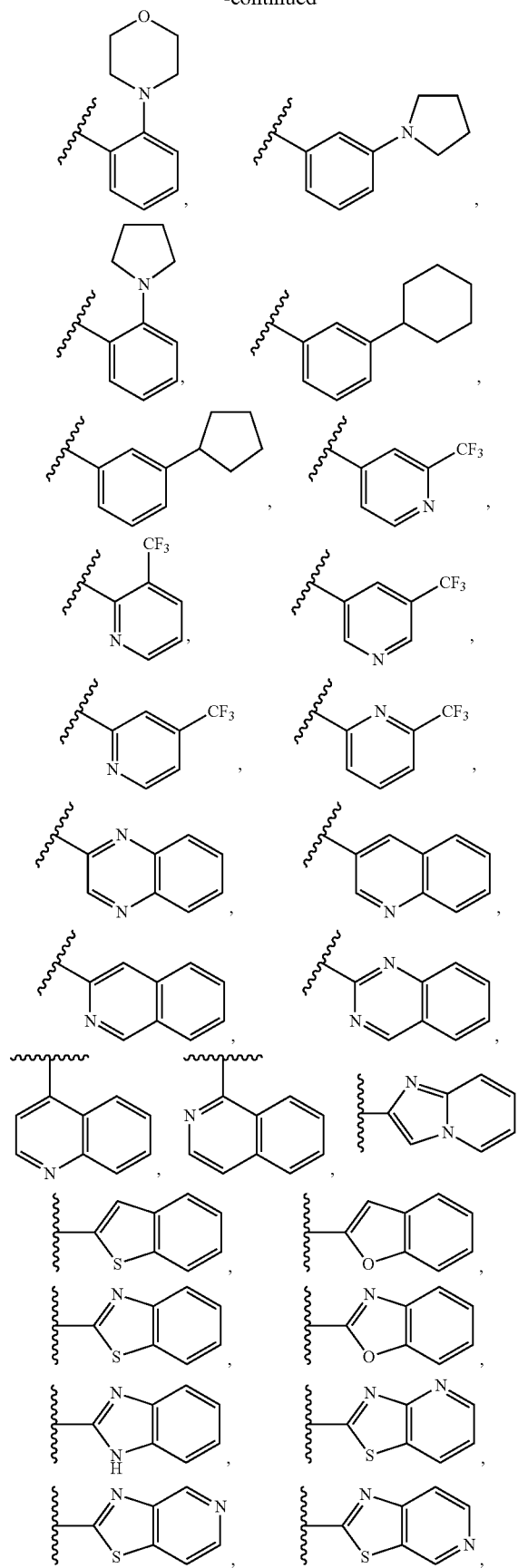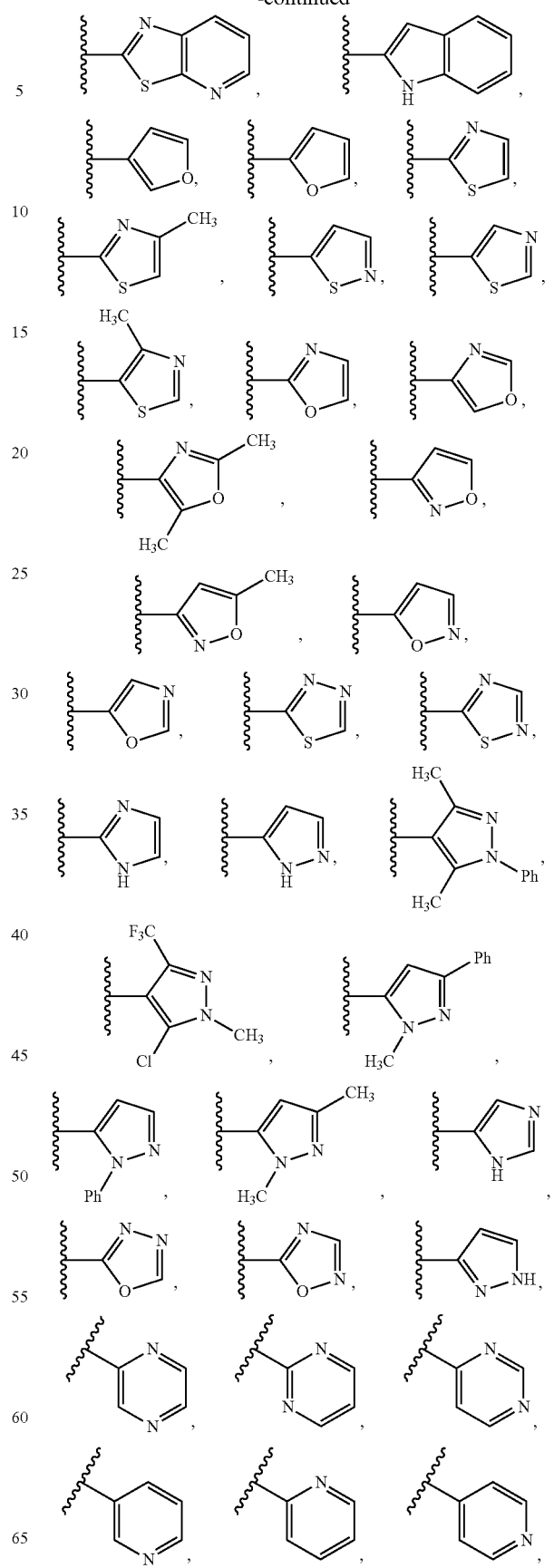

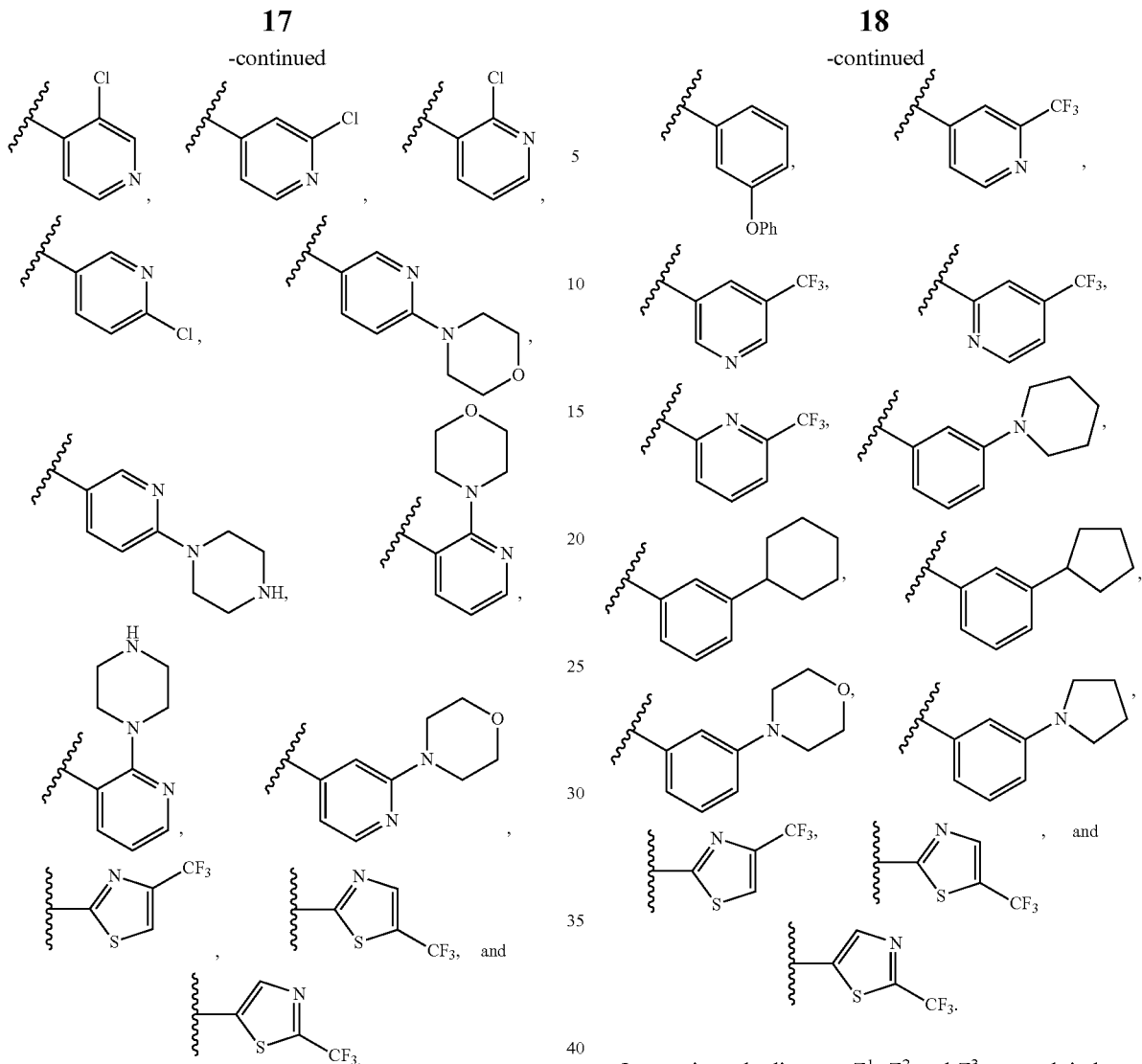

In particular embodiments, R² is meta-substituted relative to the attachment of R² to the rest of the compound, and wherein R² is optionally further substituted as described above. In certain embodiments, R² is selected from:

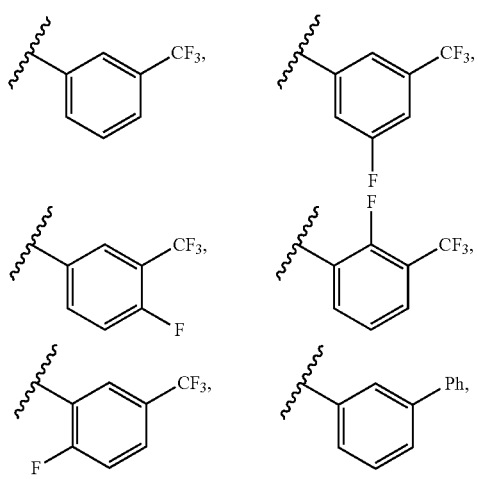

In certain embodiments, $Z^1$, $Z^2$ and $Z^3$ are each independently selected from CR, $W^1$ is selected from —O—, —N= and —N, $W^2$ is —$CR^4$= or —$NR^4$—, X is —NH—C(=O)-†, $R^1$ is optionally substituted thiazole or pyrazole and $R^2$ is optionally substituted phenyl. In particular embodiments, R is H.

In certain embodiments, sirtuin-modulating compounds of the invention are represented by Structural Formula (I)

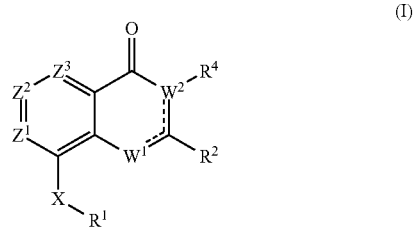

or a salt thereof, wherein $W^1$, $W^2$, $R^1$, $R^4$, $Z^1$, $Z^2$, and $Z^3$ are as previously defined and:

---- represents an optional bond, $R^2$ is selected from a carbocycle and a heterocycle, wherein $R^2$ is optionally substituted with one to two substituents independently selected from halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, and when $R^2$ is phenyl, $R^2$ is substituted with at least one substituent such as: halo, —C≡N, $C_1$-$C_4$ alkyl, $C_3$-$C_7$ cycloalkyl, $C_1$-$C_2$ fluoro-substituted alkyl, —O—$R^3$, —S—$R^3$, —($C_1$-$C_4$ alkyl)-N($R^3$)($R^3$), —N($R^3$)($R^3$), —O—($C_1$-$C_4$ alkyl)-N($R^3$)($R^3$), —($C_1$-$C_4$ alkyl)-O—($C_1$-$C_4$ alkyl)-N($R^3$)($R^3$), —C(O)—N($R^3$)($R^3$), —($C_1$-$C_4$ alkyl)-C(O)—N($R^3$)($R^3$), —O-phenyl, phenyl, and a second heterocycle, 3,4-methylenedioxy, fluoro-substituted 3,4-methylenedioxy, 3,4-ethylenedioxy, or fluoro-substituted 3,4-ethylenedioxy, wherein any phenyl or second heterocycle substituent of $R^2$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl and —N—($C_1$-$C_4$)$_2$ alkyl;

X is selected from —NH—C(=O)-†, —C(=O)—NH-†, —NH—C(=S)-†, —C(=S)—NH-†, —NH—S(=O)-†, —S(=O)—NH-†, —S(=O)$_2$—NH-†, —NH—S(=O)$_2$-†, —NH—S(O)$_2$—N$R^5$-†, —N$R^5$—S(O)$_2$—NH-†, —NH—C(=O)O-†, —OC(=O)NH-†, —NH—C(=O)N$R^5$-†, —N$R^5$—C(=O)NH-†, —NH—N$R^5$-†, —N$R^5$—NH-†, —O—NH-†, —NH—O-†, —NH—C(=N$R^5$)-†, —C(=N$R^5$)—NH-†, —C(=O)—NH—C$R^5R^6$-†, —C$R^5R^6$—NH—C(O)-†, —NH—C(=S)—C$R^5R^6$-†, —C$R^5R^6$—C(=S)—NH-†, —NH—S(O)—C$R^5R^6$-†, —C$R^5R^6$—S(O)—NH-†, —NH—S(O)$_2$—C$R^5R^6$-†, —C$R^5R^6$—S(O)$_2$—NH-†, —NH—C(=O)—O—C$R^5R^6$-†, —C$R^5R^6$—O—C(=O)—NH-†, —NH—C(=O)—N$R^5$—C$R^5R^6$-†, and —C$R^5R^6$—O—C(=O)—NH-†, wherein:

† represents where X is bound to $R^1$; and each $R^5$ and $R^6$ is independently selected from hydrogen, $C_1$-$C_4$ alkyl, —$CF_3$ and ($C_1$-$C_3$ alkyl)-$CF_3$.

In another embodiment, compounds of the invention are represented by Structural Formula (II):

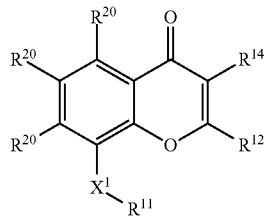

(II)

or a salt thereof, wherein:

each $R^{20}$ is independently selected from hydrogen, halo, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —S—($C_1$-$C_4$) alkyl, $C_3$-$C_7$ cycloalkyl, —($C_1$-$C_2$) alkyl-N($R^{13}$)($R^{13}$), —O—$CH_2CH(OH)CH_2OH$, —O—($C_1$-$C_3$) alkyl-N($R^{13}$)($R^{13}$), and —N($R^{13}$)($R^{13}$);

$R^{11}$ is selected from a carbocycle and a heterocycle, wherein $R^{11}$ is optionally substituted with one to two substitutents independently selected from halo, —C≡N, $C_1$-$C_4$ alkyl, =O, $C_3$-$C_7$ cycloalkyl, fluoro-substituted $C_1$-$C_4$ alkyl, —O—$R^{13}$, —S—$R^{13}$, —($C_1$-$C_4$ alkyl)-N($R^{13}$)($R^{13}$), —N($R^{13}$)($R^{13}$), —O—($C_1$-$C_4$alkyl)-N($R^{13}$)($R^{13}$), —($C_1$-$C_4$ alkyl)-O—($C_1$-$C_4$ alkyl)-N($R^{13}$)($R^{13}$), —C(O)—N($R^{13}$)($R^{13}$), and —($C_1$-$C_4$ alkyl)-C(O)—N($R^{13}$)($R^{13}$), and when $R^{11}$ is phenyl, $R^{11}$ is also optionally substituted with 3,4-methylenedioxy, fluoro-substituted 3,4-methylenedioxy, 3,4-ethylenedioxy, fluoro-substituted 3,4-ethylenedioxy, 0-(saturated heterocycle), fluoro-substituted —O-(saturated heterocycle), or $C_1$-$C_4$ alkyl-substituted O-(saturated heterocycle), wherein each $R^{13}$ is independently selected from hydrogen and —$C_1$-$C_4$ alkyl; or two $R^{13}$ are taken together with the nitrogen atom to which they are bound to form a 4- to 8-membered saturated heterocycle optionally comprising one additional heteroatomic unit selected from NH, S, S(=O), S(=O)$_2$, and O, wherein when $R^{13}$ is alkyl, the alkyl is optionally substituted with one or more substituents selected from —OH, fluoro, —$NH_2$, —NH($C_1$-$C_4$ alkyl), —N($C_1$-$C_4$ alkyl)$_2$, —NH($CH_2CH_2OCH_3$), and —N($CH_2CH_2OCH_3$)$_2$, and when two $R^{13}$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —$NH_2$, —NH($C_1$-$C_4$ alkyl), —N($C_1$-$C_4$ alkyl)$_2$, —NH($CH_2CH_2OCH_3$), or —N($CH_2CH_2OCH_3$)$_2$, and optionally substituted at any substitutable nitrogen atom with —$C_1$-$C_4$ alkyl, fluoro-substituted $C_1$-$C_4$ alkyl, or —($CH_2$)$_2$—O—$CH_3$;

$R^{12}$ is selected from a carbocycle and a heterocycle other than optionally substituted tetrazolyl, wherein $R^{12}$ is optionally substituted with one or more substituents independently selected from halo, —C≡N, $C_1$-$C_4$ alkyl, $C_3$-$C_7$ cycloalkyl, $C_1$-$C_2$ fluoro-substituted alkyl, —O—$R^{13}$, —S—$R^{13}$, —S(O)—$R^{13}$, —S(O)$_2$—$R^{13}$, —($C_1$-$C_4$ alkyl)-N($R^{13}$)($R^{13}$), —N($R^{13}$)($R^{13}$), —O—($C_1$-$C_4$ alkyl)-N($R^{13}$)($R^{13}$), —($C_1$-$C_4$ alkyl)-O—($C_1$-$C_4$ alkyl)-N($R^{13}$)($R^{13}$), —C(O)—N($R^{13}$)($R^{13}$), —($C_1$-$C_4$ alkyl)-C(O)—N($R^{13}$)($R^{13}$), —O-phenyl, phenyl, and a second heterocycle, and when $R^{12}$ is phenyl, $R^{12}$ may also be optionally substituted with 3,4-methylenedioxy, fluoro-substituted 3,4-methylenedioxy, 3,4-ethylenedioxy, or fluoro-substituted 3,4-ethylenedioxy, or —O-(saturated heterocycle), wherein any phenyl, second heterocycle or saturated heterocycle portion of a substituent of $R^{12}$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl and —N—($C_1$-$C_4$)$_2$ alkyl;

$R^{14}$ is selected from hydrogen, $C_1$-$C_4$ alkyl, $C_1$-$C_4$ fluoro-substituted alkyl, $C_1$-$C_4$ alkyl-N($R^{13}$)($R^{13}$), $C_1$-$C_4$ alkyl-C(O)—N($R^{13}$)($R^{13}$), $C_1$-$C_4$ alkyl-O—$R^{13}$, and $C_1$-$C_4$ alkyl-N$R^{13}$—C(O)$R^{13}$; and $X^1$ is selected from —NH—C(=O)-†, —C(=O)—NH-†, —NH—C(=S)-†, —C(=S)—NH-†, —NH—S(=O)-†, —S(=O)—NH-†, —S(=O)$_2$—NH-†, —NH—S(=O)$_2$-†, —NH—S(O)$_2$—N$R^{15}$-†, —N$R^{15}$—S(O)$_2$—NH-†, —NH—C(=O)O-†, —OC(=O)NH-†, —NH—C(=O)N$R^{15}$-†, —N$R^{15}$—C(=O)NH-†, —NH—N$R^{15}$-†, —N$R^{15}$—NH-†, —O—NH-†, —NH—O-†, —NH—C$R^{15}R^{16}$-†, —C$R^{15}R^{16}$—NH-†, —NH—C(=N$R^{15}$)-†, —C(=N$R^{15}$)—NH-†, —C(=O)—NH—C$R^{15}R^{16}$-†, —C$R^{15}R^{16}$—NH—C(O)-†, —NH—C(=S)—C$R^{15}R^{16}$-†, —C$R^{15}R^{16}$—C(=S)—NH-†, —NH—S(O)—C$R^{15}R^{16}$-†, —C$R^{15}R^{16}$—S(O)—NH-†, —NH—S(O)$_2$—C$R^{15}R^{16}$-†, —C$R^{15}R^{16}$—S(O)$_2$—NH-†, —NH—C(=O)—O—C$R^{15}R^{16}$-†, —C$R^{15}R^{16}$—O—C(=O)—NH-†, —NH—C(=O)—N$R^{15}$—C$R^{15}R^{16}$-†, —NH—C(=O)—C$R^{15}R^{16}$-†, and —C$R^{15}R^{16}$—NH—C(=O)—O-†, wherein:

† represents where $X^1$ is bound to $R^{11}$; and each $R^{15}$ and $R^{16}$ is independently selected from hydrogen, $C_1$-$C_4$ alkyl, —$CF_3$ and ($C_1$-$C_3$ alkyl)-$CF_3$.

In certain embodiments, compounds represented by Structural Formula (II) may be characterized by one or more of the following features:

when $R^{14}$ is H; and $X^1$ is —NH—$CR^{15}R^{16}$-† or —$CR^{15}R^{16}$—NH-†, then $R^{12}$ is other than optionally substituted pyridin-4-yl, optionally substituted pyridin-3-yl or unsubstituted morpholin-4-yl;

when $R^{14}$ is H; $R^{12}$ is phenyl; and $X^1$ is —C(=O)—NH-†, then $R^{11}$ is other than 1H-pyrazol-3-yl or tetrazol-5-yl;

when $R^{14}$ is $C_1$-$C_4$ alkyl, $R^{12}$ is other than optionally substituted phenyl;

each $R^{20}$ is independently selected from hydrogen, halo, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_2$-$C_4$ alkyl, —S—($C_1$-$C_4$) alkyl, $C_3$-$C_7$ cycloalkyl, —($C_1$-$C_2$) alkyl-N($R^{13}$)($R^{13}$), —O—$CH_2CH(OH)CH_2OH$, —O—($C_1$-$C_3$) alkyl-N($R^{13}$)($R^{13}$), and —N($R^{13}$)($R^{13}$);

each $R^{15}$ and $R^{16}$ is independently selected from hydrogen, $C_2$-$C_4$ alkyl, —$CF_3$ and ($C_1$-$C_3$ alkyl)-$CF_3$;

$R^{11}$ is other than optionally substituted piperidine or optionally substituted pyrrolidine;

$R^{12}$ is selected from a carbocycle and a heterocycle having from 1 to 3 heteroatoms;

$R^{12}$ is selected from a carbocycle and a heterocycle having from 0 to 3 nitrogens;

$R^{12}$ is bound to the rest of the molecule through a ring carbon atom;

$R^{12}$ is optionally substituted with one or two substituents;

when $R^{12}$ is phenyl, $R^{12}$ is substituted with at least one substituent;

$X^1$ is selected from —NH—C(=O)-†, —C(=O)—NH-†, —NH—C(=S)-†, —C(=S)—NH-†, —NH—S(=O)-†, —S(=O)—NH-†, —S(=O)$_2$—NH-†, —NH—S(=O)$_2$-†, —NH—S(O)$_2$—$NR^{15}$-†, —$NR^{15}$—S(O)$_2$—NH-†, —NH—C(=O)O-†, —OC(=O)NH-†, —NH—C(=O)$NR^{15}$-†, —$NR^{15}$—C(=O)NH-†, —NH—$NR^{15}$-†, —$NR^{15}$—NH-†, —O—NH-†, —NH—O-†, —NH—C(=$NR^{15}$)-†, —C(=$NR^{15}$)—NH-†, —C(=O)—NH—$CR^{15}R^{16}$-†, —$CR^{15}R^{16}$—NH—C(O)-†, —NH—C(=S)—$CR^{15}R^{16}$-†, —$CR^{15}R^{16}$—C(=S)—NH-†, —NH—S(O)—$CR^{15}R^{16}$-†, —$CR^{15}R^{16}$—S(O)—NH-†, —NH—S(O)$_2$—$CR^{15}R^{16}$-†, —$CR^{15}R^{16}$—S(O)$_2$—NH-†, —NH—C(=O)—O—$CR^{15}R^{16}$-†, —$CR^{15}R^{16}$—O—C(=O)—NH-†, —NH—C(=O)—$NR^{15}$—$CR^{15}R^{16}$-†, —NH—C(=O)—$CR^{15}R^{16}$-†, and —$CR^{15}R^{16}$—NH—C(=O)—O-†;

$X^1$ is selected from —NH—C(O)-† and —C(O)—NH-†;

$X^1$ is —NH—C(O)-†;

$R^{11}$ is selected from:

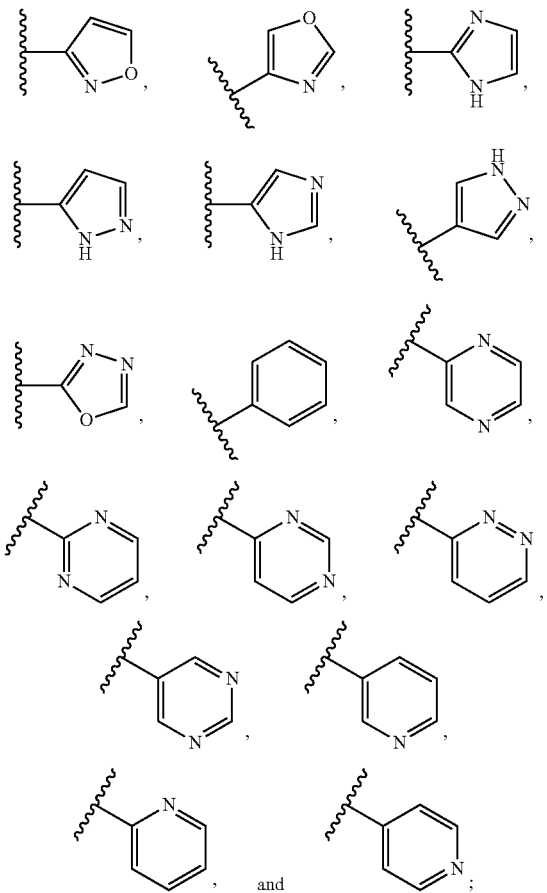

and $R^{11}$ is selected from:

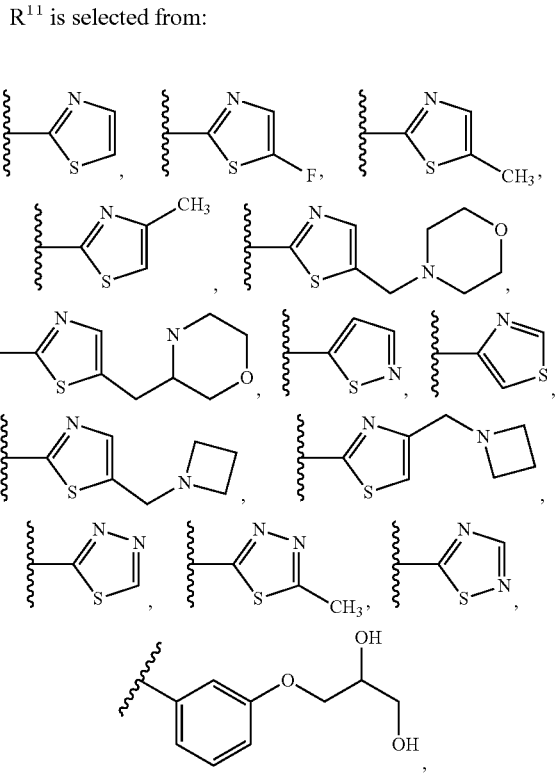

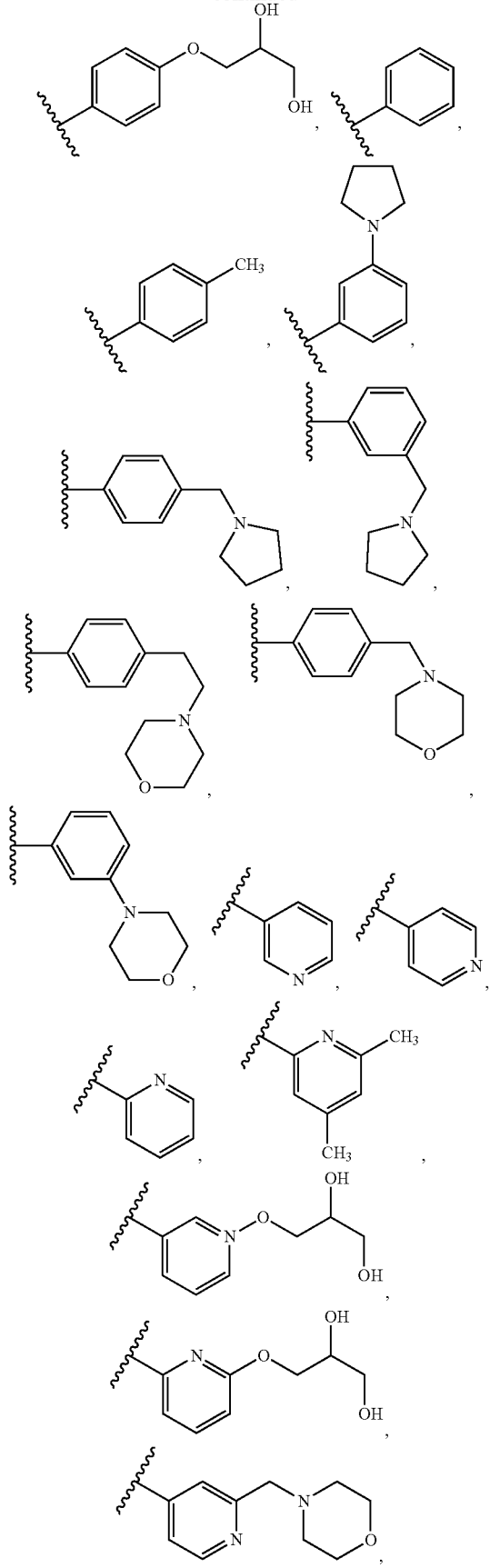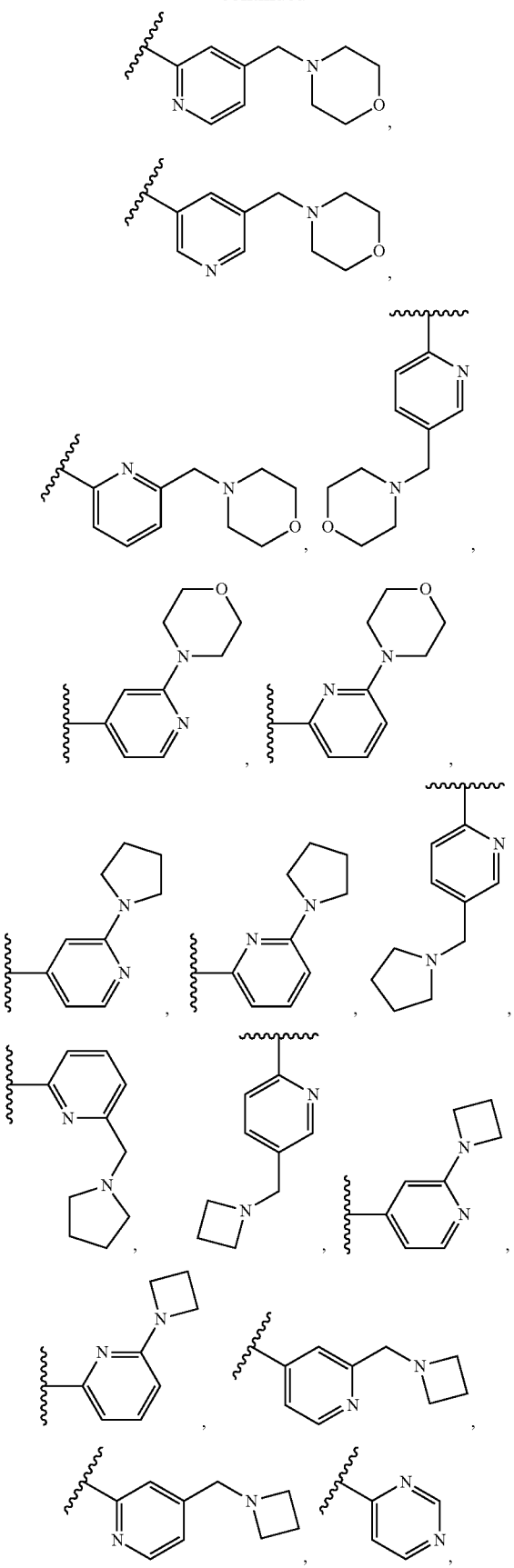

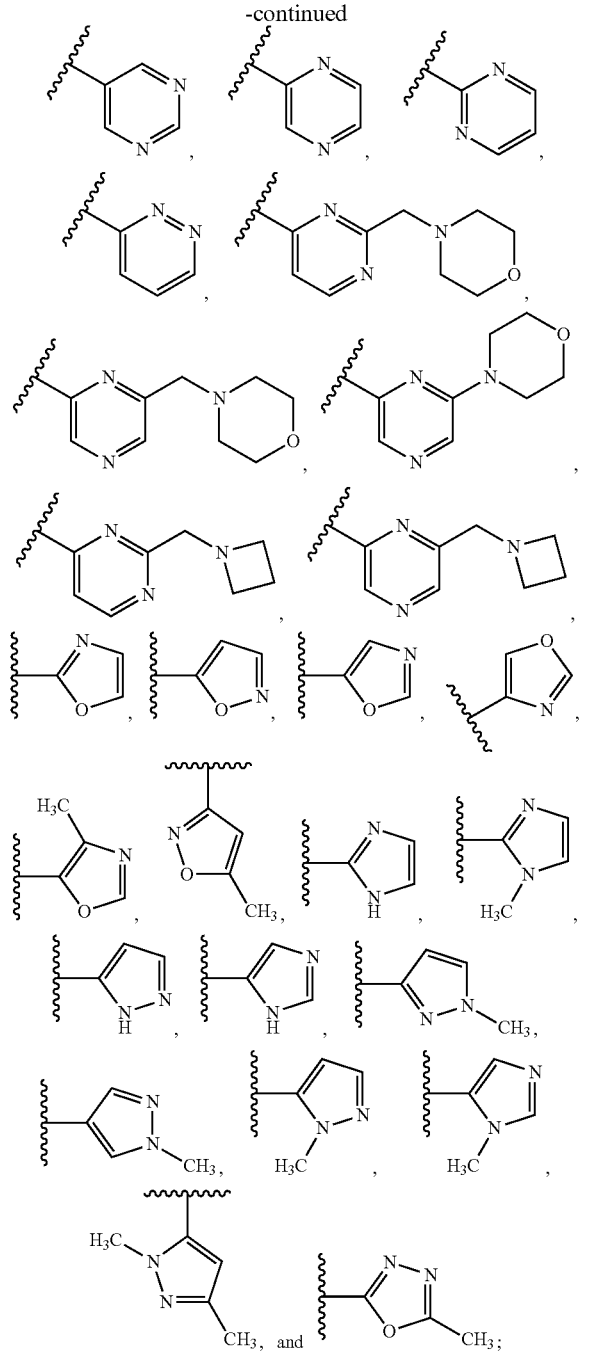
$R^{11}$ is selected from
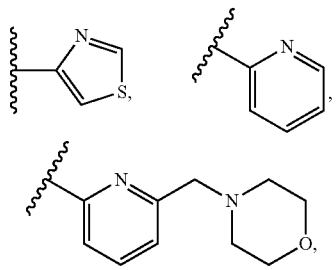
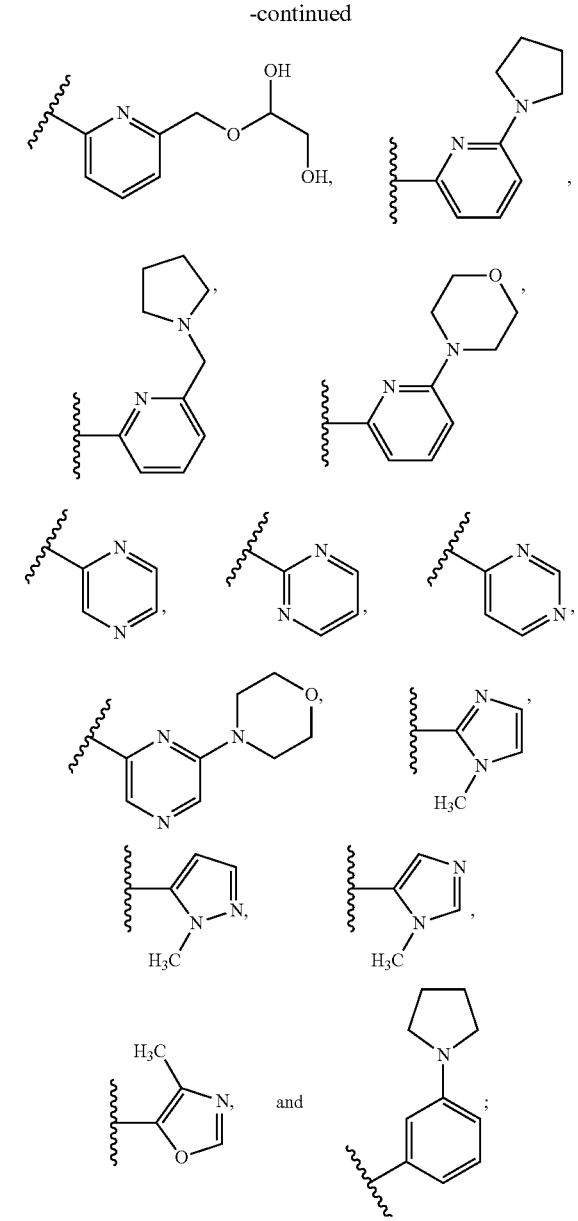
$R^{11}$ is optionally substituted with one to two substituents independently selected from halo, $C_1$-$C_4$ alkyl, —($C_1$-$C_4$ alkyl)-N($R^{13}$)($R^{13}$), —N($R^{13}$)($R^{13}$), and —O—$R^{13}$;
$R^{12}$ is selected from:
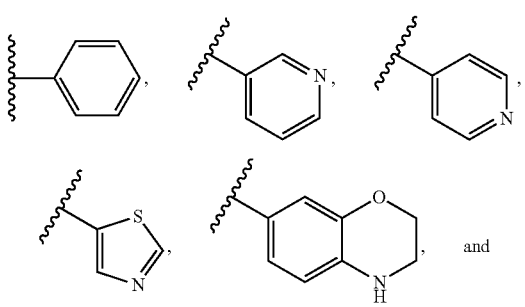

$R^{12}$ is selected from:

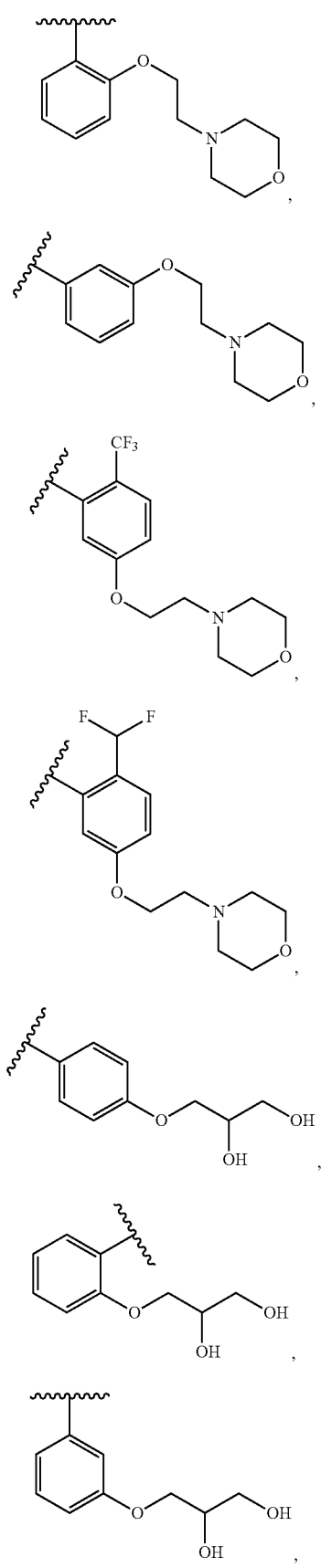
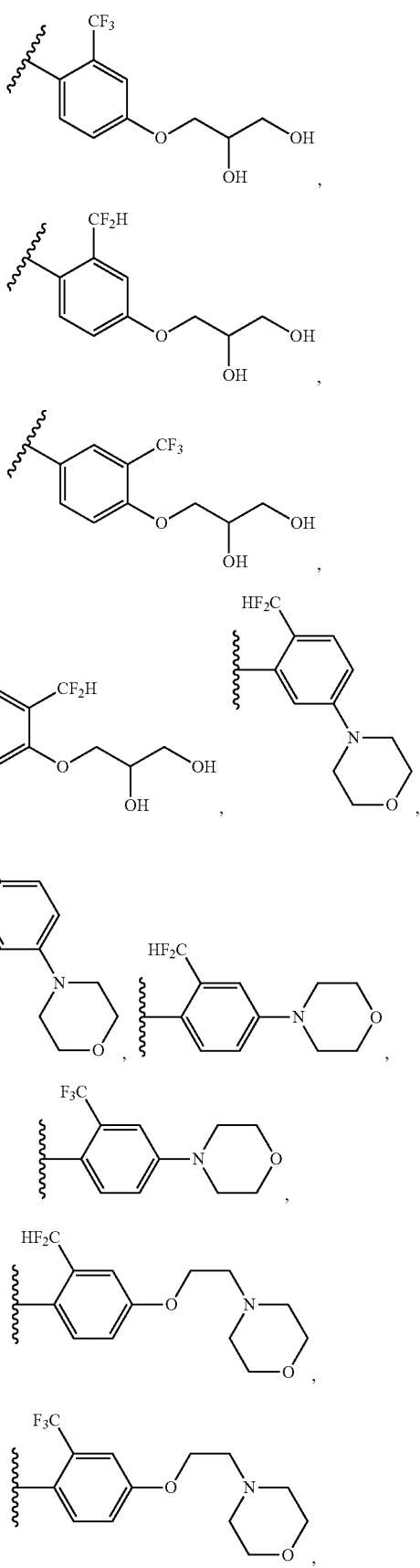

-continued

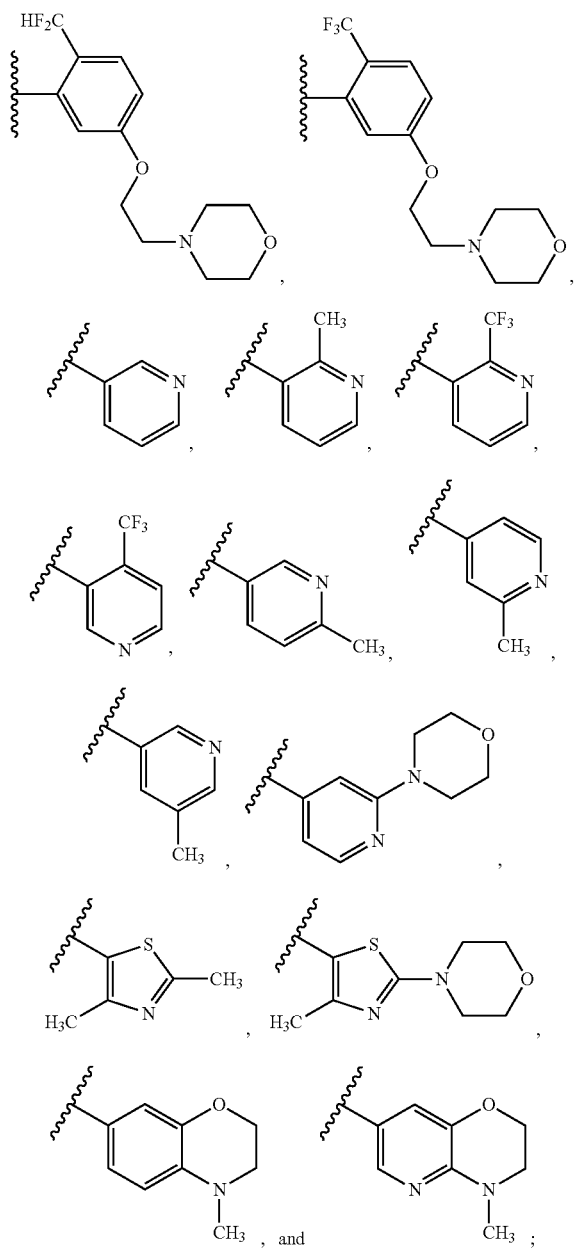

$R^{12}$ is selected from

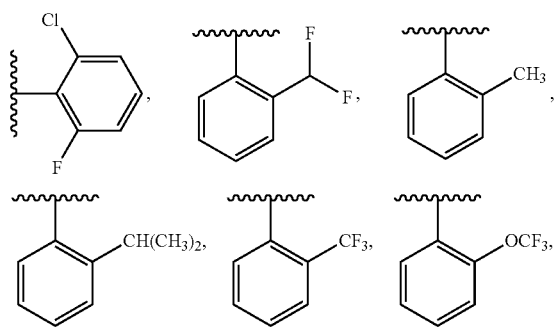

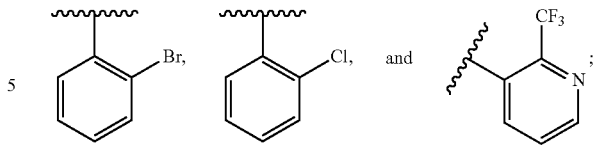

$R^{12}$ is optionally substituted with one or more groups independently selected from halo, $C_1$-$C_4$ alkyl, —($C_1$-$C_4$ alkyl)-$N(R^{13})(R^{13})$, $C_1$-$C_2$ fluoro-substituted alkyl, —O—$R^{13}$, —$SO_2$—$R^{13}$, —$N(R^{13})(R^{13})$, and —O—($C_1$-$C_4$ alkyl)-N$(R^{13})(R^{13})$; and $R^{12}$ is optionally substituted with one or two groups.

In certain embodiments, the invention provides a compound of Structural Formula III:

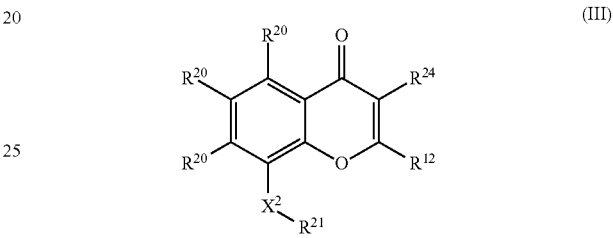

(III)

or a salt thereof, wherein $X^2$ is selected from —NH—C(=O)-†, —C(=O)—NH-†, —NH—C(=S)-†, —C(=S)—NH-†, —NH—S(=O)-†, —S(=O)—NH-†, —S(=O)$_2$—NH-†, —NH—S(=O)$_2$-†, —NH—S(O)$_2$—$NR^{15}$-†, —$NR^{15}$—S(O)$_2$—NH-†, —NH—C(=O)O-†, —OC(=O)NH-†, —NH—C(=O)$NR^{15}$-†, —$NR^{15}$—C(=O)NH-†, —NH—$NR^{15}$-†, —$NR^{15}$—NH-†, —O—NH-†, —NH—O-†, —NH—C(=$NR^{15}$)-†, —C(=$NR^{15}$)—NH-†, —C(=O)—NH—$CR^{15}R^{16}$-†, —$CR^{15}R^{16}$—NH—C(O)-†, —NH—C(=S)—$CR^{15}R^{16}$-†, —$CR^{15}R^{16}$—C(=S)—NH-†, —NH—S(O)—$CR^{15}R^{16}$-†, —$CR^{15}R^{16}$—S(O)—NH-†, —NH—S(O)$_2$—$CR^{15}R^{16}$-†, —$CR^{15}R^{16}$—S(O)$_2$—NH-†, —NH—C(=O)—O—$CR^{15}R^{16}$-†, —$CR^{15}R^{16}$—O—C(=O)—NH-†, —NH—C(=O)—$NR^{15}$—$CR^{15}R^{16}$-†, —NH—C(=O)—$CR^{15}R^{16}$-†, and —$CR^{15}R^{16}$—NH—C(=O)—O-†;

$R^{21}$ is selected from a carbocycle and a heterocycle other than 1H-pyrazol-3-yl or tetrazol-5-yl, wherein $R^{21}$ is optionally substituted with one to two substitutents independently selected from halo, —C≡N, $C_1$-$C_4$ alkyl, =O, $C_3$-$C_7$ cycloalkyl, fluoro-substituted $C_1$-$C_4$ alkyl, —O—$R^{13}$, —S—$R^{13}$, —($C_1$-$C_4$ alkyl)-$N(R^{13})(R^{13})$, —$N(R^{13})(R^{13})$, —O—($C_1$-$C_4$ alkyl)-$N(R^{13})(R^{13})$, —($C_1$-$C_4$ alkyl)-O—($C_1$-$C_4$ alkyl)-$N(R^{13})(R^{13})$, —C(O)—$N(R^{13})(R^{13})$, and —($C_1$-$C_4$ alkyl)-C(O)—$N(R^{13})(R^{13})$, and when $R^{11}$ is phenyl, $R^{11}$ is also optionally substituted with 3,4-methylenedioxy, fluoro-substituted 3,4-methylenedioxy, 3,4-ethylenedioxy, fluoro-substituted 3,4-ethylenedioxy, 0-(saturated heterocycle), fluoro-substituted —O-(saturated heterocycle), or $C_1$-$C_4$ alkyl-substituted 0-(saturated heterocycle);

$R^{24}$ is selected from hydrogen, $C_1$-$C_4$ fluoro-substituted alkyl, $C_1$-$C_4$ alkyl-$N(R^{13})(R^{13})$, $C_1$-$C_4$ alkyl-C(O)—$N(R^{13})(R^{13})$, $C_1$-$C_4$ alkyl-O—$R^{13}$, and $C_1$-$C_4$ alkyl-$NR^{13}$—C(O)$R^{13}$; and each of $R^{12}$, $R^{13}$, $R^{15}$, $R^{16}$, and $R^{20}$ "†" are as defined for a compound of Formula II.

In certain embodiments, compounds represented by Structural Formula (II) may be characterized by one or more of the following features:

each $R^{20}$ is independently selected from hydrogen, halo, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_2$-$C_4$ alkyl, —S—($C_1$-$C_4$) alkyl, $C_3$-$C_7$ cycloalkyl, —($C_1$-$C_2$) alkyl-N($R^{13}$)($R^{13}$), —O—CH$_2$CH(OH)CH$_2$OH, —O—($C_1$-$C_3$) alkyl-N($R^{13}$)($R^{13}$), and —N($R^{13}$)($R^{13}$);

each $R^{15}$ and $R^{16}$ is independently selected from hydrogen, $C_2$-$C_4$ alkyl, —CF$_3$ and ($C_1$-$C_3$ alkyl)-CF$_3$;

$R^{12}$ is bound to the rest of the molecule through a ring carbon atom; and $R^{12}$ is selected from a carbocycle and a heterocycle having from 1 to 3 heteroatoms;

$R^{12}$ is selected from a carbocycle and a heterocycle having from 0 to 3 nitrogens;

$R^{12}$ is optionally substituted with one or two substituents;

when $R^{12}$ is phenyl, $R^{12}$ is substituted with at least one substituent;

$R^{21}$ is selected from a carbocycle and a heterocycle having 0, 1, or 3 nitrogens;

$R^{21}$ is selected from a carbocycle and a 6- or 7-membered heterocycle having 0 to 4 nitrogens;

$R^{21}$ is other than optionally substituted piperidine or optionally substituted pyrrolidine;

$X^2$ is selected from —NH—C(O)-† and —C(O)—NH-†;

$X^2$ is —NH—C(O)-†;

$R^{21}$ is selected from:

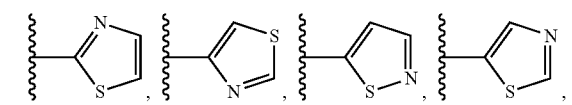

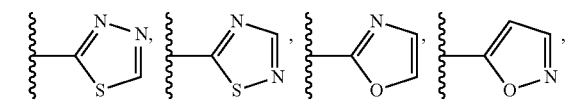

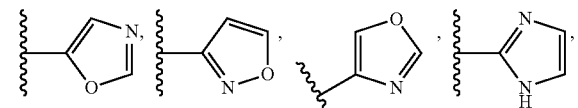

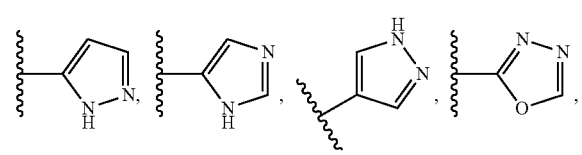

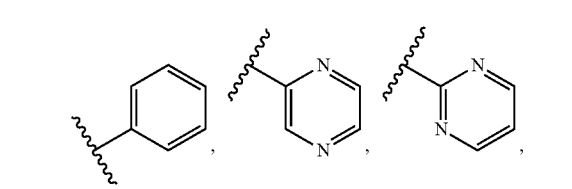

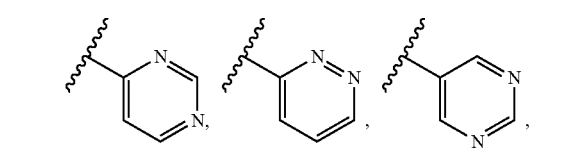

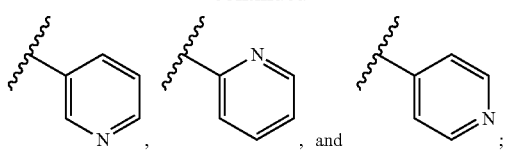

$R^{21}$ is selected from:

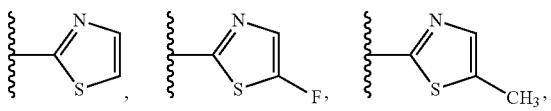

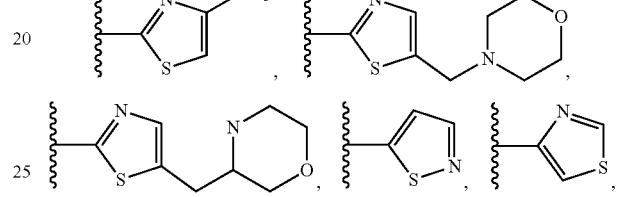

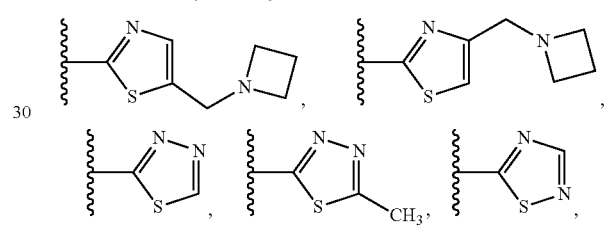

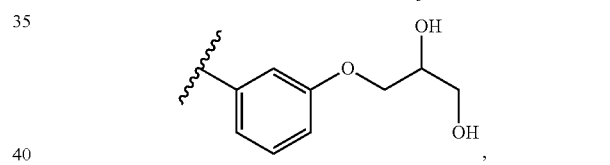

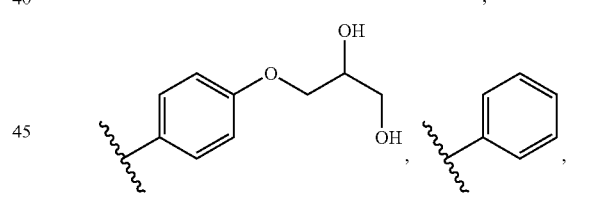

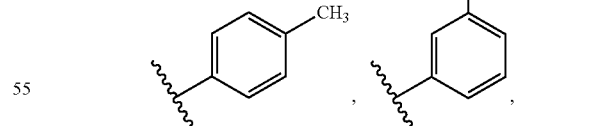

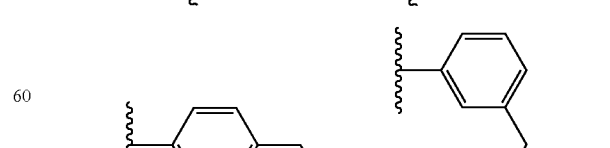

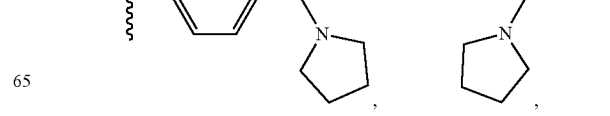

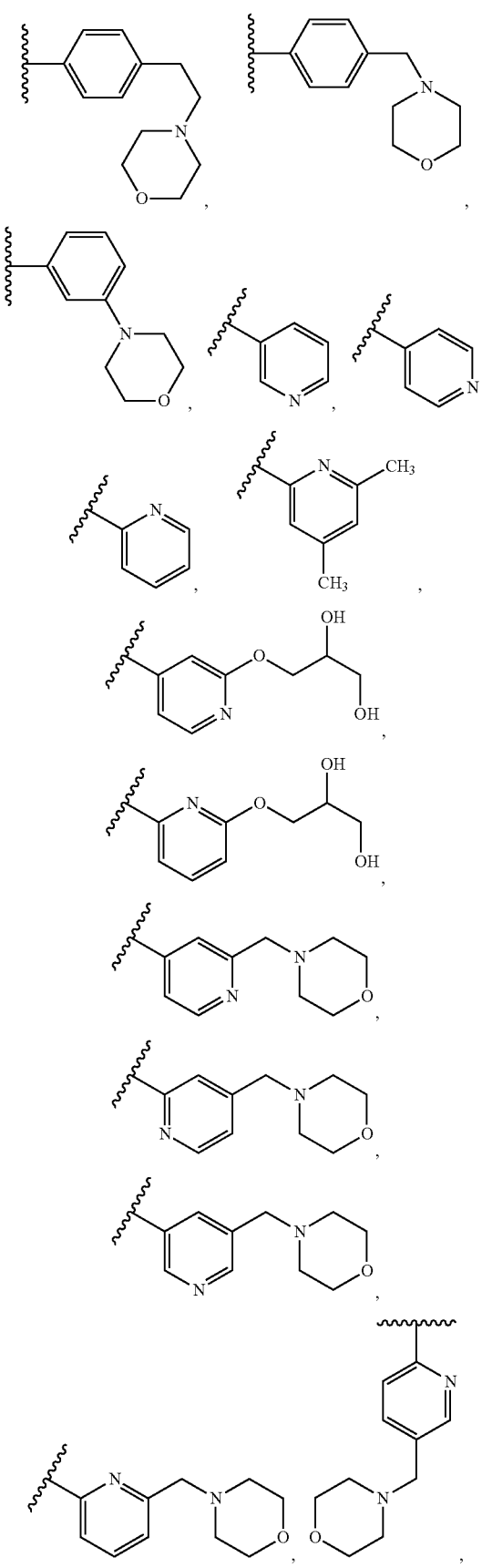
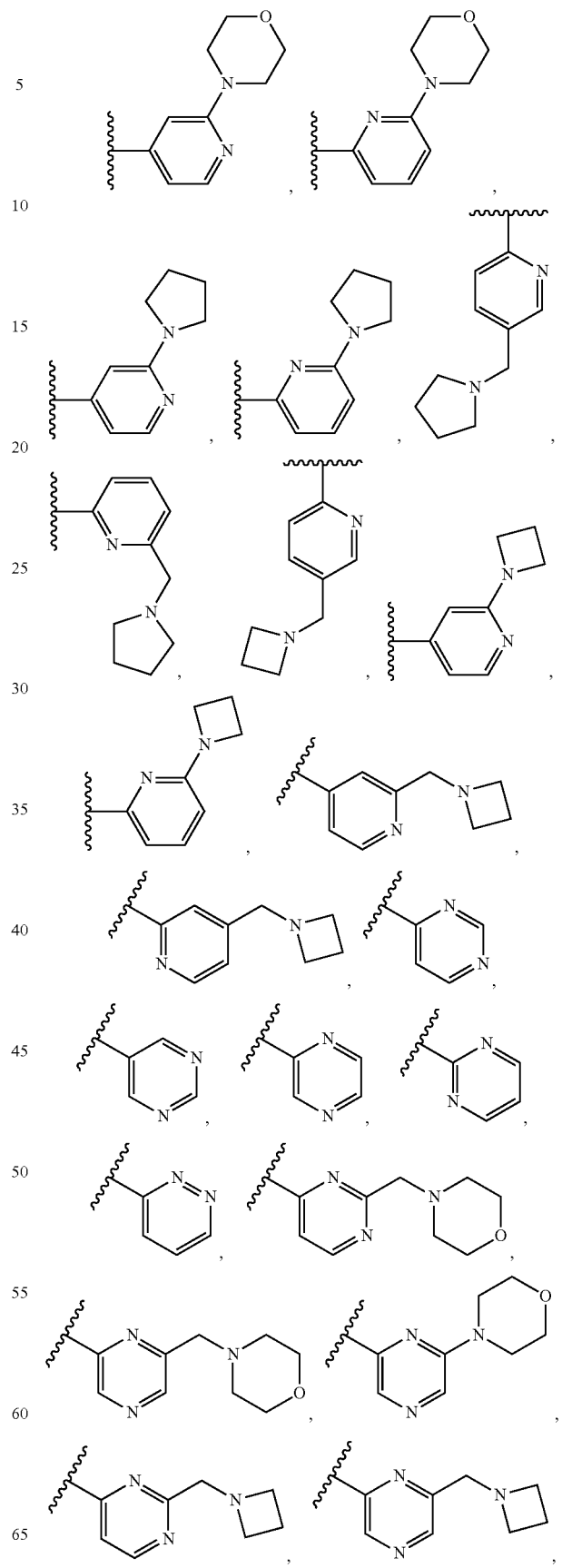

-continued
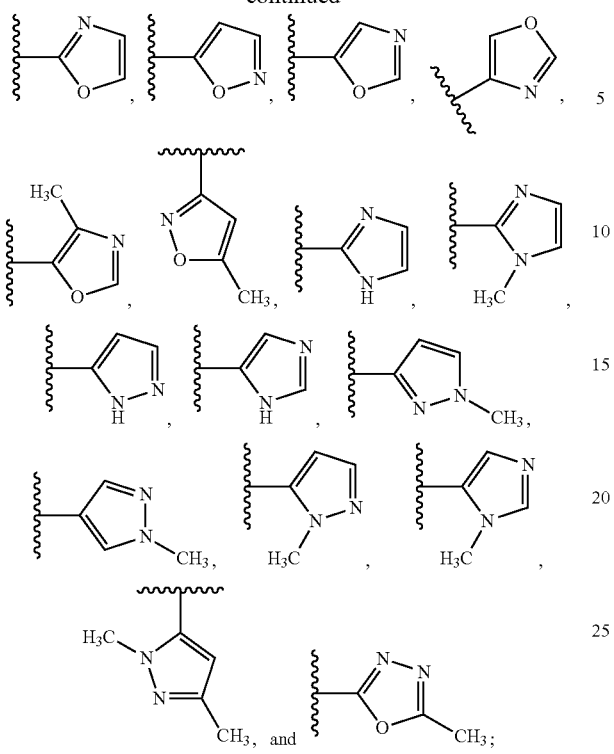
$R^{21}$ is selected from
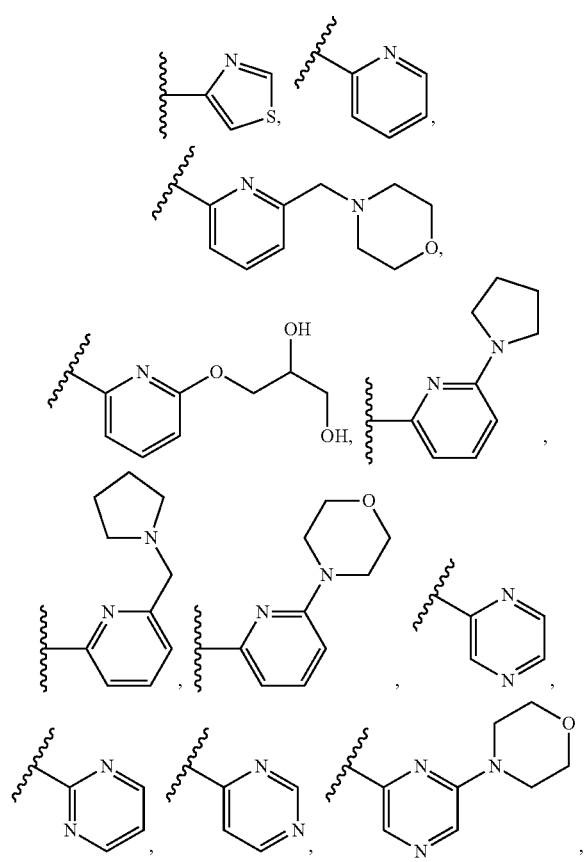
-continued
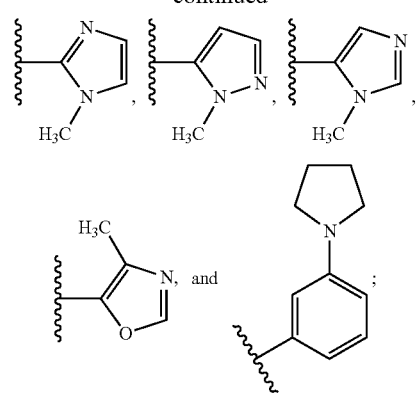
$R^{21}$ is optionally substituted with one to two substituents independently selected from halo, $C_1$-$C_4$ alkyl, —($C_1$-$C_4$ alkyl)-N($R^{13}$)($R^{13}$), —N($R^{13}$)($R^{13}$), and —O—$R^{13}$;
$R^{12}$ is selected from:
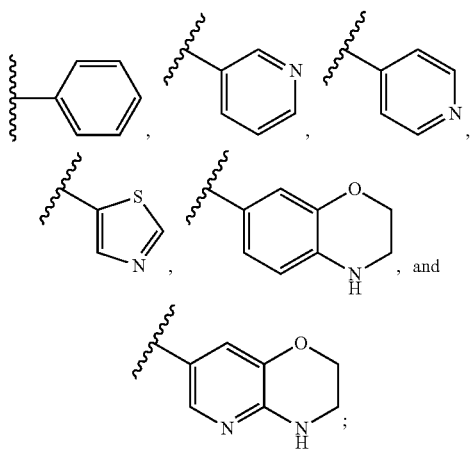
$R^{12}$ is selected from:
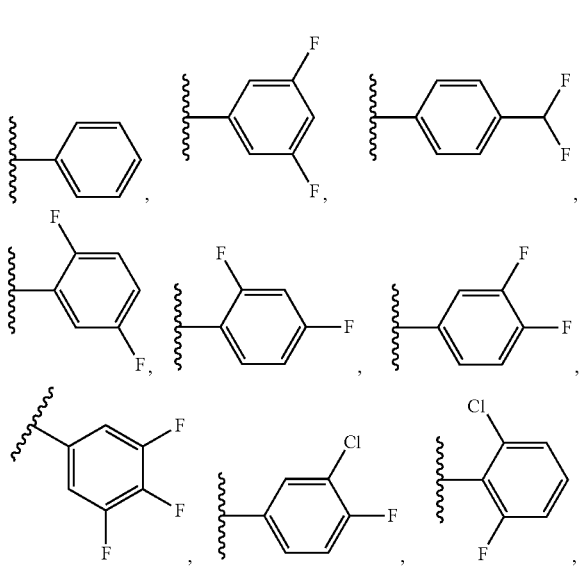

-continued
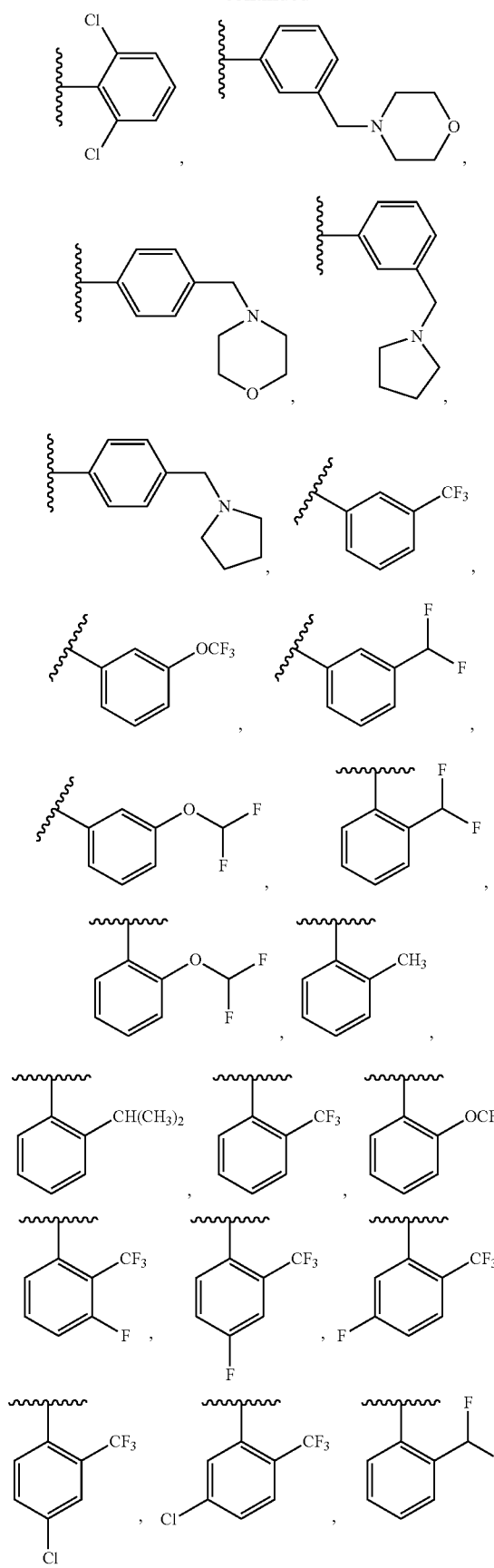
-continued
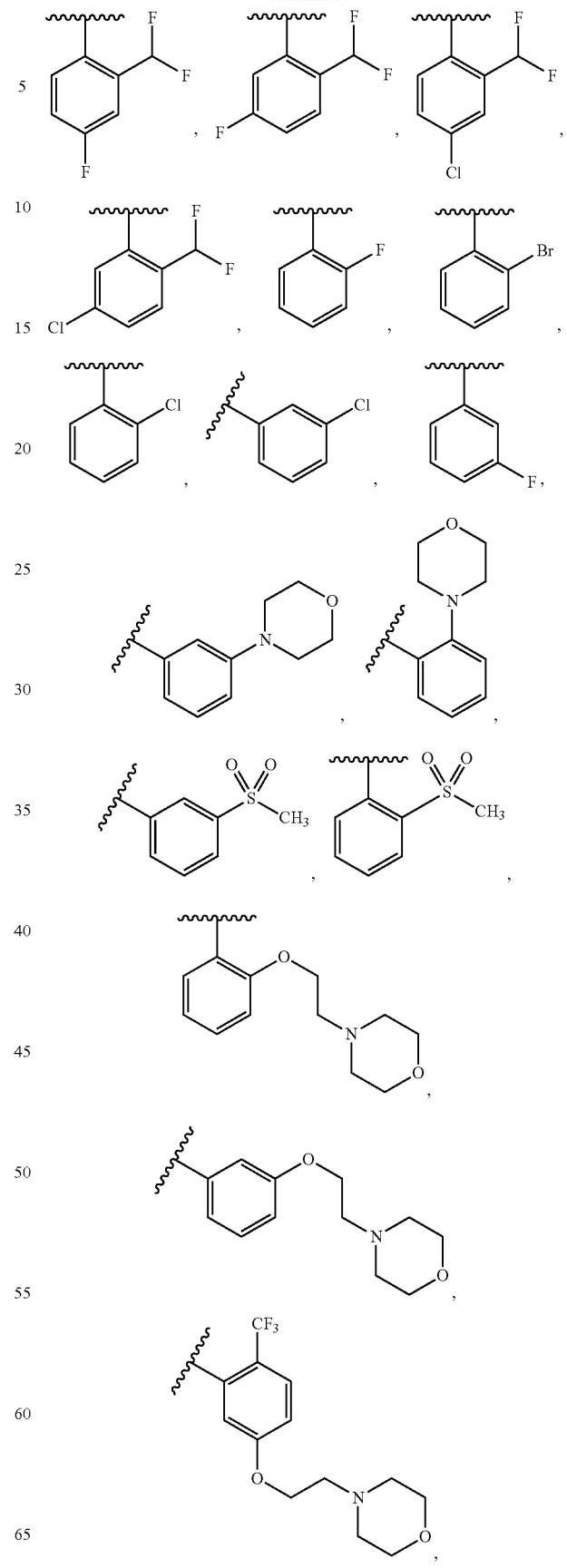

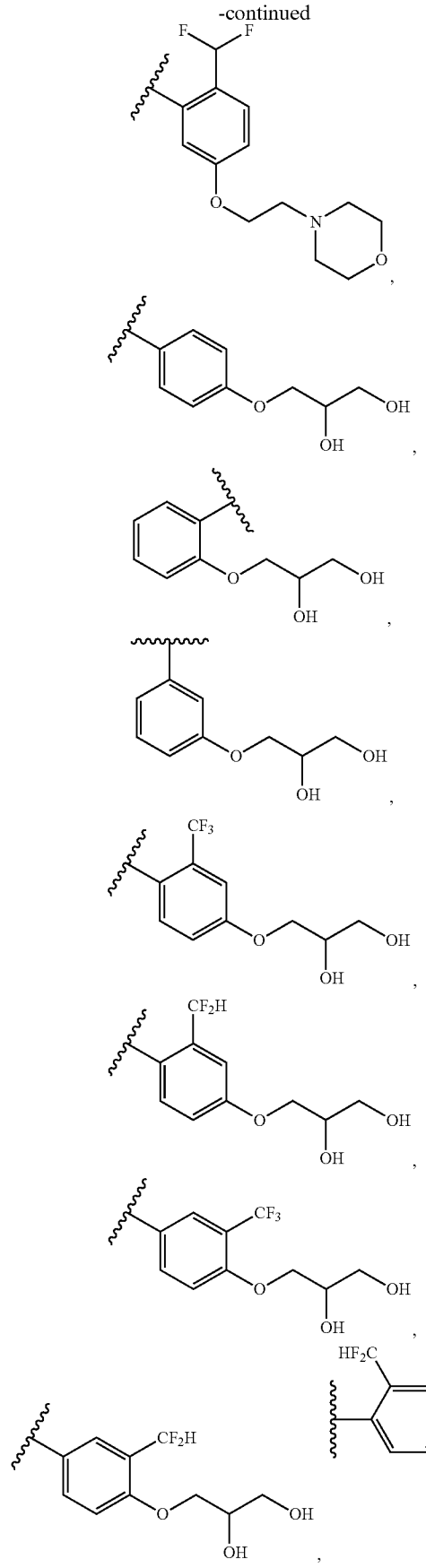

-continued

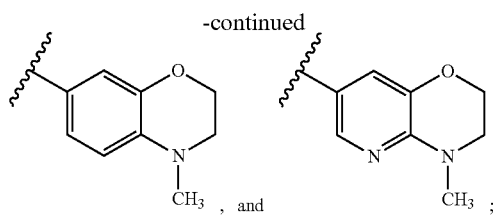

$R^{12}$ is selected from

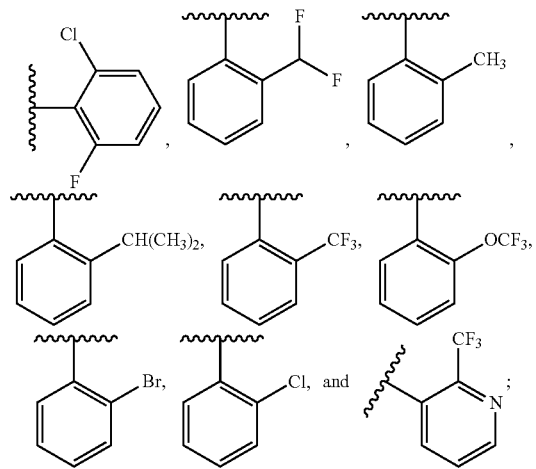

$R^{12}$ is optionally substituted with one or more groups independently selected from halo, $C_1$-$C_4$ alkyl, —($C_1$-$C_4$ alkyl)-N($R^{13}$)($R^{13}$), $C_1$-$C_2$ fluoro-substituted alkyl, —O—$R^{13}$, —SO$_2$—$R^{13}$, —N($R^{13}$)($R^{13}$), and —O—($C_1$-$C_4$ alkyl)-N($R^{13}$)($R^{13}$); and
$R^{12}$ is optionally substituted with one to two groups.

In certain embodiments, compounds of the invention are represented by Structural Formula (IV):

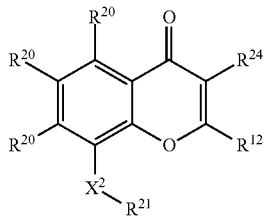

(IV)

or a salt thereof, wherein:
each $R^{20}$ is independently selected from hydrogen, halo, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —S—($C_1$-$C_4$) alkyl, $C_3$-$C_7$ cycloalkyl, —($C_1$-$C_2$) alkyl-N($R^{13}$)($R^{13}$), —O—CH$_2$CH(OH)CH$_2$OH, —O—($C_1$-$C_3$) alkyl-N($R^{13}$)($R^{13}$), and —N($R^{13}$)($R^{13}$);

$R^{21}$ is selected from a carbocycle and a heterocycle, wherein $R^{21}$ is optionally substituted with one to two substitutents independently selected from halo, —C≡N, $C_1$-$C_4$ alkyl, =O, $C_3$-$C_7$ cycloalkyl, fluoro-substituted $C_1$-$C_4$ alkyl, —O—$R^{13}$, —S—$R^{13}$, —($C_1$-$C_4$ alkyl)-N($R^{13}$)($R^{13}$), —N($R^{13}$)($R^{13}$), —O—($C_1$-$C_4$ alkyl)-N($R^{13}$)($R^{13}$), —($C_1$-$C_4$ alkyl)-O—($C_1$-$C_4$ alkyl)-N($R^{13}$)($R^{13}$), —C(O)—N($R^{13}$)($R^{13}$), and —($C_1$-$C_4$ alkyl)-C(O)—N($R^{13}$)($R^{13}$), and when $R^{11}$ is phenyl, $R^{11}$ is also optionally substituted with 3,4-methylenedioxy, fluoro-substituted 3,4-methylenedioxy, 3,4-ethylenedioxy, fluoro-substituted 3,4-ethylenedioxy, O-(saturated heterocycle), fluoro-substituted —O-(saturated heterocycle), or $C_1$-$C_4$ alkyl-substituted O-(saturated heterocycle);

each $R^{13}$ is independently selected from hydrogen and —$C_1$-$C_4$ alkyl; or two $R^{13}$ are taken together with the nitrogen atom to which they are bound to form a 4- to 8-membered saturated heterocycle optionally comprising one additional heteroatomic unit selected from NH, S, S(=O), S(=O)$_2$, and O, wherein
when $R^{13}$ is alkyl, the alkyl is optionally substituted with one or more substituents selected from —OH, fluoro, —NH$_2$, —NH($C_1$-$C_4$ alkyl), —N($C_1$-$C_4$ alkyl)$_2$, —NH(CH$_2$CH$_2$OCH$_3$), and —N(CH$_2$CH$_2$OCH$_3$)$_2$ and
when two $R^{13}$ are taken together with the nitrogen atom to which they are bound to form a 4- to 8-membered saturated heterocycle, the saturated heterocycle is optionally substituted at any carbon atom with —OH, —$C_1$-$C_4$ alkyl, fluoro, —NH$_2$, —NH($C_1$-$C_4$ alkyl), —N($C_1$-$C_4$ alkyl)$_2$, —NH(CH$_2$CH$_2$OCH$_3$), or —N(CH$_2$CH$_2$OCH$_3$)$_2$, and optionally substituted at any substitutable nitrogen atom with —$C_1$-$C_4$ alkyl, fluoro-substituted $C_1$-$C_4$ alkyl, or —(CH$_2$)$_2$—O—CH$_3$;

$R^{12}$ is selected from a carbocycle and a heterocycle having from 1 to 3 heteroatoms, wherein $R^{12}$ is optionally substituted with one or more substitutents independently selected from halo, —C≡N, $C_1$-$C_4$ alkyl, $C_3$-$C_7$ cycloalkyl, $C_1$-$C_2$ fluoro-substituted alkyl, —O—$R^{13}$, —S—$R^{13}$, —S(O)—$R^{13}$, —S(O)$_2$—$R^{13}$, —($C_1$-$C_4$ alkyl)-N($R^{13}$)($R^{13}$), —N($R^{13}$)($R^{13}$), —O—($C_1$-$C_4$ alkyl)-N($R^{13}$)($R^{13}$), —($C_1$-$C_4$ alkyl)-O—($C_1$-$C_4$ alkyl)-N($R^{13}$)($R^{13}$), —C(O)—N($R^{13}$)($R^{13}$), —($C_1$-$C_4$ alkyl)-C(O)—N($R^{13}$)($R^{13}$), —O-phenyl, phenyl, and a second heterocycle, and when $R^{12}$ is phenyl, $R^{12}$ is substituted with at least one substituent which may further be selected from 3,4-methylenedioxy, fluoro-substituted 3,4-methylenedioxy, 3,4-ethylenedioxy, or fluoro-substituted 3,4-ethylenedioxy, or —O-(saturated heterocycle), wherein any phenyl, second heterocycle or saturated heterocycle portion of a substituent of $R^{12}$ is optionally substituted with halo, —C≡N, $C_1$-$C_4$ alkyl, fluoro-substituted $C_1$-$C_2$ alkyl, —O—($C_1$-$C_2$) fluoro-substituted alkyl, —O—($C_1$-$C_4$) alkyl, —S—($C_1$-$C_4$) alkyl, —S—($C_1$-$C_2$) fluoro-substituted alkyl, —NH—($C_1$-$C_4$) alkyl and —N—($C_1$-$C_4$)$_2$ alkyl;

$R^{24}$ is selected from hydrogen, $C_1$-$C_4$ fluoro-substituted alkyl, $C_1$-$C_4$ alkyl-N($R^{13}$)($R^{13}$), $C_1$-$C_4$ alkyl-C(O)—N($R^{13}$)($R^{13}$), $C_1$-$C_4$ alkyl-O—$R^{13}$, and $C_1$-$C_4$ alkyl-NR$^{13}$—C(O)R$^{13}$; and $X^2$ is selected from —NH—C(=O)-†, —C(=O)—NH-†, —NH—C(=S)-†, —C(=S)—NH-†, —NH—S(=O)-†, —S(=O)—NH-†, —S(=O)$_2$—NH-†, —NH—S(=O)$_2$-†, —NH—S(O)$_2$—NR$^{15}$-†, —NR$^{15}$—S(O)$_2$—NH-†, —NH—C(=O)O-†, —OC(=O)NH-†, —NH—C(=O)NR$^{15}$-†, —NR$^{15}$—C(=O)NH-†, —NH—NR$^{15}$-†, —NR$^{15}$—NH-†, —O—NH-†, —NH—O-†, —NH—C(=NR$^{15}$)-†, —C(=NR$^{15}$)—NH-†, —C(=O)—NH—CR$^{15}$R$^{16}$-†, —CR$^{15}$R$^{16}$—NH—C(O)-†, —NH—C(=S)—CR$^{15}$R$^{16}$-†, —CR$^{15}$R$^{16}$—C(=S)—NH-†, —NH—S(O)—CR$^{15}$R$^{16}$-†, —CR$^{15}$R$^{16}$—S(O)—NH-†, —NH—S(O)$_2$—CR$^{15}$R$^{16}$-†, —CR$^{15}$R$^{16}$—S(O)$_2$—NH-†, —NH—C(=O)—O—CR$^{15}$R$^{16}$-†, —CR$^{15}$R$^{16}$—O—C(=O)—NH-†, —NH—C(=O)—NR$^{15}$—CR$^{15}$R$^{16}$-†, —NH—C(=O)—CR$^{15}$R$^{16}$-†, and —CR$^{15}$R$^{16}$—NH—C(=O)—O-†;

wherein:

† represents where $X^1$ is bound to $R^{11}$; and each of $R^{15}$ and $R^{16}$ is independently selected from hydrogen, $C_1$-$C_4$ alkyl, —$CF_3$ and ($C_1$-$C_3$ alkyl)-$CF_3$.

Compounds of the invention, including novel compounds of the invention, can also be used in the methods described herein.

The compounds and salts thereof described herein also include their corresponding hydrates (e.g., hemihydrate, monohydrate, dihydrate, trihydrate, tetrahydrate) and solvates. Suitable solvents for preparation of solvates and hydrates can generally be selected by a skilled artisan.

The compounds and salts thereof can be present in amorphous or crystalline (including co-crystalline and polymorph) forms.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

Carbocyclic includes 5-7 membered monocyclic and 8-12 membered bicyclic rings wherein the monocyclic or bicyclic rings are selected from saturated, unsaturated and aromatic. A carbocycle is optionally substituted with one or more substituents such as halo, —C≡N, $C_1$-$C_3$ alkyl, $C_1$-$C_2$ fluoro-substituted alkyl, —O—($C_1$-$C_2$) fluoro-substituted alkyl, —O—($C_1$-$C_3$) alkyl, —S—($C_1$-$C_3$) alkyl, —S—($C_1$-$C_2$) fluoro-substituted alkyl, hydroxyl, amino, —NH—($C_1$-$C_3$) alkyl and —N—($C_1$-$C_3$)$_2$ alkyl. Exemplary carbocycles include cyclopentyl, cyclohexyl, cyclohexenyl, adamantyl, phenyl and naphthyl.

Heterocyclic includes 4-7 membered monocyclic and 8-12 membered bicyclic rings comprising one or more heteroatoms selected from, for example, N, O, and S atoms. In certain embodiments, the heterocyclic group is selected from saturated, unsaturated or aromatic. A heterocycle is optionally substituted with one or more substituents such as halo, —C≡N, $C_1$-$C_3$ alkyl, $C_1$-$C_2$ fluoro-substituted alkyl, —O—($C_1$-$C_2$) fluoro-substituted alkyl, —O—($C_1$-$C_3$) alkyl, —S—($C_1$-$C_3$) alkyl, —S—($C_1$-$C_2$) fluoro-substituted alkyl, hydroxyl, amino, —NH—($C_1$-$C_3$) alkyl and —N—($C_1$-$C_3$)$_2$ alkyl.

Monocyclic rings include 5-7 membered aryl or heteroaryl, 3-7 membered cycloalkyl, and 5-7 membered non-aromatic heterocyclyl. Monocyclic rings are optionally substituted with one or more substituents such as halo, cyano, lower alkoxy, lower alkyl, hydroxyl, amino, lower alkylamino and lower dialkylamino. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptanyl, azetidinyl, oxetanyl, thiiranyl, oxiranyl, aziridinyl, and thiomorpholinyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl.

Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Azabicyclo refers to a bicyclic molecule that contains a nitrogen atom in the ring skeleton. The two rings of the bicycle may be fused, at two mutually bonded atoms, e.g., indole, across a sequence of atoms, e.g., azabicyclo[2.2.1]heptane, or at a single atom, e.g., spirocycle.

Bridged azabicyclo refers to a bicyclic molecule that contains a nitrogen atom and two fused rings wherein the fusion occurs across a sequence of atoms, i.e., bridgehead atoms. Bridged bicyclo compounds comprise at least one bridge of one or more atoms connecting two bridgehead atoms.

Fluoro-substituted includes from one fluoro substituent up to per-fluoro-substitution. Exemplary fluoro-substituted $C_1$-$C_2$ alkyl includes —CFH, $CF_2H$, —$CF_3$, —$CH_2CH_2F$, —$CH_2CHF_2$, —$CHFCH_3$, and —$CF_2CHF_2$. Per-fluoro-substituted $C_1$-$C_2$ alkyl, for example, includes —$CF_3$ and —$CF_2CF_3$.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants. In certain embodiments, deuterated variants may be used for kinetic studies. One of ordinary skill in the art can select the sites at which such deuterium atoms are present.

Also included in the present invention are salts, particularly pharmaceutically acceptable salts, of the sirtuin-modulating compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

According to another embodiment, the present invention provides methods of producing the above-defined sirtuin-modulating compounds. The compounds may be synthesized using conventional techniques. Advantageously, these compounds are conveniently synthesized from readily available starting materials.

Synthetic chemistry transformations and methodologies useful in synthesizing the sirtuin-modulating compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

In an exemplary embodiment, a sirtuin-modulating compound may traverse the cytoplasmic membrane of a cell. For example, a compound may have a cell-permeability of at least about 20%, 50%, 75%, 80%, 90% or 95%.

Sirtuin-modulating compounds described herein may also have one or more of the following characteristics: the compound may be essentially non-toxic to a cell or subject; the sirtuin-modulating compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a sirtuin-modulating compound may be more stable in solution than resveratrol by at least a factor of about 50%, 2 fold, 5 fold, 10 fold, 30 fold, 50 fold or 100 fold; a sirtuin-modulating compound may promote deacetylation of the DNA repair factor Ku70; a sirtuin-modulating compound may promote deacetylation of RelA/p65; a compound may increase general turnover rates and enhance the sensitivity of cells to TNF-induced apoptosis.

In certain embodiments, a sirtuin-modulating compound does not have any substantial ability to inhibit a histone deacetylase (HDACs) class I, a HDAC class II, or HDACs I and II, at concentrations (e.g., in vivo) effective for modulating the deacetylase activity of the sirtuin. For instance, in preferred embodiments the sirtuin-modulating compound is a sirtuin-activating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, a sirtuin-modulating compound does not have any substantial ability to modulate sirtuin homologs. In one embodiment, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-activating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as *Candida, S. cerevisiae*, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as *Candida, S. cerevisiae*, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In one embodiment, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In one embodiment, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In one embodiment, a SIRT3 modulator does not have any substantial ability to modulate a SIRT1 protein.

In certain embodiments, a sirtuin-modulating compound may have a binding affinity for a sirtuin protein of about $10^{-9}$M, $10^{-10}$M, $10^{-11}$M, $10^{-12}$M or less. A sirtuin-modulating compound may reduce (activator) or increase (inhibitor) the apparent Km of a sirtuin protein for its substrate or NAD+ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an ED50 for modulating the deacetylase activity of a SIRT1 and/or SIRT3 protein of less than about 1 nM, less than about 10 nM, less than about 100 nM, less than about 1 μM, less than about 10 μM, less than about 100 μM, or from about 1-10 nM, from about 10-100 nM, from about 0.1-1 µM, from about 1-10 µM or from about 10-100 µM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-activating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an ED50 for modulating SIRT5 that is at least about 10 fold, 20 fold, 30 fold, 50 fold greater than that for modulating SIRT1 and/or SIRT3.

3. Exemplary Uses

In certain aspects, the invention provides methods for modulating the level and/or activity of a sirtuin protein and methods of use thereof.

In certain embodiments, the invention provides methods for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a sirtuin-modulating compound, e.g., a sirtuin-activating compound.

Without wishing to be bound by theory, it is believed that activators of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In one embodiment, a mixture of two or more sirtuin-modulating compounds may be administered to a subject in need thereof. In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid. In another embodiment, a sirtuin-modulating compound that decreases the level and/or activity of a sirtuin protein may be administered with one or more of the following compounds: nicotinamide (NAM), suramin; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8, 3',4'-hexahydroxyflavone), sirtinol; and splitomicin. In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the sirtuin modulating compound(s) and other therapeutic agent(s) are in separate vessels). When using separate formulations, the sirtuin-modulating compound may be administered at the same, intermittent, staggered, prior to, subsequent to, or combinations thereof, with the administration of another therapeutic agent.

In certain embodiments, methods for reducing, preventing or treating diseases or disorders using a sirtuin-modulating compound may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 and/or SIRT3 protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 and/or SIRT3 protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one embodiment, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods comprise contacting the cell with a sirtuin-activating compound.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one embodiment, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another embodiment, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In one embodiment, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In one embodiment, a sirtuin-modulating compound that increases the level and/or activity of a sirtuin protein may be administered as part of a combination therapeutic with another cardiovascular agent. In one embodiment, a sirtuin-modulating compound that increases the level and/or activity of a sirtuin protein may be administered as part of a combination therapeutic with an anti-arrhythmia agent. In another embodiment, a sirtuin-modulating compound that increases the level and/or activity of a sirtuin protein may be administered as part of a combination therapeutic with another cardiovascular agent.

Cell Death/Cancer

Sirtuin-modulating compounds that increase the level and/or activity of a sirtuin protein may be administered to subjects who have recently received or are likely to receive a dose of radiation or toxin. In one embodiment, the dose of radiation or toxin is received as part of a work-related or medical procedure, e.g., administered as a prophylactic measure. In another embodiment, the radiation or toxin exposure is received unintentionally. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress. Chemotherapeutic agents may be used by themselves with a sirtuin-modulating compound described herein as inducing cell death or reducing lifespan or increasing sensitivity to stress and/or in combination with other chemotherapeutics agents. In addition to conventional chemotherapeutics, the sirtuin-modulating compounds described herein may also be used with antisense RNA, RNAi or other polynucleotides to inhibit the expression of the cellular components that contribute to unwanted cellular proliferation.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with sirtuin-modulating compounds of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chromic inflammatory demyelinating polyneuropathy (CIDP), or symptoms associated therewith.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with sirtuin-modulating compounds that increase the level and/or activity of a sirtuin protein include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus.

In another embodiment, a sirtuin activating compound may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In one embodiment, apoptotic or necrotic cell death may be prevented. In still a further embodiment, ischemic-mediated damage, such as cytoxic edema or central nervous system tissue anoxemia, may be prevented. In each embodiment, the central nervous system cell may be a spinal cell or a brain cell.

Another aspect encompasses administrating a sirtuin activating compound to a subject to treat a central nervous system ischemic condition. A number of central nervous system ischemic conditions may be treated by the sirtuin activating compounds described herein. In one embodiment, the ischemic condition is a stroke that results in any type of ischemic central nervous system damage, such as apoptotic or necrotic cell death, cytoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, a sirtuin activating compound may be administered to reduce infarct size of the ischemic core following a central nervous system ischemic condition. Moreover, a sirtuin activating compound may also be beneficially administered to reduce the size of the ischemic penumbra or transitional zone following a central nervous system ischemic condition.

In one embodiment, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemo stasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemo stasis in a subject by administering a sirtuin-modulating compound that increases the level and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. Such methods may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compounds that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents.

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases, and/or inflammation associated with autoimmune diseases, such as arthritis, including rheumatoid arthritis, psoriatic arthritis, and ankylo sing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In one embodiment, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

In another embodiment, the invention provides a method for treating and/or preventing hyperlipidemia with reduced flushing side effects. In another representative embodiment, the method involves the use of sirtuin-modulating compounds that increase the level and/or activity of a sirtuin protein to reduce flushing side effects of raloxifene. In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, or a 5HT2 receptor antagonist.

In certain embodiments, sirtuin-modulating compounds that increase the level and/or activity of a sirtuin protein may be used as part of a treatment with a serotonin reuptake inhibitor (SRI) to reduce flushing. In still another representative embodiment, sirtuin-modulating compounds that increase the level and/or activity of a sirtuin protein may be used to reduce flushing side effects of chemotherapeutic agents, such as cyclophosphamide and tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g. Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g. *Candida* choroiditis, histoplasmosis), protozoal infections (e.g. toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, a drug that raises intraocular pressure such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment a therapeutic dosage of a sirtuin modulator disclosed herein.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In one embodiment, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder.

In one embodiment, a sirtuin modulator can be administered in conjunction with a therapy for reducing intraocular pressure. In another embodiment, a sirtuin modulator can be administered in conjunction with a therapy for treating and/or preventing glaucoma. In yet another embodiment, a sirtuin modulator can be administered in conjunction with a therapy for treating and/or preventing optic neuritis. In one embodiment, a sirtuin modulator can be administered in conjunction with a therapy for treating and/or preventing CMV Retinopathy. In another embodiment, a sirtuin modulator can be administered in conjunction with a therapy for treating and/or preventing multiple sclerosis.

Mitochondrial-Associated Diseases and Disorders

In certain embodiments, the invention provides methods for treating diseases or disorders that would benefit from increased mitochondrial activity. The methods involve administering to a subject in need thereof a therapeutically effective amount of a sirtuin activating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetic, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof one or more sirtuin activating compounds in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject a therapeutically effective amount of a sirtuin activating compound. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, sirtuin activating compounds may be used for reducing the rate of decline in muscular functional capacities and for improving muscular functional status in patients with muscular dystrophy.

In certain embodiments, sirtuin modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, sirtuin activating compounds may be useful for treating patients suffering from toxic damage to mitochondria, such as, toxic damage due to calcium accumulation, excitotoxicity, nitric oxide exposure, drug induced toxic damage, or hypoxia.

In certain embodiments, sirtuin activating compounds may be useful for treating diseases or disorders associated with mitochondrial deregulation.

Muscle Performance

In other embodiments, the invention provides methods for enhancing muscle performance by administering a therapeutically effective amount of a sirtuin activating compound. For example, sirtuin activating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of a sirtuin activating compound that increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides novel dietary compositions comprising sirtuin modulators, a method for their preparation, and a method of using the compositions for improvement of sports performance. Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases. In another embodiment, sirtuin-modulating compounds that increase the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In one embodiment, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance, and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, which may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bio-available to insect larvae, and not to plants.

At least in view of the link between reproduction and longevity, sirtuin-modulating compounds that increase the level and/or activity of a sirtuin protein can be applied to affect the reproduction of organisms such as insects, animals and microorganisms.

4. Assays

Yet other methods contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In one embodiment, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

Methods for identifying an agent that modulates, e.g., stimulates, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 µM to about 10 mM, preferably from about 10 µM to 1 mM, even more preferably from about 100 µM to 1 mM, such as about 200 µM. A preferred substrate is an acetylated lysine, e.g., ε-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 µM, preferably from about 0.1 to 10 µM, such as 1 µM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

5. Pharmaceutical Compositions

The sirtuin-modulating compounds described herein may be formulated in a conventional manner using one or more physiologically or pharmaceutically acceptable carriers or excipients. For example, sirtuin-modulating compounds and their pharmaceutically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In one embodiment, a sirtuin-modulating compound may be administered locally, at the site where the target cells are present, i.e., in a specific tissue, organ, or fluid (e.g., blood, cerebrospinal fluid, etc.).

Sirtuin-modulating compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), sirtuin-modulating compounds may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

Sirtuin-modulating compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Sirtuin-modulating compounds may also be formulated in rectal compositions such as suppositories or retention enemas, e.g., containing conventional suppository bases such as cocoa butter or other glycerides.

In addition to the formulations described previously, sirtuin-modulating compounds may also be formulated as a depot preparation. Such long acting formulations may be administered by implantation (for example subcutaneously or intramuscularly) or by intramuscular injection. Thus, for example, sirtuin-modulating compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well-known by a person skilled in the art. Liposomes can be formed from a variety of phospholipids, such as cholesterol, stearylamine of phosphatidylcholines. Liposomes being usable for the method of invention encompass all types of liposomes including, but not limited to, small unilamellar vesicles, large unilamellar vesicles and multilamellar vesicles.

Another way to produce a formulation, particularly a solution, of a sirtuin modulator such as resveratrol or a derivative thereof, is through the use of cyclodextrin. By cyclodextrin is meant α-, β-, or γ-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (including cosmetic preparations) may comprise from about 0.00001 to 100% such as from 0.001 to 10% or from 0.1% to 5% by weight of one or more sirtuin-modulating compounds described herein. In other embodiments, the pharmaceutical composition comprises: (i) 0.05 to 1000 mg of the compounds of the invention, or a pharmaceutically acceptable salt thereof, and (ii) 0.1 to 2 grams of one or more pharmaceutically acceptable excipients.

In one embodiment, a sirtuin-modulating compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Sirtuin-modulating compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

Sirtuin-modulating compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

Sirtuin-modulating compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Sirtuin-modulating compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

Sirtuin-modulating compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of a sirtuin-modulating compound, or by insertion of a sustained release device that releases a sirtuin-modulating compound. A sirtuin-modulating compound that increases the level and/or activity of a sirtuin protein may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

Sirtuin-modulating compounds described herein may be stored in oxygen free environment. For example, resveratrol or analog thereof can be prepared in an airtight capsule for oral administration, such as Capsugel from Pfizer, Inc.

Cells, e.g., treated ex vivo with a sirtuin-modulating compound, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of sirtuin-modulating compounds can be determined by standard pharmaceutical procedures in cell cultures or experimental animals. The $LD_{50}$ is the dose lethal to 50% of the population. The ED50 is the dose therapeutically effective in 50% of the population. The dose ratio between toxic and therapeutic effects ($LD_{50}/ED_{50}$) is the therapeutic index. Sirtuin-modulating compounds that exhibit large therapeutic indexes are preferred. While sirtuin-modulating compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. Kits

Also provided herein are kits, e.g., kits for therapeutic purposes or kits for modulating the lifespan of cells or modulating apoptosis. A kit may comprise one or more sirtuin-modulating compounds, e.g., in premeasured doses. A kit may optionally comprise devices for contacting cells with the compounds and instructions for use. Devices include syringes, stents and other devices for introducing a sirtuin-modulating compound into a subject (e.g., the blood vessel of a subject) or applying it to the skin of a subject.

In yet another embodiment, the invention provides a composition of matter comprising a sirtuin modulator of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The agent and the sirtuin modulator are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a sirtuin modulator of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Synthesis of N-(4-oxo-2-(3-(trifluoromethyl)phenyl)-4H-chromen-8-yl)thiazole-4-carboxamide (Compound 204)

Step 1. Preparation of 8-nitro-2-(3-(trifluoromethyl)phenyl)-4H-chromen-4-one (2)

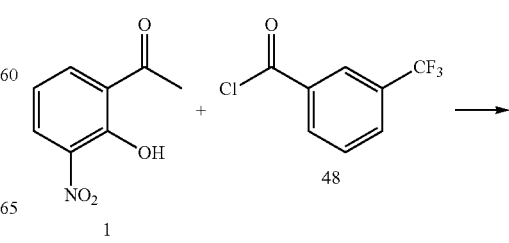

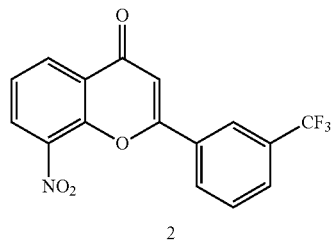

2

1-(2-Hydroxy-3-nitrophenyl)ethanone 1 (1.2 g, 6.61 mmol) was taken up in 20 mL of pyridine along with 3-trifluoromethylbenzoyl chloride 48 (1.2 mL, 7.9 mmol) and DBU (2.9 mL, 14.5 mmol). The reaction mixture was stirred at 80° C. for 18 h. The reaction mixture was cooled to room temperature and concentrated under reduced pressure. The resulting residue was diluted with EtOAc and washed with dilute 1 N HCl. The organic layer was dried ($Na_2SO_4$) and concentrated under reduced pressure. Purification by chromatography (1:1 pentane/EtOAc) afforded 300 mg of 2. MS (ESI) calcd for $C_{16}H_8F_3NO_4$: 335.04. found: 336 [M+H].

Step 2. Preparation of 8-amino-2-(3-(trifluoromethyl)phenyl)-4H-chromen-4-one (178)

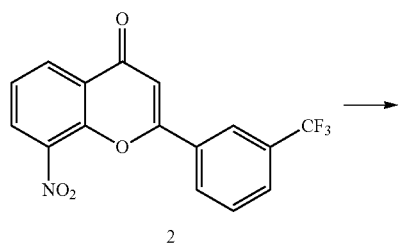

2

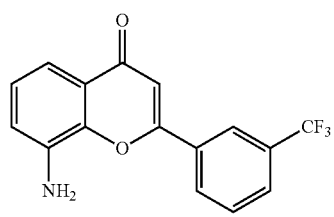

178

8-nitro-2-(3-(trifluoromethyl)phenyl)-4H-chromen-4-one 2 (300 mg, 0.90 mmol) was taken up in 10 mL of MeOH. Sodium hydro sulfide hydrate (250 mg, 4.5 mol) was added as a solution in 4 mL of $H_2O$. The reaction mixture was stirred under reflux for 45 min. It was then cooled to room temperature and concentrated under reduced pressure. The resulting aqueous mixture was extracted with EtOAc. The combined organic layers were dried ($Na_2SO_4$) and concentrated under reduced pressure to afford 240 mg of 178. MS (ESI) calcd for $C_{16}H_{10}F_3NO_2$: 305.07. found: 306 [M+H].

Step 3. Preparation of N-(4-oxo-2-(3-(trifluoromethyl)phenyl)-4H-chromen-8-yl)thiazole-4-carboxamide

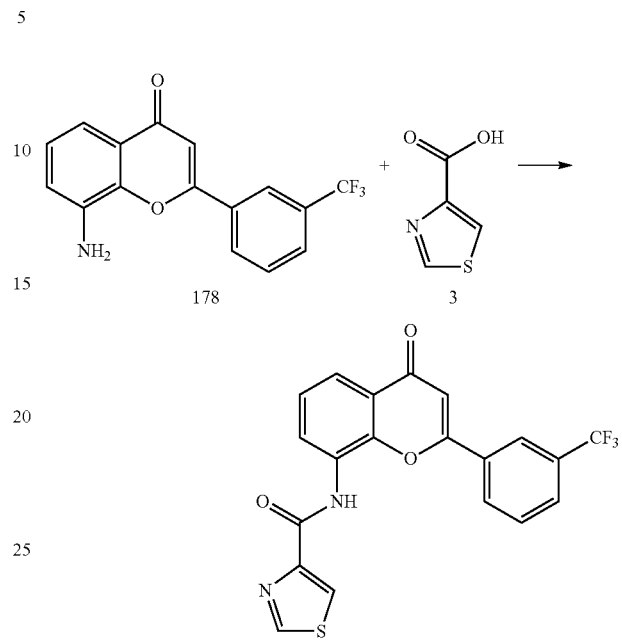

Compound 204

8-amino-2-(3-(trifluoromethyl)phenyl)-4H-chromen-4-one (178) (70 mg, 0.23 mmol) was taken up in 2 mL of DMF along with thiazole-4-carboxylic acid 3 (30 mg, 0.23 mmol), HATU (175 mg, 0.46 mmol) and DIEA (80 μL, 0.46 mmol). The reaction mixture was stirred at room temperature for 18 h. It was then diluted with 5 mL of $H_2O$. The resulting solids were collected by filtration, washed successively with a solution of dilute $NaHCO_3$/MeOH (1:1), aqueous MeOH, dilute 1 N HCl/MeOH (1:1), aqueous MeOH, and then pure MeOH. After drying under high vacuum, 28 mg of Compound 204 was obtained as an off-white solid. MS (ESI) calcd for $C_{20}H_{11}F_3N_2O_3S$: 416.04. found: 417 [M+H].

Example 2

Synthesis of N-(4-oxo-2-(pyridin-3-yl)-4H-chromen-8-yl)thiazole-4-carboxamide (Compound 215)

Step 1. Preparation of 2-acetyl-6-nitrophenyl nicotinate (5)

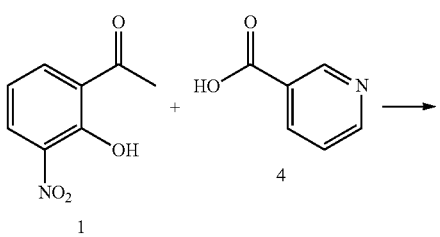

1      4

75 -continued

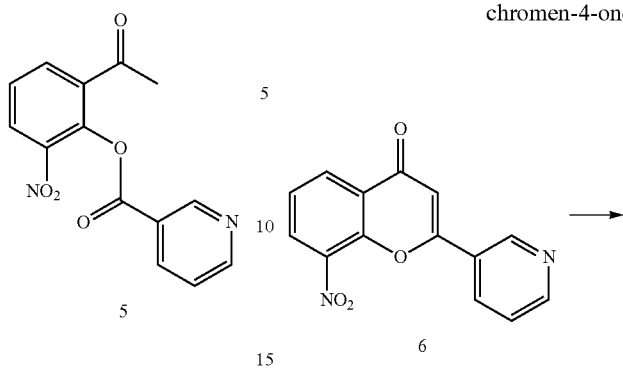

5

A mixture of 1-(2-Hydroxy-3-nitrophenyl)ethanone 1 (1.0 g, 5.5 mmol), nicotinic acid 4 (0.8 g, 5.8 mmol), DCC (2.4 g, 11.6 mmol) and DMAP (0.7 g, 5.8 mmol) in $CH_2Cl_2$ (30 mL) was stirred at room temperature for 12 hours. After cooling to 0° C., the precipitated dicyclohexyl urea was removed by filtration and the filtrate concentrated. The crude residue was purified by flash chromatography eluting with Pentane/EtOAc (10:1) to give 5 (1.3 g, 81% yield).

Step 2. Preparation of 8-nitro-2-(pyridin-3-yl)-4H-chromen-4-one (6)

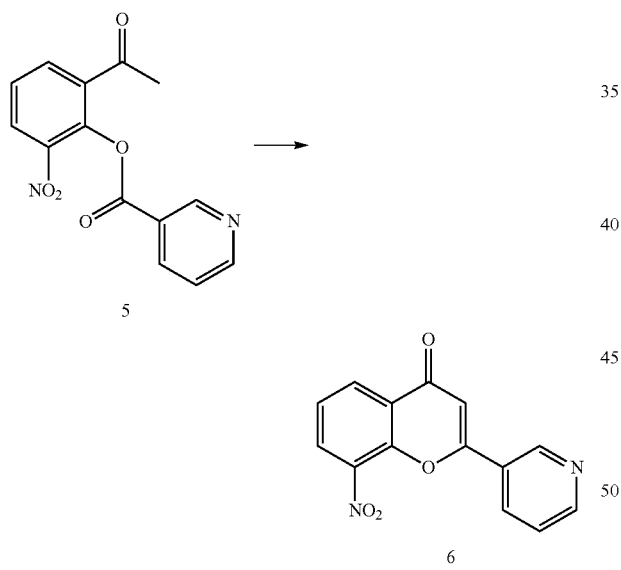

2-acetyl-6-nitrophenyl nicotinate 5 (1.3 g, 4.4 mmol) was dissolved in pyridine (10 mL) and heated to 50° C. Finely powdered KOH (3.4 g, 6.1 mmol) was added in small portions. After cooling to room temperature the reaction mixture was concentrated to dryness. Concentrated $H_2SO_4$ (0.4 g, 4.4 mmol) and AcOH (3 mL) was added and the mixture was heated to 80° C. for 2 h. The reaction mixture was concentrated to dryness and the crude residue was purified by flash chromatography eluting with Pentane/EtOAc (5:1) to give 6 (410 mg, 35% yield).

76

Step 3. Preparation of 8-amino-2-(pyridin-3-yl)-4H-chromen-4-one (7)

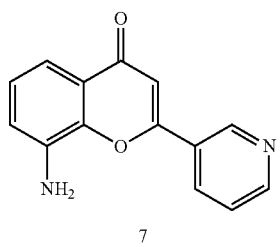

8-amino-2-(pyridin-3-yl)-4H-chromen-4-one 7 was prepared in 78% yield by a procedure similar to that used in Example 1, step 2, to produce 178.

Step 4. Preparation of N-(4-oxo-2-(pyridin-3-yl)-4H-chromen-8-yl)thiazole-4-carboxamide (Compound 215)

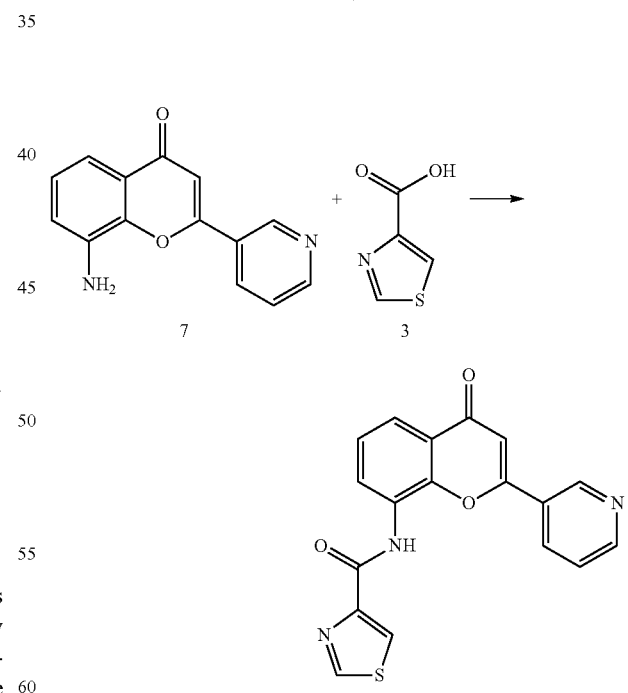

Compound 215

Compound 215 was prepared in 23% yield by a procedure similar to that used in Example 1, step 3, to produce Compound 204.

Example 3

Synthesis of N-(4-oxo-2-(2-(trifluoromethyl)phenyl)-4H-chromen-8-yl)thiazole-4-carboxamide (Compound 227)

Step 1. Preparation of (E)-1-(2-hydroxy-3-nitrophenyl)-3-(2-(trifluoromethyl)phenyl)prop-2-en-1-one (9)

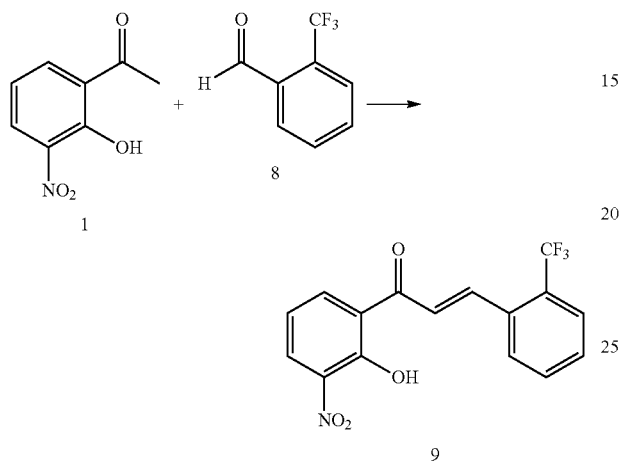

A solution of 1-(2-Hydroxy-3-nitrophenyl)ethanone 1 (788 mg, 4.4 mmol), 2-(trifluoromethyl)benzaldehyde 8 (1.1 g, 6.5 mmol) and 25% aq KOH (90 mL) in EtOH (90 mL) was stirred for 12 h at room temperature. The reaction mixture was poured into ice-water and the pH was adjusted to 2 using conc. HCl. The resulting precipitate was collected by filtration, rinsed with H₂O and dried under vacuum to give 9 as a yellow solid (1.4 g, 95% yield).

Step 2. Preparation of 8-nitro-2-(2-(trifluoromethyl)phenyl)-4H-chromen-4-one (10)

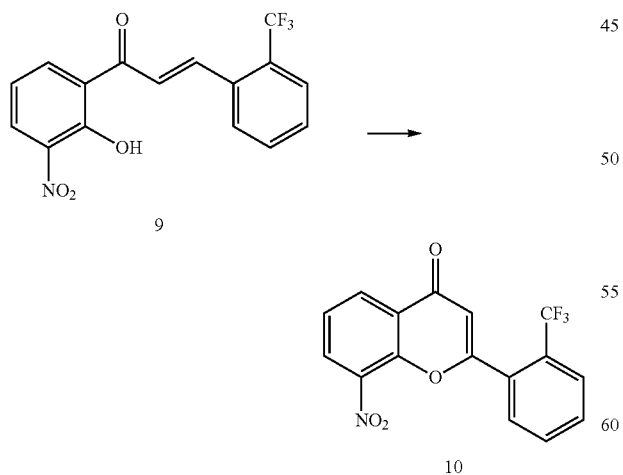

A solution of (E)-1-(2-hydroxy-3-nitrophenyl)-3-(2-(trifluoromethyl)phenyl)prop-2-en-1-one 9 (1.4 g, 4.2 mmol) and SeO₂ (1.4 g, 12.5 mmol) in DMSO/dioxane (35 ml, 1:15) was heated at reflux for 12 h. After cooling to room temperature, the reaction mixture was passed through a filter and the filtrate was concentrated to dryness. The crude residue was suspended in H₂O and collected by filtration to give 10 as a yellow solid (1.3 g, 92% yield).

Step 3. Preparation of 8-amino-2-(2-(trifluoromethyl)phenyl)-4H-chromen-4-one

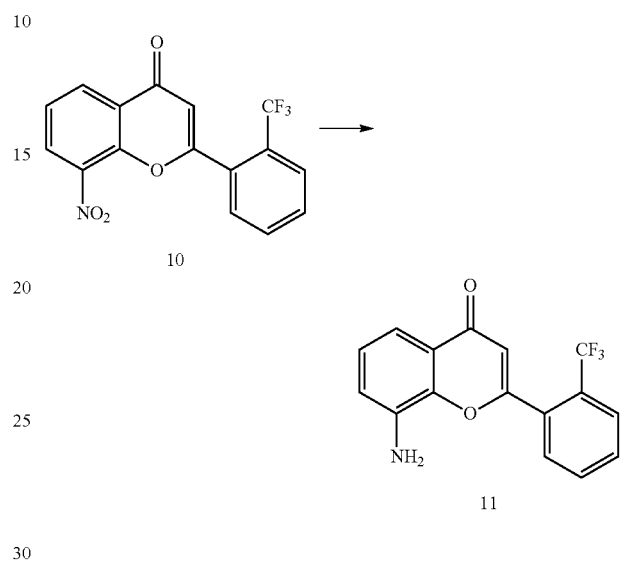

Compound 11 was prepared in 58% yield a by a procedure similar to that used in Example 1, step 2, to produce 178.

Step 4. Preparation of N-(4-oxo-2-(2-(trifluoromethyl)phenyl)-4H-chromen-8-yl)thiazole-4-carboxamide

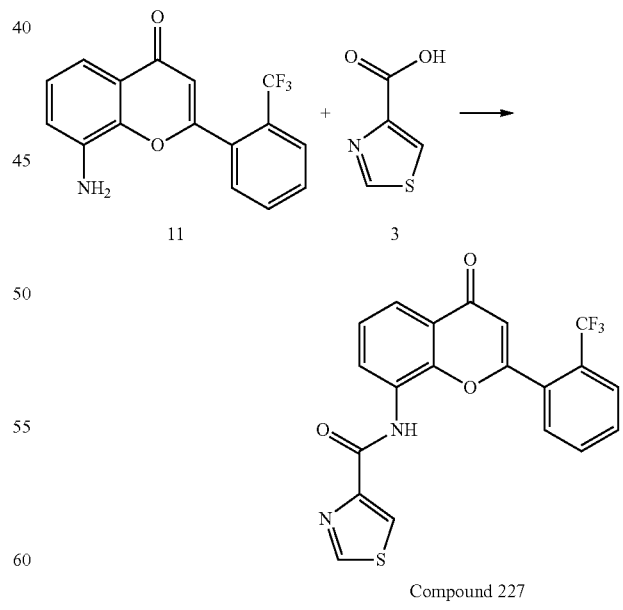

Compound 227 was prepared in 60% yield by a procedure similar to that used in Example 1, step 3, to produce Compound 204. MS (ESI) calcd for $C_{20}H_{11}F_3N_2O_3S$: 416.04. found: 417 [M+H].

Example 4

Synthesis of N-(4-oxo-2-(2-(trifluoromethyl)phenyl)-4H-chromen-8-yl)pyridine-3-sulfonamide (Compound 326)

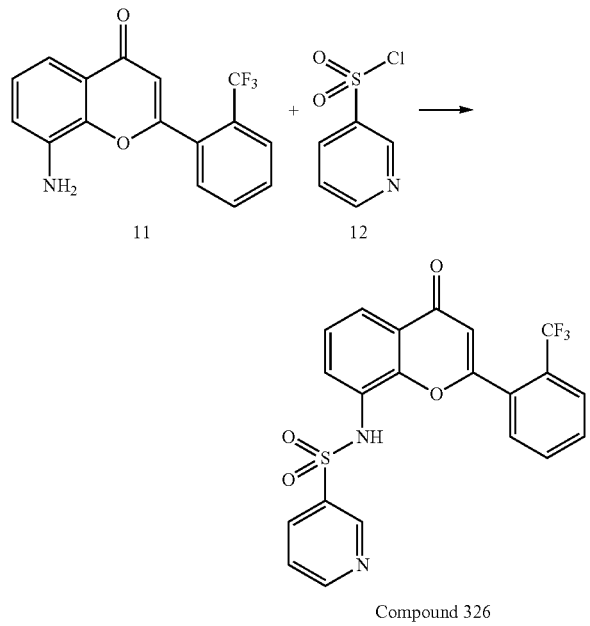

Compound 326

Pyridine-3-sulfonyl chloride hydrochloride 12 (280 mg, 1.3 mmol) was added to a solution of 8-amino-2-(2-(trifluoromethyl)phenyl)-4H-chromen-4-one 11 (100 mg, 0.328 mmol) in pyridine (5 mL). The reaction mixture was heated at 80° C. for 12 h. The pyridine was removed en vacuo. The residue was taken up in $CH_2Cl_2$, washed with sat. aq $NaHCO_3$, dried ($MgSO_4$) and concentrated. The crude residue was purified by MPLC eluting with $CH_2Cl_2$/MeOH (0-10%) followed by recrystallization from $CH_3CN$ to give Compound 326 (46 mg, 31% yield). MS (ESI) calcd for $C_{21}H_{13}F_3N_2O_4S$: 446.1. found: 447 [M+H].

Example 5

Synthesis of 5-oxo-N-(4-oxo-2-(2-(trifluoromethyl)phenyl)-4H-chromen-8-yl)pyrrolidine-2-carboxamide (Compound 313)

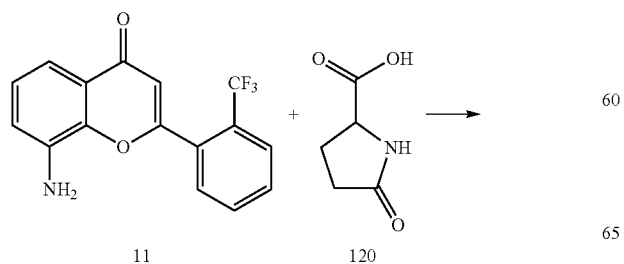

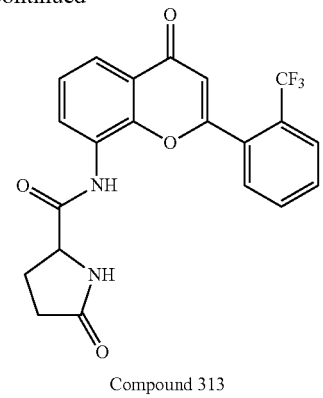

Compound 313

Thionylchloride (236 mg, 2.0 mmol) was added to a solution of 5-oxopyrrolidine-2-carboxylic acid 120 (170 mg, 1.32 mmol) in THF (5 mL) at 0° C. DMF (1 drop) was added and the solution was allowed to warm to room temperature for 2 h then cooled to 0° C. A solution of 8-amino-2-(2-(trifluoromethyl)phenyl)-4H-chromen-4-one 11 (100 mg, 0.33 mmol) and pyridine (0.5 mL) in THF (1 mL) was added and the reaction mixture was allowed to warm to room temperature and stirred for 2 h. The reaction mixture was concentrated to dryness, dissolved in EtOAc, washed with sat. aq $NaHCO_3$, brine, and dried ($Na_2SO_4$). The crude residue was purified by preparative TLC eluting with EtOAc to give Compound 313. MS (ESI) calcd for $C_{21}H_{15}F_3N_2O_4$: 416.1. found: 417 [M+H].

Example 6

Synthesis of N-(2-(2-(methylsulfonyl)phenyl)-4-oxo-4H-chromen-8-yl)thiazole-4-carboxamide (Compound 241)

Step 1. Preparation of (E)-1-(2-hydroxy-3-nitrophenyl)-3-(2-(methylthio)phenyl)prop-2-en-1-one (15)

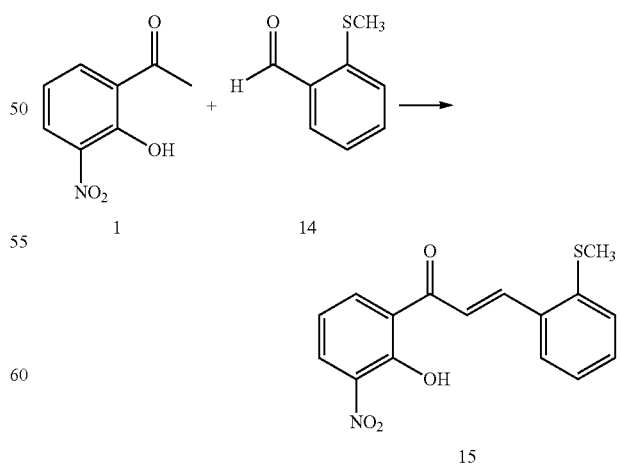

(E)-1-(2-hydroxy-3-nitrophenyl)-3-(2-(methylthio)phenyl)prop-2-en-1-one 15 was prepared in 100% yield by a procedure similar to that used in Example 3, step 1, to produce (E)-1-(2-hydroxy-3-nitrophenyl)-3-(2-(trifluoromethyl)phenyl)prop-2-en-1-one 9.

Step 2. Preparation of (E)-1-(2-hydroxy-3-nitrophenyl)-3-(2-(methylsulfonyl)phenyl)prop-2-en-1-one (16)

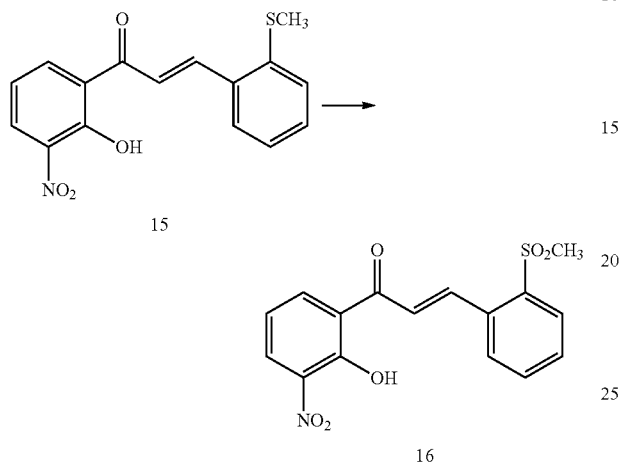

A solution of OXONE (3.7 g, 6 mmol) in H$_2$O (15 ml) was added drop wise to a solution of (E)-1-(2-hydroxy-3-nitrophenyl)-3-(2-(methylthio)phenyl)prop-2-en-1-one 15 (315 mg, 1.0 mmol) in THF/MeOH (35 mL, 1:1) at room temperature. The reaction mixture was stirred for 12 h. The volatiles were removed under reduced pressure and the resulting precipitate was collected by filtration, rinsed with H$_2$O and dried under vacuum. The crude residue was purified by flash chromatography eluting with CH$_2$Cl$_2$/MeOH (0-1%) to give 16 as a yellow solid (200 mg, yield 58%).

Step 3. Preparation of 2-(2-(methylsulfonyl)phenyl)-8-nitro-4H-chromen-4-one (17)

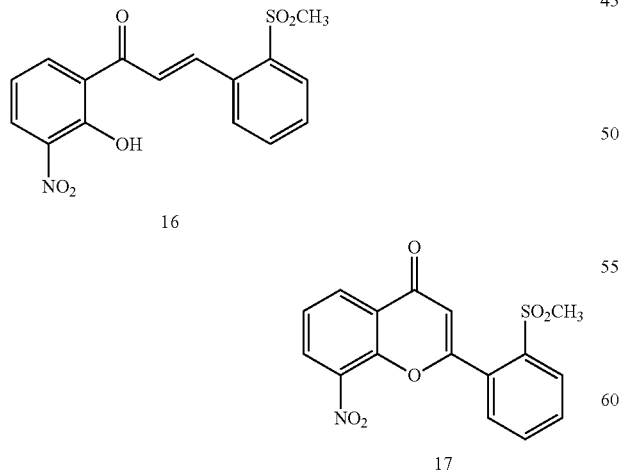

2-(2-(methylsulfonyl)phenyl)-8-nitro-4H-chromen-4-one 17 was prepared in 45% yield by a procedure similar to that used in Example 4, step 2, to produce 10.

Step 4. Preparation of 8-amino-2-(2-(methylsulfonyl)phenyl)-4H-chromen-4-one (18)

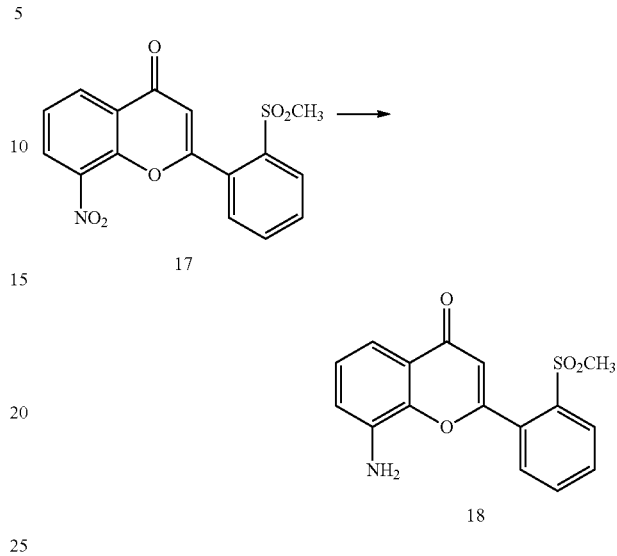

8-amino-2-(2-(methylsulfonyl)phenyl)-4H-chromen-4-one 18 was prepared in 93% yield by a procedure similar to that used in Example 1, step 2, to produce 178.

Step 5. Preparation of N-(2-(2-(methylsulfonyl)phenyl)-4-oxo-4H-chromen-8-yl)thiazole-4-carboxamide (Compound 241)

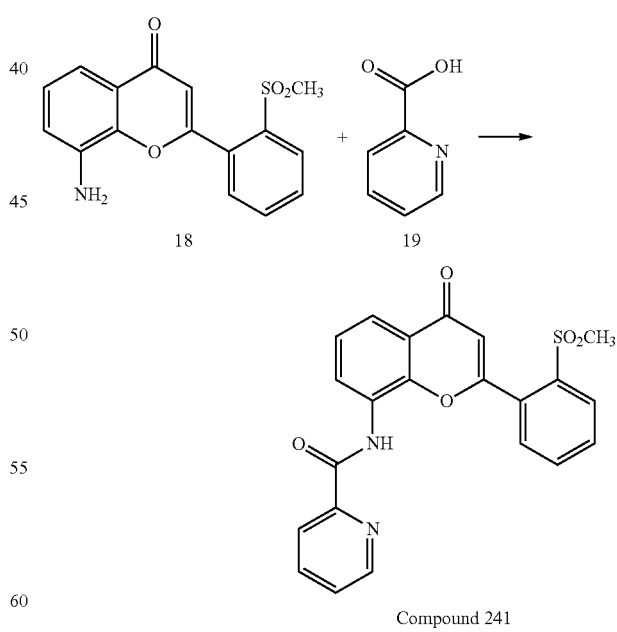

Compound 241 was prepared in 26% yield by a procedure similar to that used in Example 1, step 3, to produce N-(4-oxo-2-(3-(trifluoromethyl)phenyl)-4H-chromen-8-yl)thiazole-4-carboxamide Compound 204.

Example 7

Synthesis of N-(4-oxo-2-o-tolyl-4H-chromen-8-yl)pyrazine-2-carboxamide (Compound 273)

Step 1. Preparation of (E)-1-(2-hydroxy-3-nitrophenyl)-3-o-tolylprop-2-en-1-one

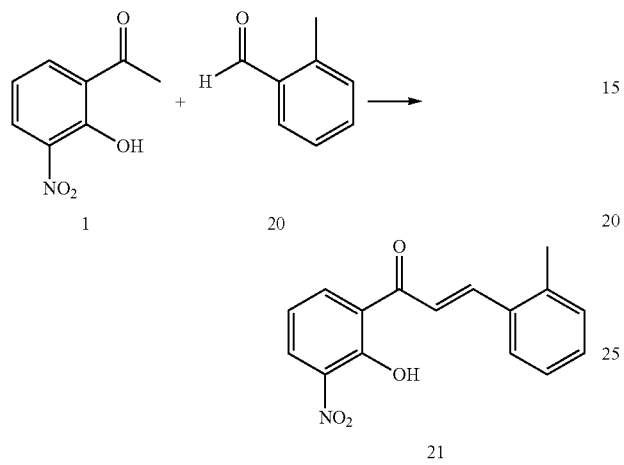

(E)-1-(2-hydroxy-3-nitrophenyl)-3-o-tolylprop-2-en-1-one 21 was prepared in 88% yield by a procedure similar to that used in Example 3, step 1, to produce (E)-1-(2-hydroxy-3-nitrophenyl)-3-(2-(trifluoromethyl)phenyl)prop-2-en-1-one 9.

Step 2. Preparation of 8-nitro-2-o-tolyl-4H-chromen-4-one (22)

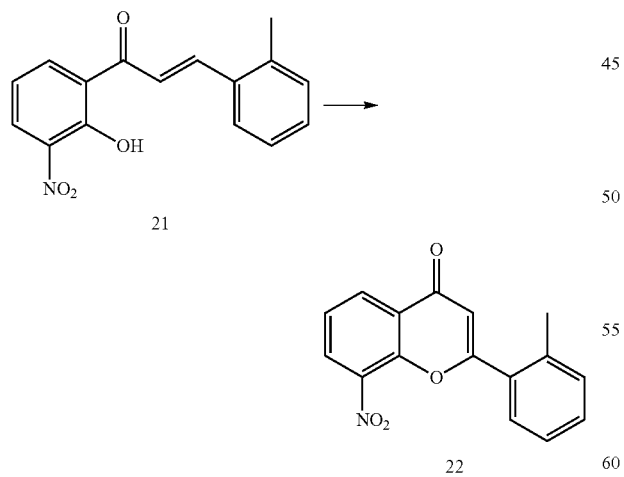

A mixture of (E)-1-(2-hydroxy-3-nitrophenyl)-3-o-tolylprop-2-en-1-one 21 (250 mg, 0.88 mmol), $I_2$ (471 mg, 1.86 mmol), DMSO (0.5 ml) and 1,4-dioxane (10 ml) was heated at reflux for 5 h. The reaction mixture was concentrated and $H_2O$ was added. The resulting precipitate was collected by filtration, rinsed with pentane/EtOAc (1:1) and dried under vacuum to give 22 as a yellow solid.

Step 3. Preparation of 8-amino-2-o-tolyl-4H-chromen-4-one (23)

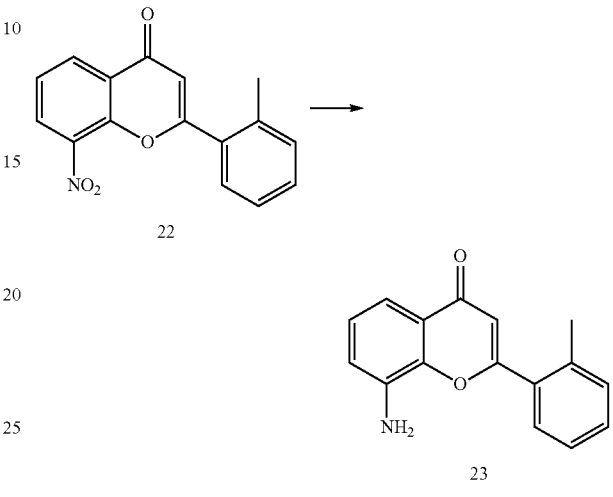

8-amino-2-o-tolyl-4H-chromen-4-one 23 was prepared in 40% yield over two steps by a procedure similar to that used in Example 1, step 2, to produce 178.

Step 4. Preparation of N-(4-oxo-2-o-tolyl-4H-chromen-8-yl)pyrazine-2-carboxamide (Compound 273)

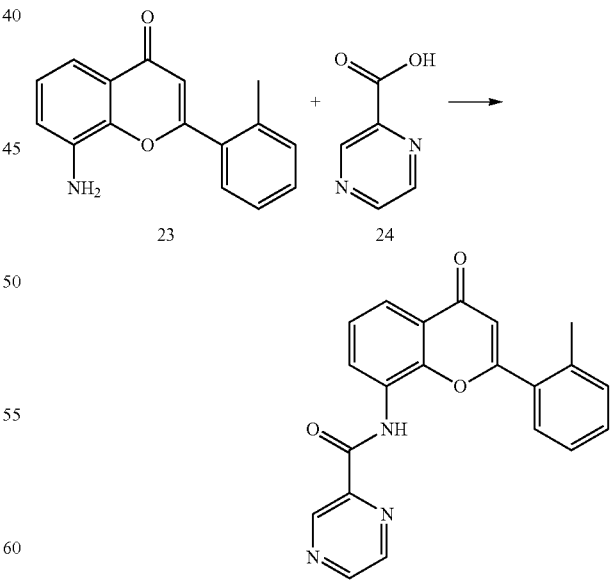

Compound 273

Compound 273 was prepared in 53% yield by a procedure similar to that used in Example 1, step 3, to produce Compound 204.

Example 8

Synthesis of N-(4-oxo-2-(2-(trifluoromethyl)pyridin-3-yl)-4H-chromen-8-yl)pyrazine-2-carboxamide (Compound 306)

Step 1. Preparation of 1-(2-hydroxy-3-nitrophenyl)-3-(2-(trifluoromethyl)pyridin-3-yl)propane-1,3-dione (26)

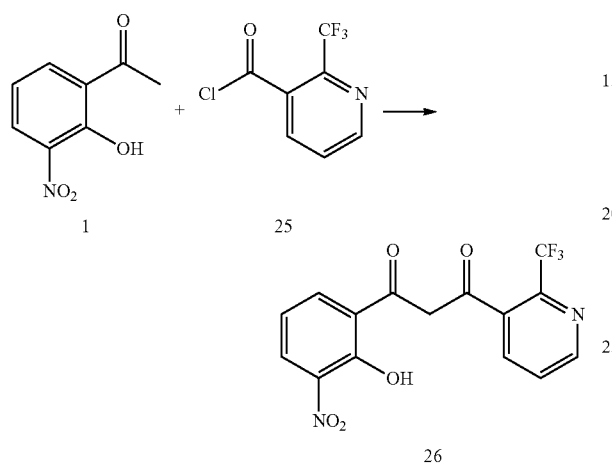

DBU (334 mg, 2.2 mmol) was added to a solution of 1-(2-Hydroxy-3-nitrophenyl)ethanone 1 (181 mg, 1 mmol) and 2-(trifluoromethyl)pyridine-3-carbonyl chloride 25 (1.1 mmol) in pyridine (3 ml). The mixture was stirred at 70° C. for 12 h, poured into 2N HCl (20 ml) and extracted with EtOAc. The organic layers were dried over $Na_2SO_4$, concentrated and purified by preparative TLC ($CH_2Cl_2$/EtOAc, 10:1) to give 26 as a yellow solid (135 mg, 38% yield).

Step 2. Preparation of 8-nitro-2-(2-(trifluoromethyl)pyridin-3-yl)-4H-chromen-4-one (27)

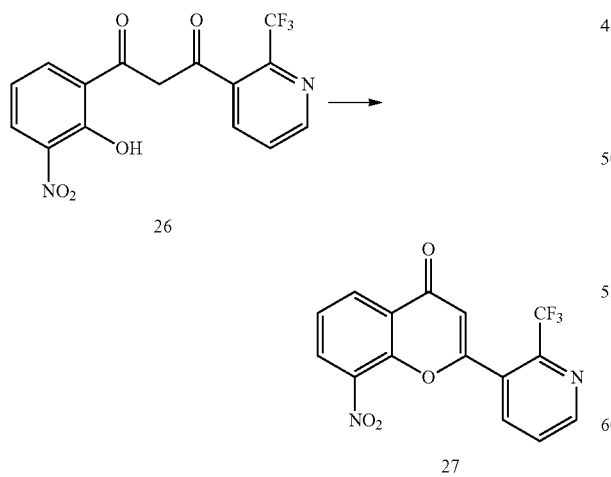

A mixture of 1-(2-hydroxy-3-nitrophenyl)-3-(2-(trifluoromethyl)pyridin-3-yl)propane-1,3-dione 26 (135 mg, 0.38 mmol), conc. HCl (0.2 ml) and AcOH (5 ml) was stirred at 100° C. for 3.5 h. The reaction mixture was concentrated and sat. aq $Na_2CO_3$ was added. The resulting solid was collected by filtration to give 27 as a yellow solid, which was used for the next step without other treatment.

Step 3. Preparation of 8-amino-2-(2-(trifluoromethyl)pyridin-3-yl)-4H-chromen-4-one (28)

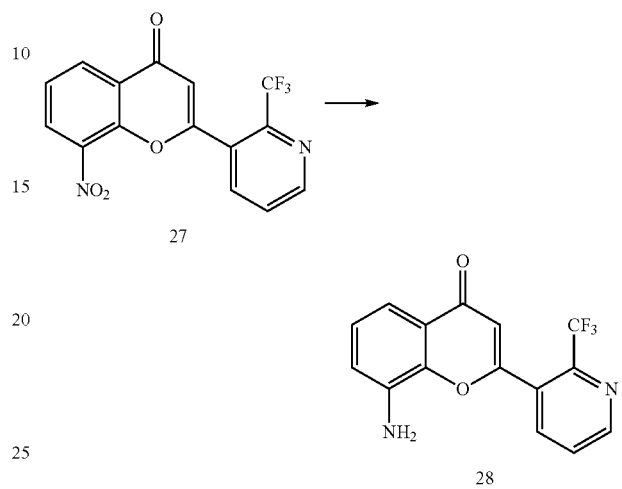

A mixture of 8-nitro-2-(2-(trifluoromethyl)pyridin-3-yl)-4H-chromen-4-one 27 (118 mg, 0.38 mmol), Fe (96 mg, 1.7 mmol), sat. aq $NH_4Cl$ (7 mL) and MeOH (14 mL) was stirred at 90° C. for 2 h. After cooling to room temperature the reaction mixture was poured into EtOAc and the layers separated. The organic layer was dried ($MgSO_4$) and concentrate to give 28 as a yellow solid (90 mg, 77% yield over two steps).

Step 4. Preparation of N-(4-oxo-2-(2-(trifluoromethyl)pyridin-3-yl)-4H-chromen-8-yl)pyrazine-2-carboxamide (Compound 306)

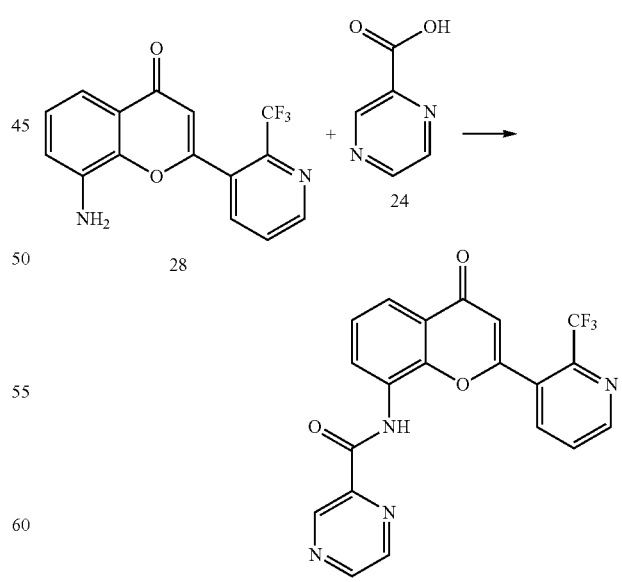

Compound 306

Compound 306 was prepared in 28% yield by a procedure similar to that used in Example 1, step 3, to produce Compound 204.

Example 9

Synthesis of 4-oxo-N-(pyridin-3-yl)-2-(3-(trifluoromethyl)phenyl)-4H-chromene-8-carboxamide (Compound 224)

Step 1. Preparation of 2-acetoxy-5-bromobenzoic acid (30)

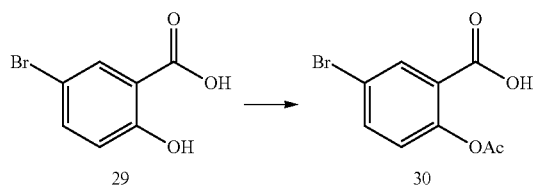 [SMILES: O=C(O)c1cc(Br)ccc1O ; CC(=O)Oc1ccc(Br)cc1C(=O)O]

To a well-stirred mixture of 5-bromosalicylic acid 29 (200 g, 0.92 mol) and acetic anhydride (210 mL) was added concentrated $H_2SO_4$ (0.5 mL). After a few minutes the reaction mixture solidified and was suspended in $H_2O$ (1 L). The solid was collected by filtration and washed with $H_2O$. The white solid was dissolved in ethyl acetate (3 L), washed with brine, dried ($Na_2SO_4$) and concentrated to give 30 (210 g, 88% yield).

Step 2. Preparation of 3-acetyl-5-bromo-2-hydroxybenzoic acid (31)

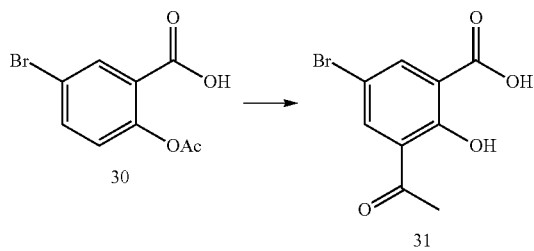

2-acetoxy-5-bromobenzoic acid 30 (100 g, 0.39 mol), and $AlCl_3$ (159 g, 1.20 mol) were mixed in a 3 L three-necked flask and heated to 160° C. under mechanical stirring. After 3 h, the reaction mixture was cooled to room temperature, crushed in a mortar and poured onto 800 g ice containing concentrated HCl (200 mL). The slurry was extracted with ethyl acetate, washed with 1 N HCl, brine, dried ($Na_2SO_4$) and concentrated. The crude residue was washed with dichloromethane to give 31 (50 g, 50% yield).

Step 3. Preparation of 3-acetyl-2-hydroxybenzoic acid (32)

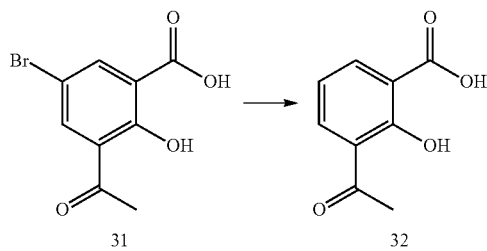

3-acetyl-5-bromo-2-hydroxybenzoic acid 31 (50 g, 0.19 mol) was dissolved in 250 mL ethanol. After addition of 5.0 g 10% Pd/C the reaction mixture was hydrogenated under 15 atm $H_2$-pressure at room temperature for 6 h. The catalyst was filtered and the solvent was evaporated. The residue was poured into $H_2O$ and extracted with $CH_2Cl_2$. The combined organic phase was dried and the solvent was removed to give 32 (28 g, 85% yield)

Step 4. Preparation of (E)-2-hydroxy-3-(3-(3-(trifluoromethyl)phenyl)acryloyl)benzoic acid (34)

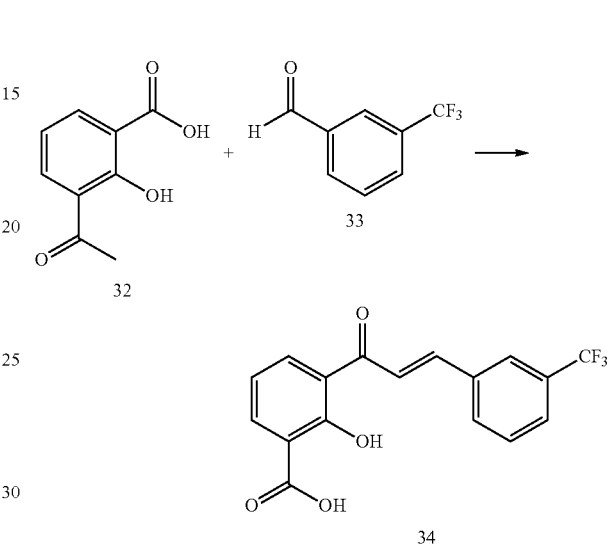

3-acetyl-2-hydroxybenzoic acid 32 (0.9 g, 5 mmol) and 3-(trifluoromethyl)benzaldehyde 33 (0.96 g, 5.5 mmol) were dissolved in 100 mL ethanol. After addition of the same volume of 25% aq KOH, the reaction mixture was stirred for 24 h. The mixture was poured into ice-water and the PH was adjusted to 2 with conc. HCl. The precipitate was filtered, washed with $H_2O$ and dried to give 34 (0.8 g, 47% yield)

Step 5. Preparation of 4-oxo-2-(3-(trifluoromethyl)phenyl)-4H-chromene-8-carboxylic acid (35)

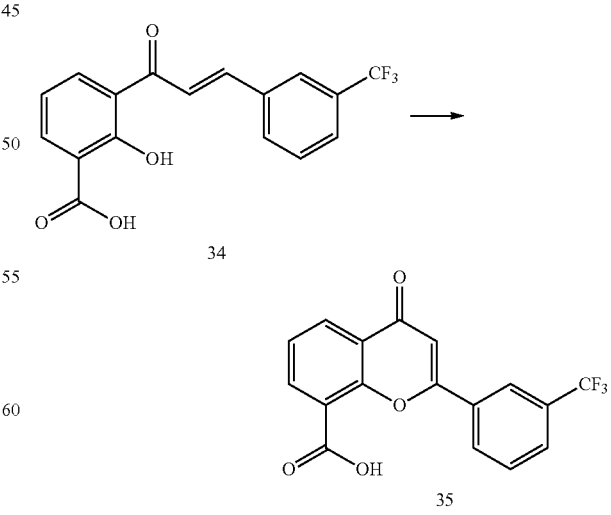

A mixture of (E)-2-hydroxy-3-(3-(3-(trifluoromethyl)phenyl)acryloyl)benzoic acid 34 (0.8 g, 2.4 mmol), $SeO_2$ (0.79 g, 7.1 mmol) and DMSO (5 mL) in dioxane (150 mL) was heated at reflux for 1 h. The black solid was filtered and the dioxane was evaporated. The remaining oil was suspended in H₂O, filtered and dried to give 35 (0.56 g, 76% yield).

Step 6. Preparation of 4-oxo-N-(pyridin-3-yl)-2-(3-(trifluoromethyl)phenyl)-4H-chromene-8-carboxamide (Compound 224)

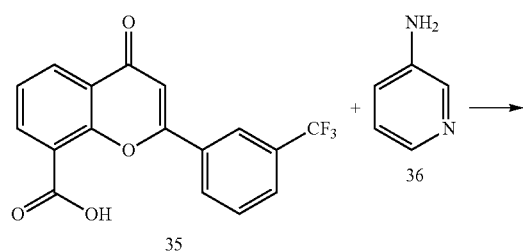

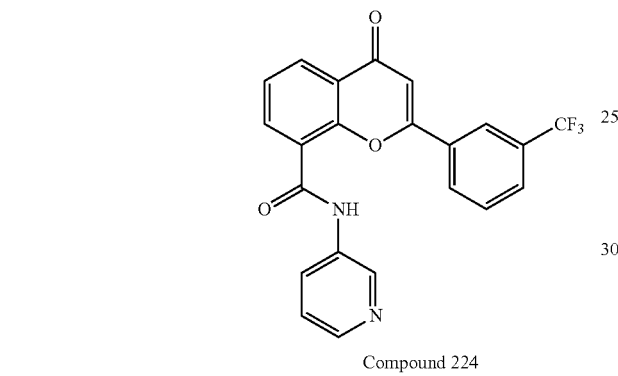

Compound 224

A mixture of 4-oxo-2-(3-(trifluoromethyl)phenyl)-4H-chromene-8-carboxylic acid 35 (0.5 g, 1.5 mmol), 3-aminopyridine 36 (0.28 g, 3 mmol), HATU (1.14 g, 3 mmol) and DIPEA (0.78 g, 6 mmol) in DMF (4 mL) was stirred at room temperature for 12 h. The reaction mixture was filtered and the solid was washed with H₂O and dried under vacuum to give Compound 224 as a yellow solid (0.13 g, 23% yield). MS (ESI) calcd for $C_{22}H_{13}F_3N_2O_3$: 410.09. found: 411 [M+H].

Example 10

Synthesis of 4-oxo-N-(6-(pyrrolidin-1-ylmethyl)pyridin-2-yl)-2-(3-(trifluoromethyl)phenyl)-4H-chromene-8-carboxamide (Compound 243)

Step 1. Preparation of 4-oxo-2-(3-(trifluoromethyl)phenyl)-4H-chromene-8-carbonyl chloride (37)

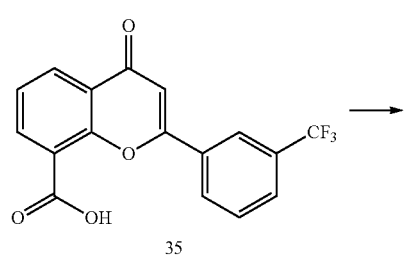

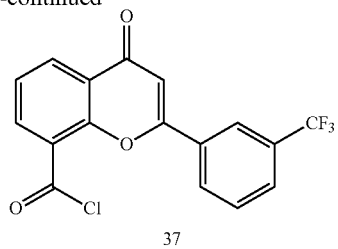

Oxallylchloride (285 mg, 2.24 mmol) was added to a solution of 4-oxo-2-(3-(trifluoromethyl)phenyl)-4H-chromene-8-carboxylic acid 35 (250 mg, 0.75 mmol) in CH₂Cl₂ (15 mL) followed by DMF (1 drop). The reaction mixture was stirred at room temperature for 12 h. The volatiles were concentrated and the crude residue was dissolved in CH₂Cl₂. The solvent was evaporated and the crude product dried under vacuum and used without further purification.

Step 2. Preparation of 4-oxo-N-(6-(pyrrolidin-1-ylmethyl)pyridin-2-yl)-2-(3-(trifluoromethyl)phenyl)-4H-chromene-8-carboxamide (Compound 243)

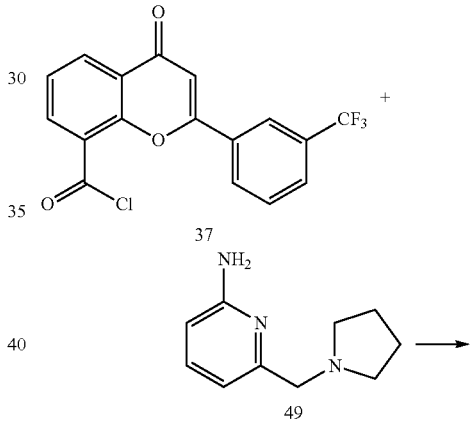

Compound 243

DIPEA (125 mL, 0.705 mmol) was added to a solution of 4-oxo-2-(3-(trifluoromethyl)phenyl)-4H-chromene-8-carbonyl chloride 37 (83 mg, 0.235 mmol) and 6-(pyrrolidin-1-ylmethyl)pyridin-2-amine hydrochloride 49 (75 mg, 0.353 mmol) in CH₃CN (15 mL). The reaction mixture was heated at 60° C. for 12 h, cooled to room temperature and poured into H₂O. The mixture was extracted with CH₂Cl₂. The combined organics were dried (MgSO₄) and concentrated. The crude residue was purified by MPLC eluting with CH₂Cl₂/MeOH (0-10%) to give Compound 243 (46 mg, 40% yield). MS (ESI) calcd for $C_{27}H_{22}F_3N_3O_3$: 493.16. found: 494 [M+H].

Example 11

Synthesis of N-(5-methylthiazol-2-yl)-4-oxo-2-(2-(trifluoromethyl)pyridin-3-yl)-4H-chromene-8-carboxamide (Compound 305)

Step 1. Preparation of methyl 3-acetyl-2-hydroxybenzoate (38)

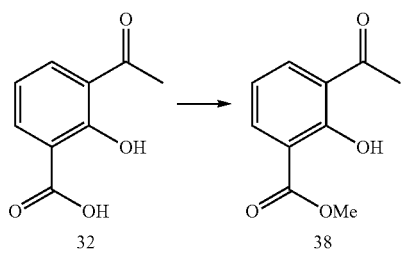

To a solution of 3-acetyl-2-hydroxybenzoic acid 32 (3 g, 16.7 mmol) in MeOH (50 mL) was added conc. $H_2SO_4$ (3.0 mL). The reaction mixture was heated at reflux for 12 h. After concentration en vacuo, the crude residue was diluted with $H_2O$, basified to pH=8 with aq $NaHCO_3$ and extracted with EtOAc. The combined organic extracts were dried ($MgSO_4$) and concentrated to give 38 as a white solid (550 mg, 20% yield).

Step 2. Preparation of methyl 2-hydroxy-3-(3-oxo-3-(2-(trifluoromethyl)pyridin-3-yl)propanoyl)benzoate (39)

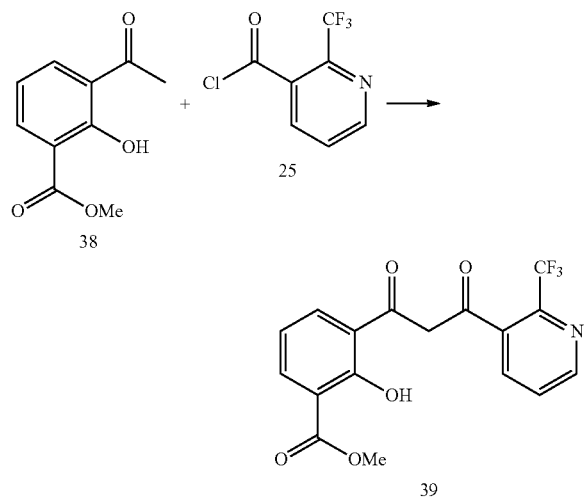

2-(trifluoromethyl)pyridine-3-carbonyl chloride 25 (300 mg, 1.46 mmol) was added to a mixture of methyl 3-acetyl-2-hydroxybenzoate 38 (183 mg, 1.46 mmol) and DBU (446 mg, 2.92 mmol) in pyridine at 0° C. The reaction mixture was heated at 80° C. for 12 h. The resulting mixture was poured into $H_2O$ and extracted with ethyl acetate. The organic layer was dried ($MgSO_4$) and concentrated to give 39 (600 mg) which was used with no further purification.

Step 3. Preparation of methyl 4-oxo-2-(2-(trifluoromethyl)pyridin-3-yl)-4H-chromene-8-carboxylate (40)

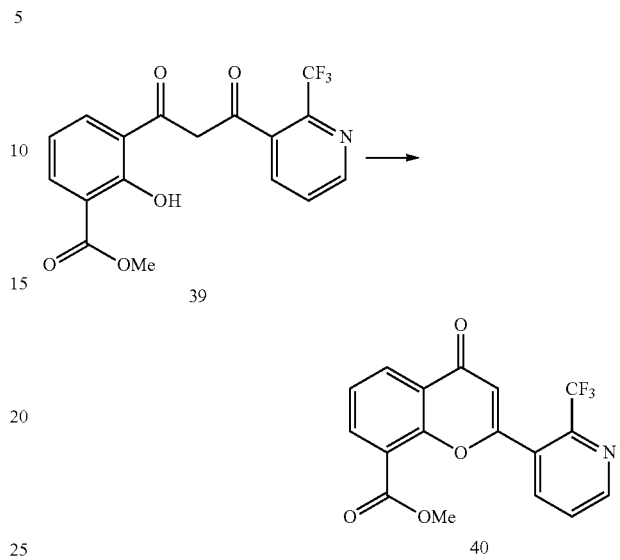

A mixture of 2-hydroxy-3-(3-oxo-3-(2-(trifluoromethyl)pyridin-3-yl)propanoyl)benzoate 39 (600 mg, 1.46 mmol) and con. HCl (1 mL) in acetic acid (5 mL) was heated at 100° C. for 4 hours. The reaction mixture was concentrated and sat. aq $NaHCO_3$ was added. The mixture was extracted with ethyl acetate and the combined organics were washed with brine, dried ($MgSO_4$) and concentrated. The crude residue was purified by flash chromatography to give 40 (120 mg, 23% yield).

Step 4. Preparation of 4-oxo-2-(2-(trifluoromethyl)pyridin-3-yl)-4H-chromene-8-carboxylic acid (41)

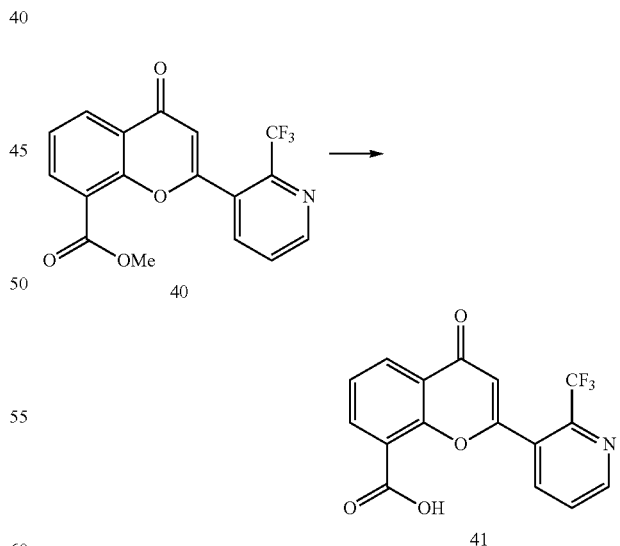

$LiOH \cdot H_2O$ (28 mg, 0.64 mmol) was added to a solution of methyl 4-oxo-2-(2-(trifluoromethyl)pyridin-3-yl)-4H-chromene-8-carboxylate 40 (120 mg, 0.32 mmol) in $H_2O$/THF/MeOH (5 mL, 1:2:2). The reaction mixture was stirred at ambient temperature for 12 h, poured into $H_2O$ and the pH adjusted to 3. The mixture was extracted with ethyl acetate, dried (MgSO$_4$) and concentrated to give 41 (120 mg) which was with no further purification.

Step 5. Preparation of N-(5-methylthiazol-2-yl)-4-oxo-2-(2-(trifluoromethyl)pyridin-3-yl)-4H-chromene-8-carboxamide (Compound 305)

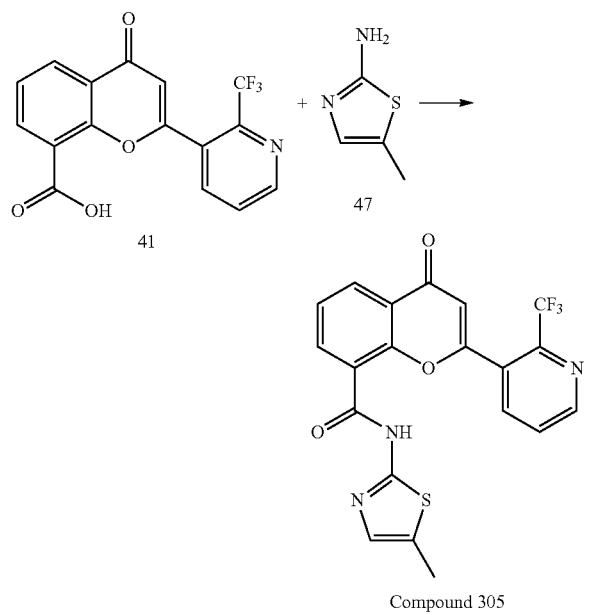

Compound 305

A mixture of 4-oxo-2-(2-(trifluoromethyl)pyridin-3-yl)-4H-chromene-8-carboxylic acid 41 (210 mg, 0.6 mmol), 5-methyl-1,3-thiazole-2-ylamine 47 (68 mg, 0.6 mmol), HATU (274 mg, 0.72 mmol), and DIPEA (155 mg, 1.2 mmol) in DMF (4 mL) was stirred at 55° C. for 12 h. The reaction mixture was poured into H$_2$O (25 mL) and extracted with ethyl acetate. The organic layer was concentrated and purified by flash chromatography to give Compound 305 (85 mg, 32% yield). MS (ESI) calcd for C$_{20}$H$_{12}$F$_3$N$_3$O$_3$S: 431.06. found: 432 [M+H].

Example 12

Synthesis of N-(5-methylthiazol-2-yl)-4-oxo-2-(pyridin-4-yl)-4H-chromene-8-carboxamide (Compound 248)

Step 1. Preparation of 2-acetyl-6-(methoxycarbonyl)phenyl isonicotinate (43)

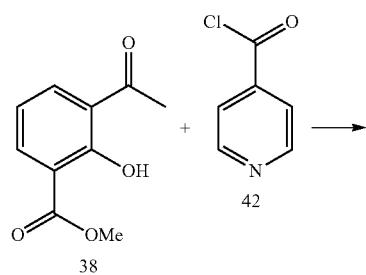

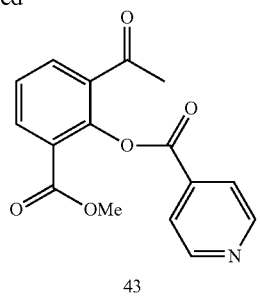

Pyridine-4-carbonyl chloride 42 (705 mg, 5 mmol) was added to a solution of methyl 3-acetyl-2-hydroxybenzoate 38 (650 mg, 3.6 mmol) and DIEA (932 mg, 7.2 mmol) in CH$_3$CN (10 mL). The reaction mixture was stirred at room temperature for 12 h, poured into H$_2$O (20 mL) and extracted with CH$_2$Cl$_2$. The combined organic extracts were dried (MgSO$_4$) and concentrated. The residue was purified by prep HPLC to give the product as a yellow solid (855 mg, 83% yield).

Step 2. Preparation of methyl 2-hydroxy-3-(3-oxo-3-(pyridin-4-yl)propanoyl)benzoate (44)

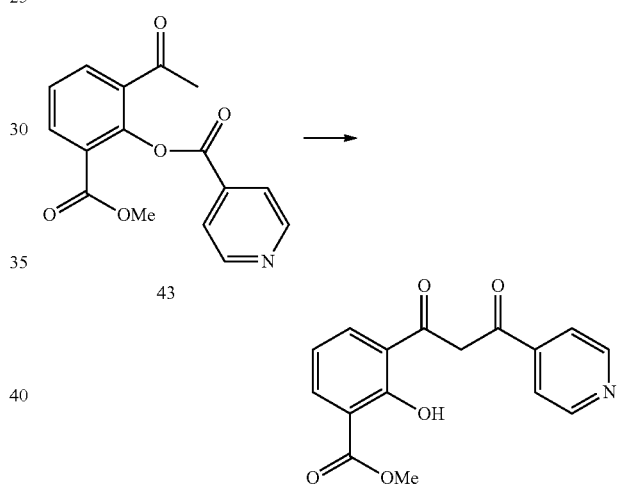

A solution of t-BuOK (3.03 ml, 7.5 mmol) in THF was added to a solution of 2-acetyl-6-(methoxycarbonyl)phenyl isonicotinate 43 (850 mg, 2.5 mmol) in THF (50 ml) at 0 C. The reaction mixture was stirred at room temperature for 12 h then concentrated to dryness to give 44.

Step 3. Preparation of methyl 4-oxo-2-(pyridin-4-yl)-4H-chromene-8-carboxylate (45)

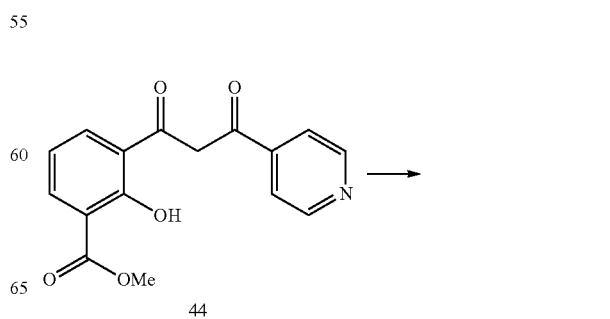

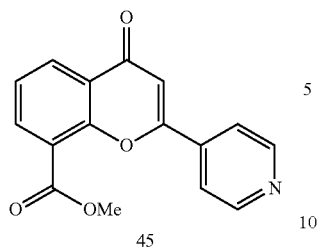

45

Methyl 4-oxo-2-(pyridin-4-yl)-4H-chromene-8-carboxylate 45 was prepared in 43% yield by a procedure similar to that used in Example 11, step 3, to produce 40.

Step 4. Preparation of 4-oxo-2-(pyridin-4-yl)-4H-chromene-8-carboxylic acid (46)

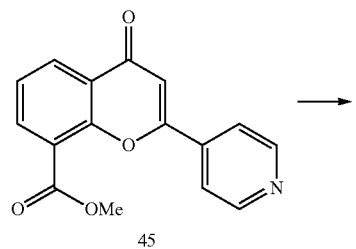

45

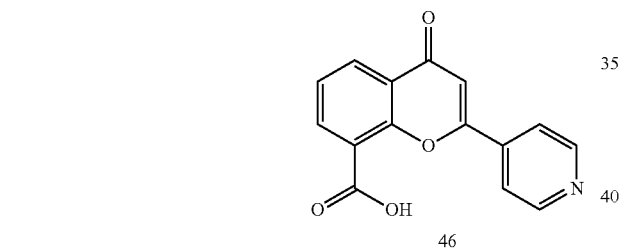

46

4-oxo-2-(pyridin-4-yl)-4H-chromene-8-carboxylic acid 46 was prepared in 63% yield by a procedure similar to that used in Example 11, step 4, to produce 4-oxo-2-(2-(trifluoromethyl)pyridin-3-yl)-4H-chromene-8-carboxylic acid 41.

Step 5. Preparation of N-(5-methylthiazol-2-yl)-4-oxo-2-(pyridin-4-yl)-4H-chromene-8-carboxamide (Compound 248)

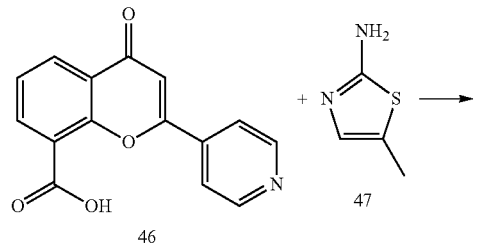

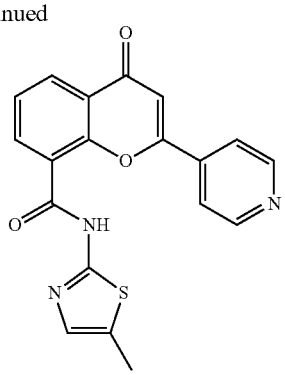

Compound 248

Compound 248 was prepared in 30% yield by a procedure similar to that used in Example 11, step 5, to produce N-(5-methylthiazol-2-yl)-4-oxo-2-(2-(trifluoromethyl)pyridin-3-yl)-4H-chromene-8-carboxamide Compound 305. MS (ESI) calcd for $C_{19}H_{13}N_3O_3S$: 363.07. found: 364 [M+H].

Additional compounds in Table 1 and within the scope of the invention can be prepared by analagous techniques by coupling the appropriate carboxylic acid and amine intermediates. Examples of additional carboxylic acid and amine intermediates are set forth below.

Example 13

Synthesis of 2-(difluoromethyl)benzaldehyde (52)

Step 1. Preparation of 1-bromo-2-(difluoromethyl)benzene (51)

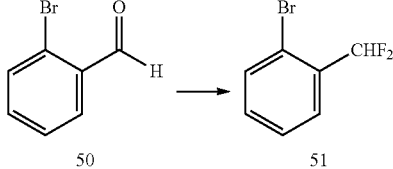 [SMILES: O=Cc1ccccc1Br ; FC(F)c1ccccc1Br]

DAST (8.7 g, 54.1 mmol) was added to a mixture of 2-bromobenzaldehyde 50 (5.0 g, 27.0 mmol) in dichloromethane (100 mL) at 0° C. The reaction mixture was stirred at room temperature for 12 h, poured into sat. aq $NaHCO_3$, and extracted with EtOAc. The organic layer was concentrated to give 51 (5.4 g, 96% yield), which was used in next step with no further purification.

Step 2. Preparation of 2-(difluoromethyl)benzaldehyde (52)

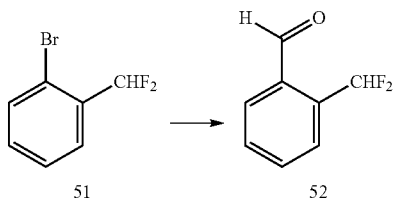 [SMILES: FC(F)c1ccccc1Br ; O=Cc1ccccc1C(F)F]

A solution of n-BuLi (4.2 mL, 10.6 mmol) in THF was added to a solution of 1-bromo-2-(difluoromethyl)benzene 51 (2.0 g, 9.7 mmol) in THF (50 mL) at −78° C. The reaction mixture was stirred for 30 min and DMF (1.4 g, 19.3 mmol) was added. Stirring was continued for 1 h at −40° C. and the reaction was quenched by the addition of sat. aq $NH_4Cl$. The crude mixture was extracted with Et$_2$O, dried (MgSO$_4$) and concentrated to give 52 (1.7 g, 94% yield).

Example 14

Synthesis of (R)-2-((2,2-dimethyl-1,3-dioxolan-4-yl)methoxy)nicotinic acid (55)

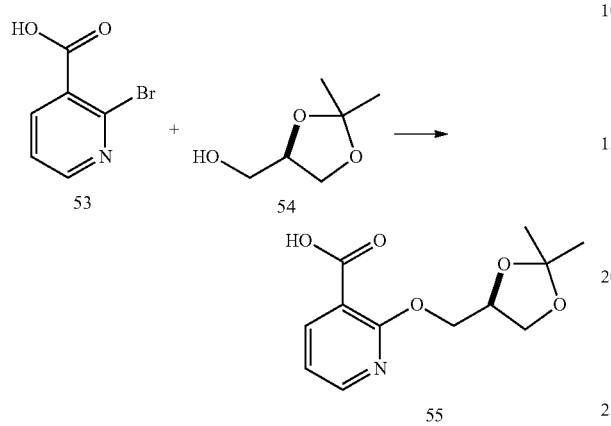

(R)-(2,2-dimethyl-1,3-dioxolan-4-yl)methanol 54 (1.8 mL, 14.9 mmol) was added to a room temperature suspension of NaH (392 mg, 16.3 mmol) in THF (30 mL). The reaction mixture was stirred at room temperature for 30 min and 2-bromo-nicotinic acid 53 (1 g, 4.95 mmol) was added. The reaction mixture was heated at reflux for 12 h. After cooling to room temperature, the pH was adjusted to 3 by the addition of 3 N HCl. The mixture was poured into brine and extracted with EtOAc. The combined organics were dried and concentrated. The crude product was recrystallized from pentane/EtOAc to give 55 (1.2 g, 92% yield). The acetonide protecting group could be removed after coupling with the appropriate aniline by treatment with EtOH/3 N HCl (4:1) at reflux for 12 h.

Example 15

Synthesis of (R)-6-((2,2-dimethyl-1,3-dioxolan-4-yl)methoxy)picolinic acid (57)

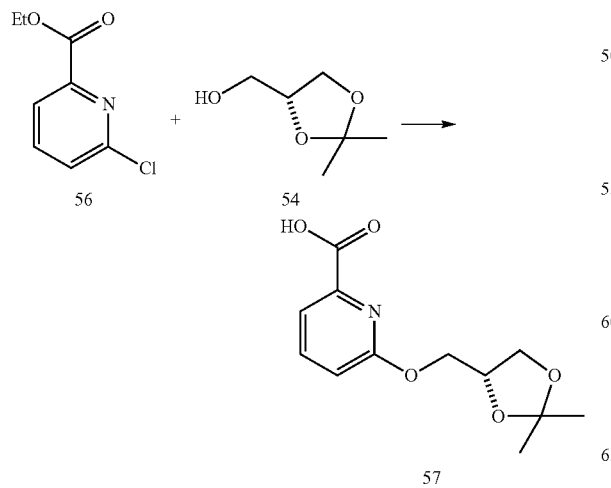

(R)-6-((2,2-dimethyl-1,3-dioxolan-4-yl)methoxy)picolinic acid 57 was prepared in 74% yield by a procedure similar to that reported in Example 14 for 55. The acetonide protecting group could be removed after coupling with the appropriate aniline by treatment with EtOH/3 N HCl (4:1) at reflux for 12 h.

Example 16

Synthesis of (R)-2-((2,2-dimethyl-1,3-dioxolan-4-yl)methoxy)isonicotinic acid (59)

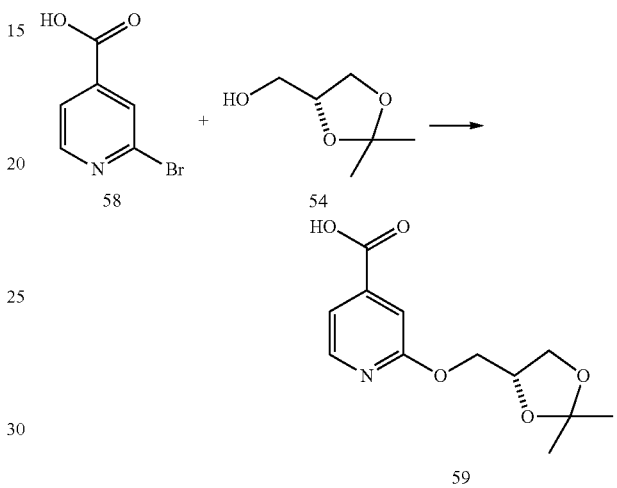

(R)-2-((2,2-dimethyl-1,3-dioxolan-4-yl)methoxy)isonicotinic acid 59 was prepared in 72% yield by a procedure similar to that reported in Example 14 for 55. The acetonide protecting group could be removed after coupling with the appropriate aniline by treatment with EtOH/3 N HCl (4:1) at reflux for 12 h.

Example 17

Synthesis of (R)-6-((2,2-dimethyl-1,3-dioxolan-4-yl)methoxy)nicotinic acid (61)

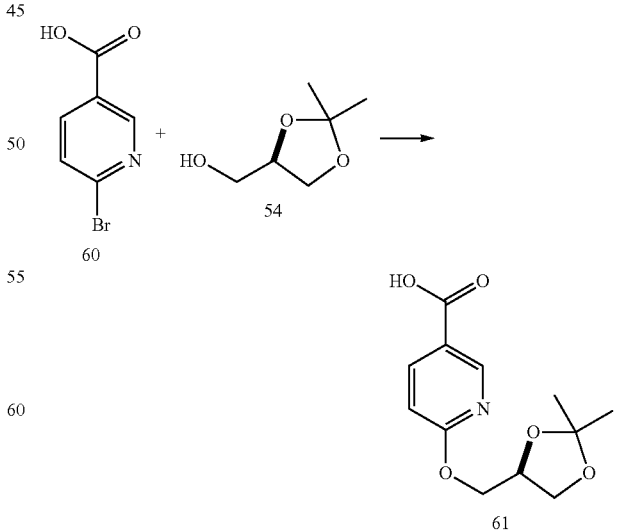

(R)-6-((2,2-dimethyl-1,3-dioxolan-4-yl)methoxy)nicotinic acid 61 was prepared in 60% yield by a procedure similar to that reported in Example 14 for 55. The acetonide protecting group could be removed after coupling with the appropriate aniline by treatment with EtOH/3 N HCl (4:1) at reflux for 12 h.

Example 18

Synthesis of 6-((2,2-dimethyl-1,3-dioxolan-4-yl)methoxy)picolinic acid (64)

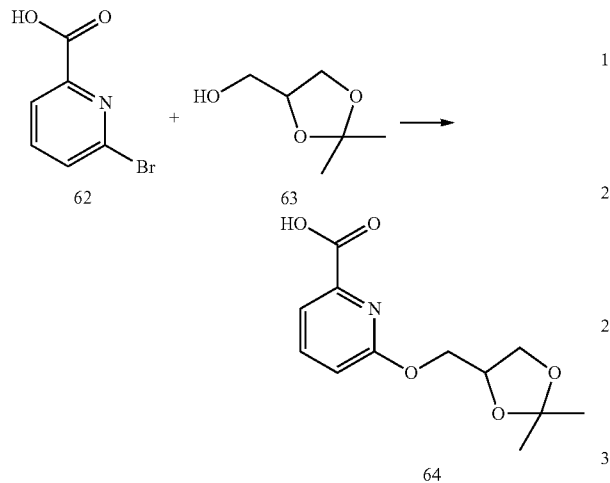

6-((2,2-dimethyl-1,3-dioxolan-4-yl)methoxy)picolinic acid 64 was prepared in 66% yield by a procedure similar to that reported in Example 14 for 55. The acetonide protecting group could be removed after coupling with the appropriate aniline by treatment with EtOH/3 N HCl (4:1) at reflux for 12 h.

Example 19

Synthesis of 2-((2,2-dimethyl-1,3-dioxolan-4-yl)methoxy)nicotinic acid (65)

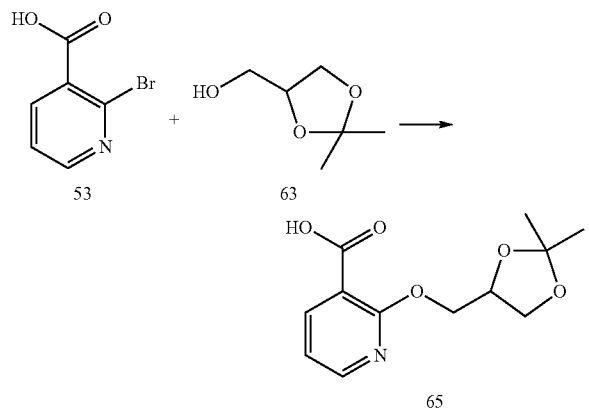

2-((2,2-dimethyl-1,3-dioxolan-4-yl)methoxy)nicotinic acid 65 was prepared in 23% yield by a procedure similar to that reported in Example 14 for 55. The acetonide protecting group could be removed after coupling with the appropriate aniline by treatment with EtOH/3 N HCl (4:1) at reflux for 12 h.

Example 20

Synthesis 6-(morpholinomethyl)picolinic acid (69)

Step 1. Preparation of 4-((6-bromopyridin-2-yl)methyl)morpholine (68)

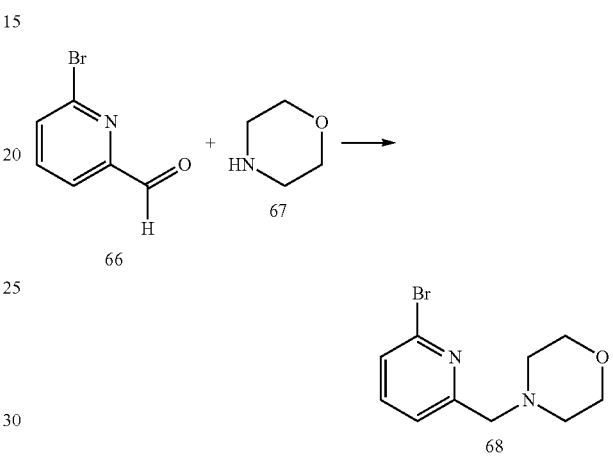

NaBH(OAc)$_3$ (68.5 g, 0.323 mol) was added to a solution of 6-bromopicolinaldehyde 66 (40 g, 0.22 mol) and morpholine 67 (20.9 g, 0.24 mol) in 1,2-dichloroethane (500 mL). The mixture was stirred at room temperature for 16 h. Saturated NaHCO$_3$ (500 mL) was added and the mixture was extracted with EtOAc, washed with brine, dried (Na$_2$SO$_4$) and concentrated in vacuo. The residue was purified by flash chromatography on silica gel eluting with petroleum ether:ethyl acetate (10:1) to give 68 (38 g, 68% yield).

Step 2. Preparation of 6-(morpholinomethyl)picolinic acid (69)

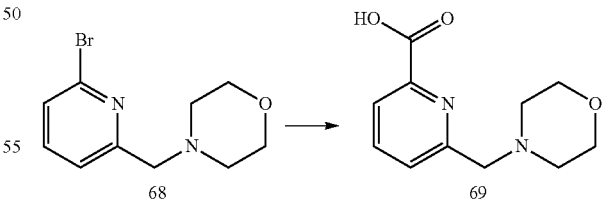

n-BuLi (56 mL, 0.140 mol) in THF was added to a solution of 4-((6-bromopyridin-2-yl)methyl)morpholine 68 (30 g, 0.12 mol) in THF (500 mL) at −78° C. The mixture was stirred for 30 min and CO$_2$ (gas) was bubbled through the reaction mixture for 30 min. The volatiles were removed in vacuo and the residue was extracted with CH$_2$Cl$_2$/MeOH (1:1). The solvent was evaporated and the residue was washed with CH$_2$Cl$_2$ to give 69 (11.0 g, 42% yield).

Example 21

Synthesis of 6-(pyrrolidin-1-ylmethyl)picolinic acid (74)

Step 1. Preparation of methyl 6-(chloromethyl)picolinate (71)

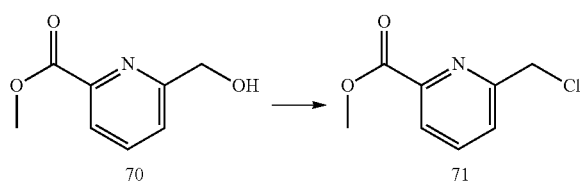

SOCl$_2$ (57 g, 0.48 mol) was added to a solution of methyl 6-(hydroxymethyl)picolinate 70 (40.0 g, 0.239 mol) (*Chem. Eur. J.* 2006, 12, 6393-6402) in dichloromethane (500 mL) at room temperature. The mixture was stirred at 40° C. for 1 h and sat. aq K$_2$CO$_3$ was added to adjust the pH to 9. The mixture was extracted with CH$_2$Cl$_2$ and the combined organics were washed with brine, dried (Na$_2$SO$_4$), and concentrated in vacuo to give 71 (45 g).

Step 2. Preparation of methyl 6-(pyrrolidin-1-ylmethyl)picolinate (73)

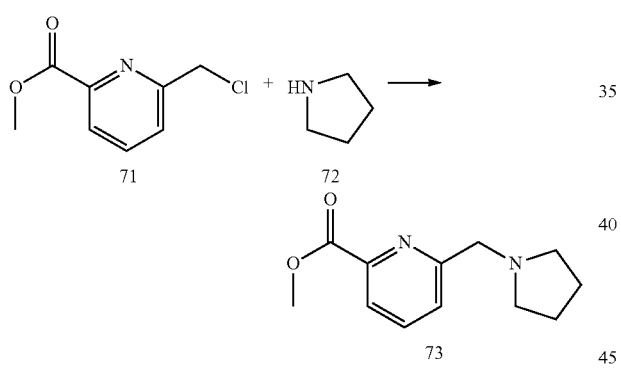

K$_2$CO$_3$ (66 g, 0.48 mol) was added to a solution of methyl 6-(chloromethyl)picolinate 71 (45.0 g) and pyrrolidine 72 (34 g, 0.48 mol) in DMF (300 mL). The reaction mixture was heated at 80° C. for 12 h. H$_2$O (300 mL) was added and the mixture was extracted with EtOAc. The combined organic layers were washed with brine, dried (Na$_2$SO$_4$) and concentrated in vacuo to give 73 (36 g).

Step 3. Preparation of 6-(pyrrolidin-1-ylmethyl)picolinic acid (74)

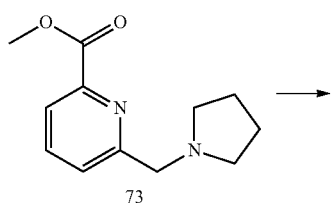

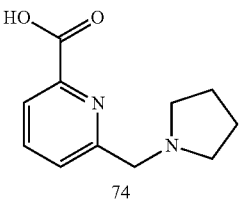

A mixture of methyl 6-(pyrrolidin-1-ylmethyl)picolinate 73 (36 g) and NaOH (40 g, 1.0 mol) in ethanol/H$_2$O (320 mL) was stirred at 75° C. for 16 h. The pH was adjusted to 7 with 3N HCl and extracted with EtOAc. The aqueous layer was concentrated to dryness and extracted with dichloromethane/methanol (v:v=3:1), The organic layer was dried to give 74 (27 g, 55% yield).

Example 22

Synthesis of N-methyl proline (76)

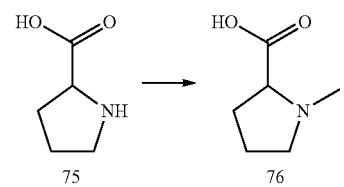

Compound 76 was prepared by a procedure similar to that reported in *J. Org. Chem.* 2003, 66, 2652.

Example 23

Synthesis of 6-(pyrrolidin-1-ylmethyl)pyridin-2-amine (49)

Step 1. Preparation of ethyl 6-aminopicolinate (78)

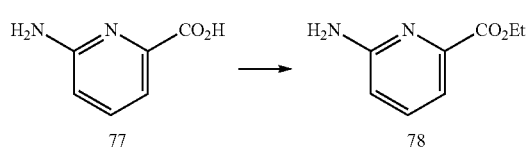 [SMILES: Nc1cccc(C(=O)O)n1 ; CCOC(=O)c1cccc(N)n1]

To a solution of 2-amino-6-pyridinecarboxylic acid 77 (6.0 g, 43.5 mmol) in ethanol (150 mL) was added thionyl chloride (12.0 g, 101 mmol) at 0° C. The resulting reaction mixture was stirred at reflux for 12 h. Upon cooling to room temperature, the reaction mixture was concentrated under reduced pressure. Saturated aqueous Na$_2$CO$_3$ solution was added until the pH of the solution reached 9. The mixture was concentrated under reduced pressure and dichloromethane (150 mL) was added to the resulting residue. The mixture was stirred vigorously at room temperature for 30 min and then filtered. The filtrate was concentrated under reduced pressure to afford 78 (5.5 g, 76% yield).

Step 2. Preparation of ethyl 6-(tert-butoxycarbonylamino)picolinate (79)

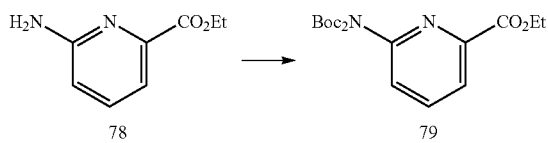

To a solution of ethyl 6-aminopicolinate 78 (5.5 g, 33 mmol) in t-BuOH (120 mL) and acetone (40 mL) was added 4-dimethylaminopyridine (0.08 g, 0.66 mmol) and di-tert-butyl dicarbonate (10.8 g, 49.5 mmol). The reaction mixture was stirred at room temperature for 18 h. The solvent was removed by concentration under reduced pressure and a mixture of hexane/dichloromethane (180 mL, 3:1) was added. The resulting mixture was cooled to −20° C. for 2 h. The resulting solids were collected by filtration and dried to afford 79 (11.0 g, 91% yield).

Step 3. Preparation of tert-butyl 6-(hydroxymethyl)pyridin-2-ylcarbamate (80)

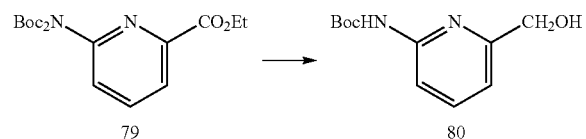

To a stirred solution of ethyl 6-(bis(tert-butoxycarbonyl)amino)picolinate 79 (11.0 g, 33 mmol) in THF (120 mL) under nitrogen was added LiAlH$_4$ (3.80 g, 100 mmol) in THF (60 mL) over a period of 30 min at 0° C. The reaction mixture was stirred at 0° C. for 6 h and carefully quenched by the addition of H$_2$O (2.0 mL) and 10% NaOH solution (4.0 mL) at 0° C. The reaction mixture was filtered and the filtrate was dried (Na$_2$SO$_4$) and concentrated under reduced pressure. The resulting residue purified by chromatography (1:1 petroleum ether:ethyl acetate) to afford 80 (3.0 g, 41% yield).

Step 4. Preparation of (6-(tert-butoxycarbonylamino)pyridin-2-yl)methyl methanesulfonate (81)

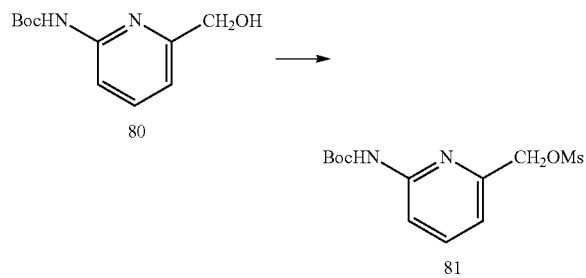

To a solution of tert-butyl 6-(hydroxymethyl)pyridin-2-ylcarbamate 80 (3.0 g, 13.4 mmol) and diisopropylethylamine (5.0 g, 40 mmol) in acetonitrile (30 mL) was added methanesulfonyl chloride (2.0 g, 17.4 mmol) over a period of 30 min at 0° C. and the mixture was stirred for 2 h at room temperature. The reaction was quenched by adding saturated aqueous NaHCO$_3$ and extracted with ethyl acetate (3×60 mL). The combined organic layers were washed with brine, dried (Na$_2$SO$_4$) and concentrated under reduced pressure to afford quantitative yield of crude 81.

Step 5. Preparation of tert-butyl 6-(pyrrolidin-1-ylmethyl)pyridin-2-ylcarbamate (82)

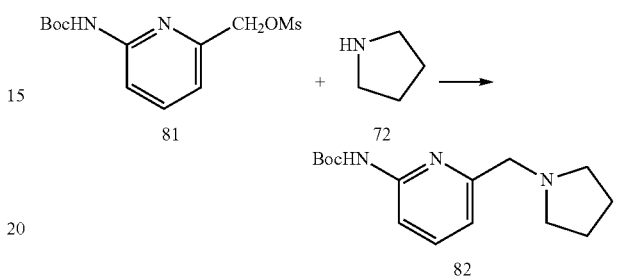

A mixture containing (6-(tert-butoxycarbonylamino)pyridin-2-yl)methyl methanesulfonate 81 (1.30 g, 3.2 mmol), pyrrolidine 72 (0.46 g, 6.4 mmol) and K$_2$CO$_3$ (1.30 g, 9.6 mmol) in acetonitrile (15 mL) was stirred at room temperature for 12 h. Saturated aqueous NaHCO$_3$ was added and the mixture was concentrated under reduced pressure. The resulting aqueous layer was extracted with EtOAc. The combined organic layers were dried (Na$_2$SO$_4$) and concentrated under reduced pressure to afford 82 (0.75 g, 62% yield).

Step 6. Preparation of 6-(pyrrolidin-1-ylmethyl)pyridin-2-amine (49)

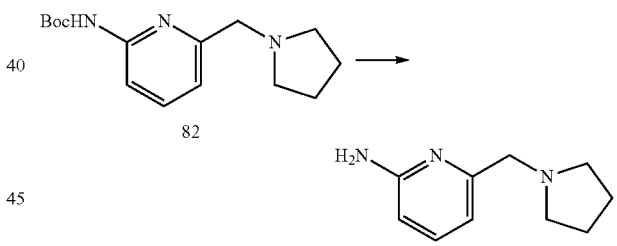

To a solution of tert-butyl 6-(pyrrolidin-1-ylmethyl)pyridin-2-ylcarbamate 82 (750 mg, 2.71 mmol) in dichloromethane (10 mL) was added trifluoroacetic acid (4.0 mL) at room temperature. The resulting reaction mixture was stirred at room temperature for 6 h and then concentrated under reduced pressure. Saturated aqueous Na$_2$CO$_3$ was added to the resulting residue until the solution pH reached 9. The mixture was then extracted with ethyl acetate (3×25 mL). The combined organic layers were dried with Na$_2$SO$_4$ and concentrated under reduced pressure to afford 49 (440 mg, 92% yield).

Example 24

Biological Activity

A mass spectrometry based assay was used to identify modulators of SIRT1 activity. The mass spectrometry based assay utilizes a peptide having 20 amino acid residues as follows: Ac-EE-K(biotin)-GQSTSSHSK(Ac)NleSTEG-K(5TMR)-EE-NH2 (SEQ ID NO: 1) wherein K(Ac) is an acetylated lysine residue and Nle is a norleucine. The peptide is labeled with the fluorophore 5TMR (excitation 540 nm/emission 580 nm) at the C-terminus. The sequence of the peptide substrate is based on p53 with several modifications. In addition, the methionine residue naturally present in the sequence was replaced with the norleucine because the methionine may be susceptible to oxidation during synthesis and purification.

The mass spectrometry assay is conducted as follows: 0.5 µM peptide substrate and 120 µM βNAD$^+$ is incubated with 10 nM SIRT1 for 25 minutes at 25° C. in a reaction buffer (50 mM Tris-acetate pH 8, 137 mM NaCl, 2.7 mM KCl, 1 mM MgCl$_2$, 5 mM DTT, 0.05% BSA). Test compounds may be added to the reaction as described above. The SirT1 gene is cloned into a T7-promoter containing vector and transformed into BL21(DE3). After the 25 minute incubation with SIRT1, 10 µL of 10% formic acid is added to stop the reaction. Reactions are sealed and frozen for later mass spec analysis. Determination of the mass of the substrate peptide allows for precise determination of the degree of acetylation (i.e. starting material) as compared to deacetylated peptide (product).

A control for inhibition of sirtuin activity is conducted by adding 1 µL of 500 mM nicotinamide as a negative control at the start of the reaction (e.g., permits determination of maximum sirtuin inhibition). A control for activation of sirtuin activity is conducted using 10 nM of sirtuin protein, with 1 µL of DMSO in place of compound, to determine the amount of deacetylation of the substrate at a given timepoint within the linear range of the assay. This timepoint is the same as that used for test compounds and, within the linear range, the endpoint represents a change in velocity.

For the above assay, SIRT1 protein was expressed and purified as follows. The SirT1 gene was cloned into a T7-promoter containing vector and transformed into BL21(DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl] phosphine (TCEP), 10 µM ZnCl$_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

Sirtuin modulating compounds that activated SIRT1 were identified using the assay described above and are shown below in Table 1. The EC$_{1.5}$ values for the activating compounds are represented by A (EC$_{1.5}$<1.0 B (EC$_{1.5}$ 1-25 µM), C (EC$_{1.5}$>25 µM). The percent maximum fold activation is represented by A (Fold activation >200%) or B (Fold Activation <200%).

TABLE 1

| Compd No | [M + H]+ | Structure | EC1.5 µM | % Fold Act. |
|---|---|---|---|---|
| 200 | 349 | 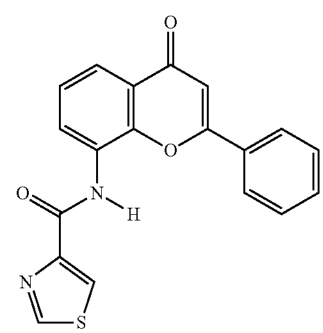 [SMILES: O=C(Nc1cccc2c(=O)cc(-c3ccccc3)oc12)c1cscn1] | C | B |
| 201 | 344 | 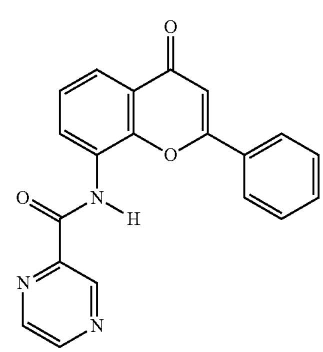 [SMILES: O=C(Nc1cccc2c(=O)cc(-c3ccccc3)oc12)c1cnccn1] | C | B |

TABLE 1-continued

| Compd No | [M + H]+ | Structure | EC1.5 μM | % Fold Act. |
|---|---|---|---|---|
| 202 | 433 | 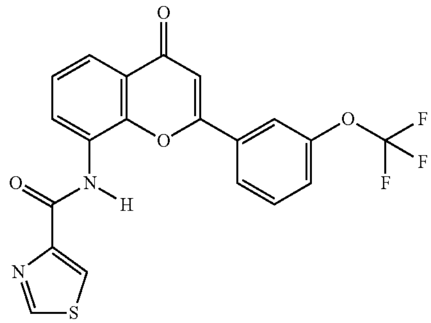 [SMILES: O=C(Nc1cccc2c(=O)cc(-c3cccc(OC(F)(F)F)c3)oc12)c1cscn1] | C | B |
| 203 | 428 | 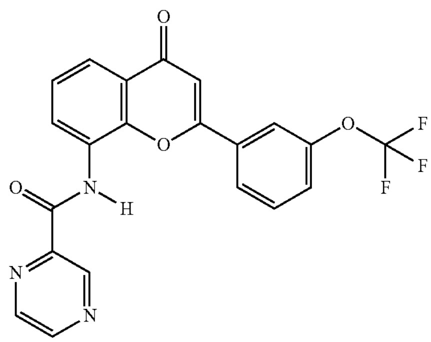 [SMILES: O=C(Nc1cccc2c(=O)cc(-c3cccc(OC(F)(F)F)c3)oc12)c1cnccn1] | B | B |
| 204 | 417 | 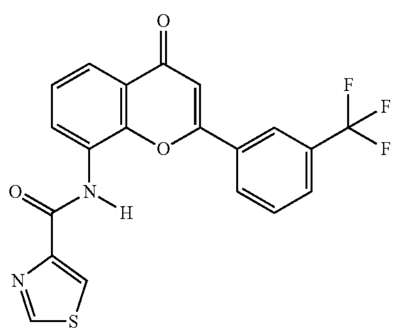 [SMILES: O=C(Nc1cccc2c(=O)cc(-c3cccc(C(F)(F)F)c3)oc12)c1cscn1] | B | B |
| 205 | 412 | 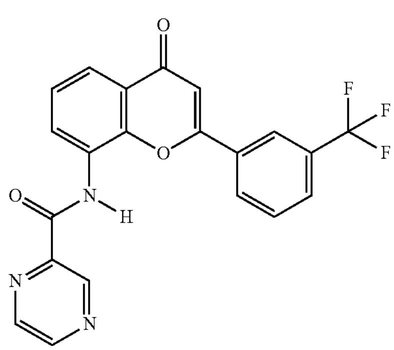 [SMILES: O=C(Nc1cccc2c(=O)cc(-c3cccc(C(F)(F)F)c3)oc12)c1cnccn1] | C | B |

TABLE 1-continued
| Compd No | [M + H]+ | Structure | EC1.5 μM | % Fold Act. |
|---|---|---|---|---|
| 206 | 417 | 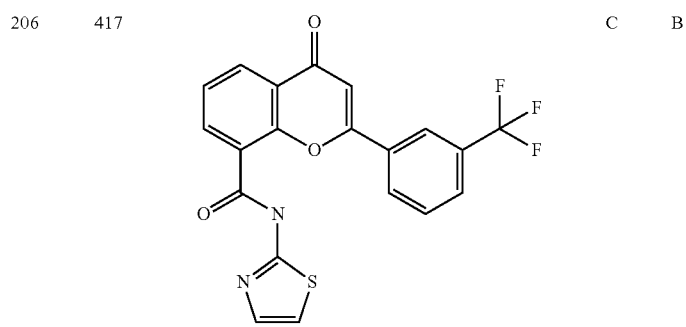 | C | B |
| 207 | 411 | 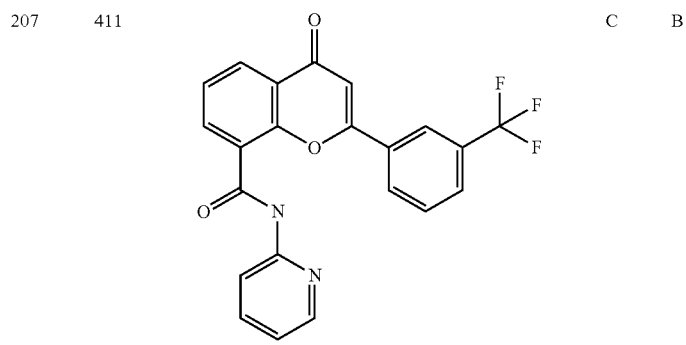 | C | B |
| 208 | 434 | 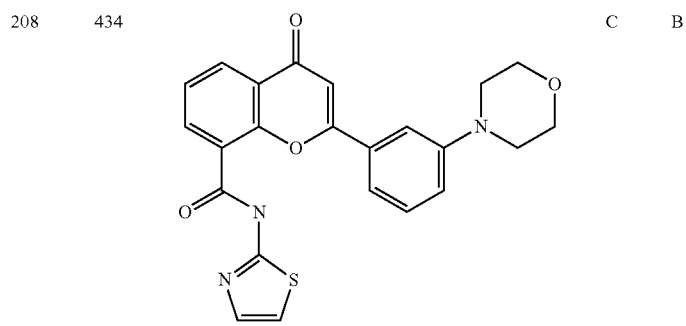 | C | B |
| 209 | 428 | 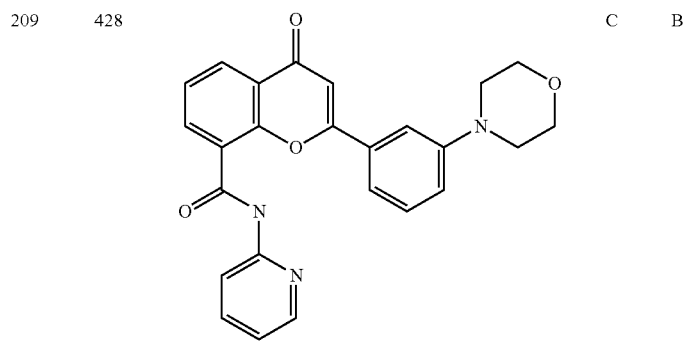 | C | B |

TABLE 1-continued
| Compd No | [M + H]+ | Structure | EC1.5 μM | % Fold Act. |
|---|---|---|---|---|
| 210 | 433 | 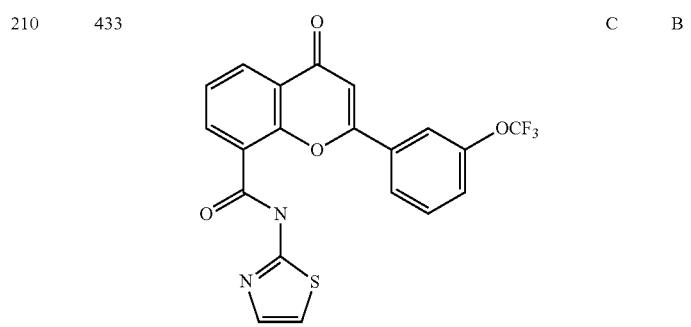 | C | B |
| 211 | 427 | 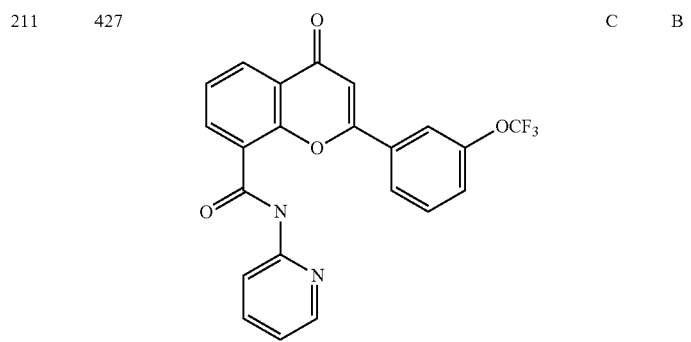 | C | B |
| 212 | 434 | 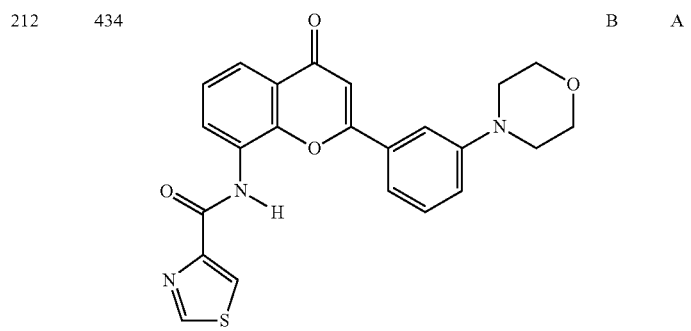 | B | A |
| 213 | 428 | 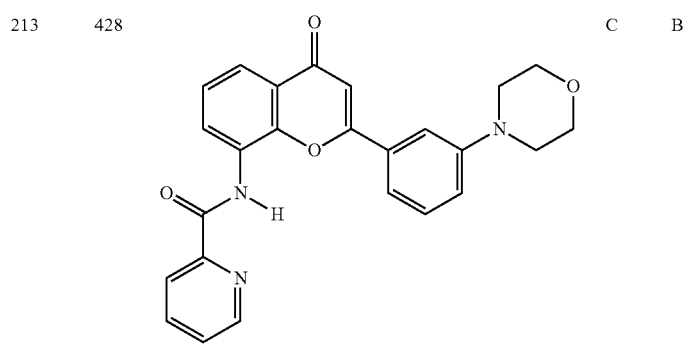 | C | B |

TABLE 1-continued
| Compd No | [M + H]+ | Structure | EC1.5 μM | % Fold Act. |
|---|---|---|---|---|
| 214 | 429 | 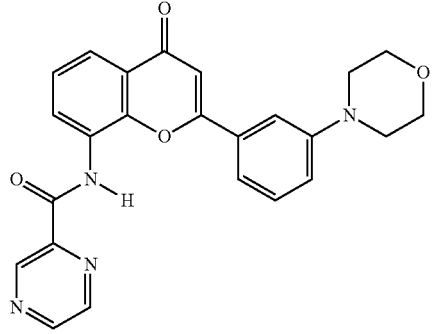 [SMILES: O=C(Nc1cccc2c(=O)cc(-c3cccc(N4CCOCC4)c3)oc12)c1cnccn1] | B | B |
| 215 | 350 | 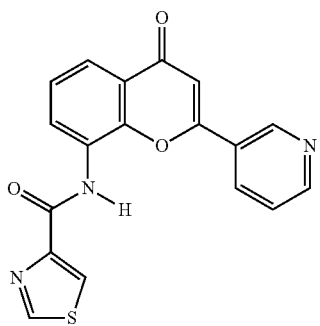 [SMILES: O=C(Nc1cccc2c(=O)cc(-c3cccnc3)oc12)c1cscn1] | C | B |
| 216 | 344 | 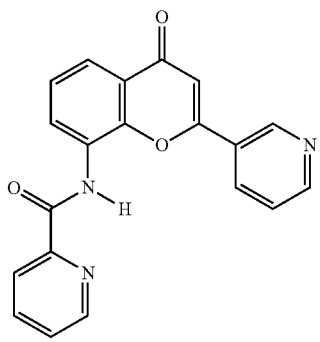 | C | B |
| 217 | 345 | 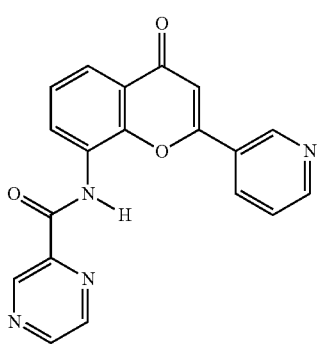 [SMILES: O=C(Nc1cccc2c(=O)cc(-c3cccnc3)oc12)c1cnccn1] | C | B |

TABLE 1-continued

| Compd No | [M + H]+ | Structure | EC1.5 μM | % Fold Act. |
|---|---|---|---|---|
| 218 | 421 | (structure) | B | B |
| 219 | 422 | (structure) | C | B |
| 220 | 427 | (structure) | C | B |
| 221 | 421 | (structure) | C | B |

TABLE 1-continued

| Compd No | [M + H]+ | Structure | EC1.5 µM | % Fold Act. |
|---|---|---|---|---|
| 222 | 427 | 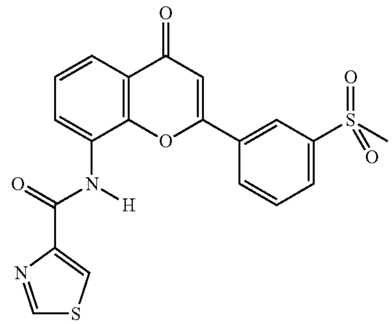 [SMILES: CS(=O)(=O)c1cccc(-c2cc(=O)c3cccc(NC(=O)c4cscn4)c3o2)c1] | C | B |
| 223 | 442 | 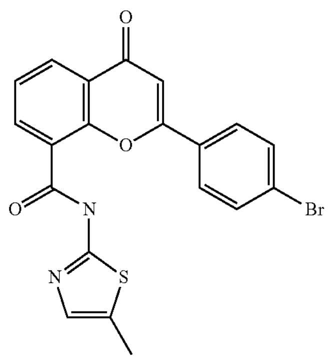 [SMILES: Cc1cnc(NC(=O)c2cccc3c(=O)cc(-c4ccc(Br)cc4)oc23)s1] | C | B |
| 224 | 411 | 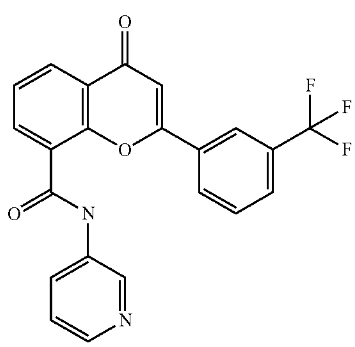 | C | B |
| 225 | 411 | 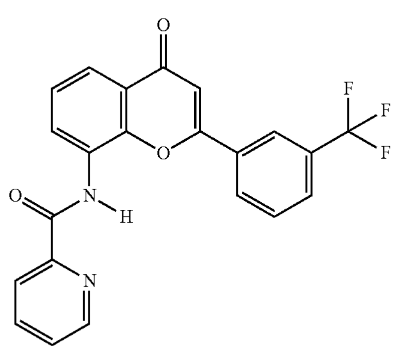 | C | B |

TABLE 1-continued

| Compd No | [M + H]+ | Structure | EC1.5 µM | % Fold Act. |
|---|---|---|---|---|
| 226 | 411 | 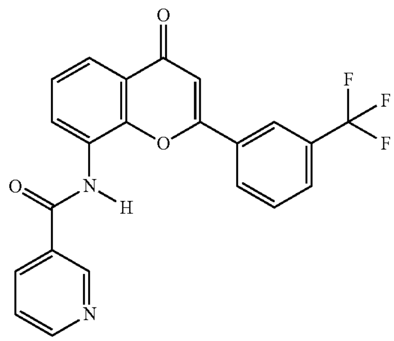 [SMILES: O=C(Nc1cccc2c(=O)cc(-c3cccc(C(F)(F)F)c3)oc12)c1cccnc1] | C | B |
| 227 | 417 | 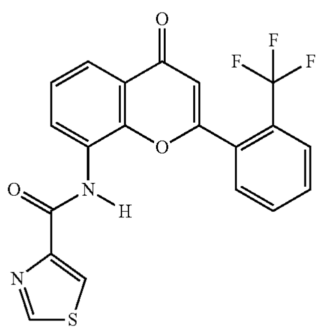 [SMILES: O=C(Nc1cccc2c(=O)cc(-c3ccccc3C(F)(F)F)oc12)c1cscn1] | A | A |
| 228 | 417 | 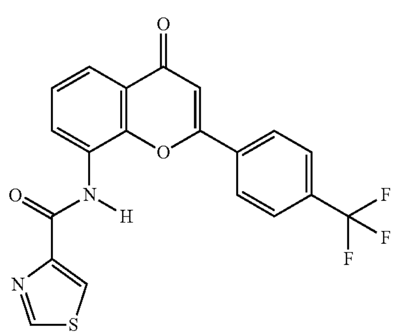 [SMILES: O=C(Nc1cccc2c(=O)cc(-c3ccc(C(F)(F)F)cc3)oc12)c1cscn1] | C | B |
| 229 | 434 | 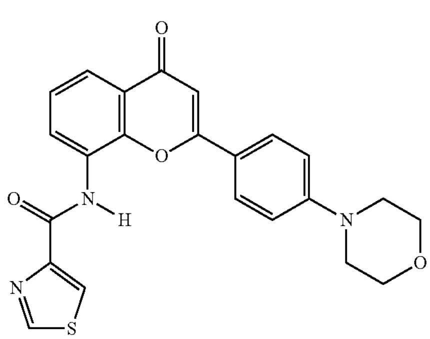 [SMILES: O=C(Nc1cccc2c(=O)cc(-c3ccc(N4CCOCC4)cc3)oc12)c1cscn1] | C | B |

TABLE 1-continued

| Compd No | [M + H]+ | Structure | EC1.5 μM | % Fold Act. |
|---|---|---|---|---|
| 230 | 428 | 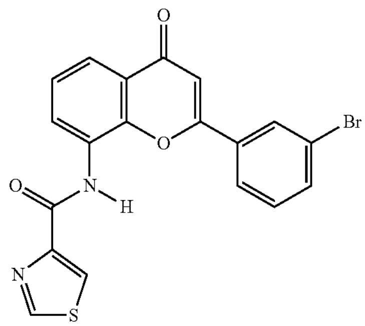 [SMILES: O=C(Nc1cccc2c(=O)cc(-c3cccc(Br)c3)oc12)c1cscn1] | C | B |
| 231 | 428 | 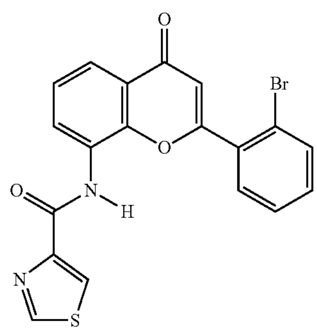 | A | A |
| 232 | 428 | 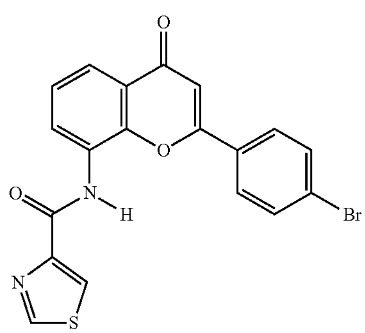 [SMILES: O=C(Nc1cccc2c(=O)cc(-c3ccc(Br)cc3)oc12)c1cscn1] | C | B |
| 233 | 428 | 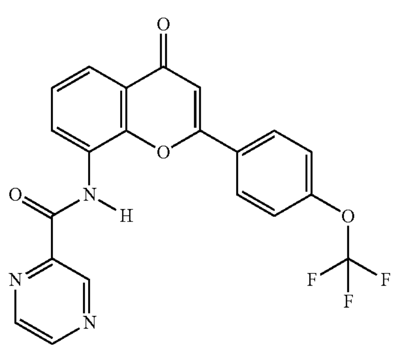 [SMILES: O=C(Nc1cccc2c(=O)cc(-c3ccc(OC(F)(F)F)cc3)oc12)c1cnccn1] | C | B |

TABLE 1-continued

| Compd No | [M + H]+ | Structure | EC1.5 µM | % Fold Act. |
|---|---|---|---|---|
| 234 | 428 | (structure) | A | A |
| 235 | 431 | (structure) | C | B |
| 236 | 442 | (structure) | C | B |
| 237 | 442 | (structure) | B | B |

TABLE 1-continued
| Compd No | [M + H]+ | Structure | EC1.5 µM | % Fold Act. |
|---|---|---|---|---|
| 238 | 364 | 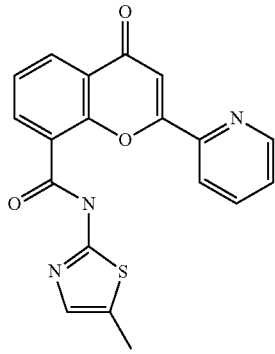 [SMILES: Cc1cnc(NC(=O)c2cccc3c(=O)cc(-c4ccccn4)oc23)s1] | C | B |
| 239 | 364 | 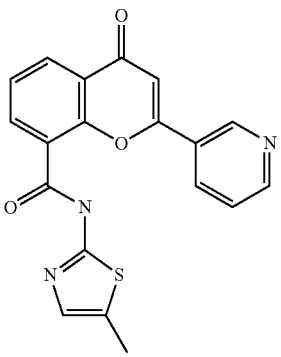 [SMILES: Cc1cnc(NC(=O)c2cccc3c(=O)cc(-c4cccnc4)oc23)s1] | C | B |
| 240 | 434 | 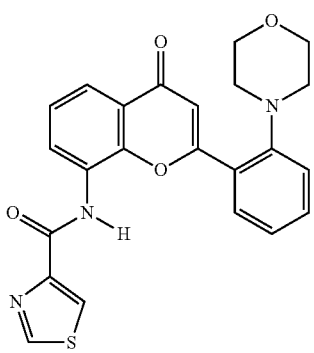 [SMILES: O=C(Nc1cccc2c(=O)cc(-c3ccccc3N3CCOCC3)oc12)c1cscn1] | B | A |
| 241 | 421 | 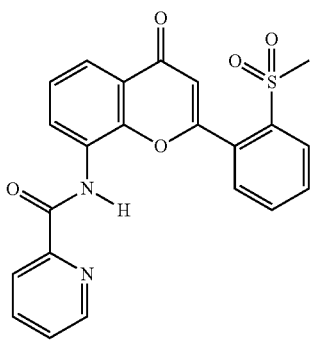 [SMILES: CS(=O)(=O)c1ccccc1-c1cc(=O)c2cccc(NC(=O)c3ccccn3)c2o1] | B | A |

TABLE 1-continued

| Compd No | [M + H]+ | Structure | EC1.5 µM | % Fold Act. |
|---|---|---|---|---|
| 242 | 421 | 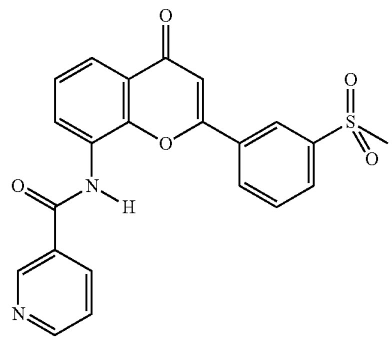 | C | B |
| 243 | 494 | 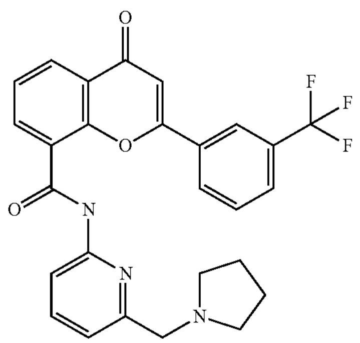 [SMILES: O=C(Nc1cccc(CN2CCCC2)n1)c1cccc2c(=O)cc(-c3cccc(C(F)(F)F)c3)oc12] | B | A |
| 244 | 501 | 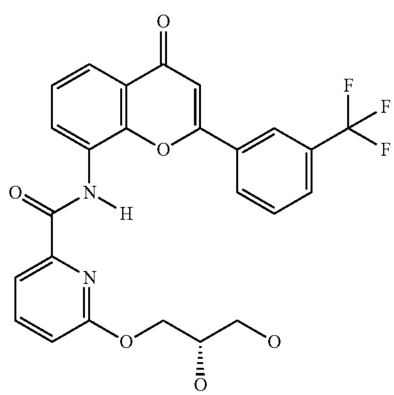 [SMILES: O=C(Nc1cccc2c(=O)cc(-c3cccc(C(F)(F)F)c3)oc12)c1cccc(OC[C@@H](O)CO)n1] | B | A |
| 245 | 501 | 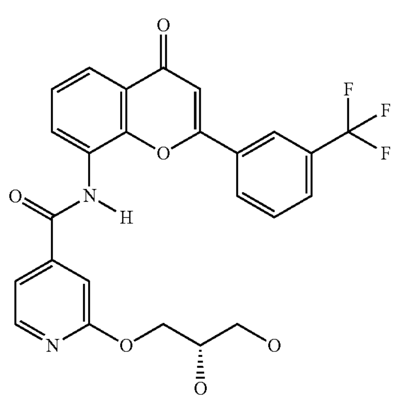 [SMILES: O=C(Nc1cccc2c(=O)cc(-c3cccc(C(F)(F)F)c3)oc12)c1ccnc(OC[C@@H](O)CO)c1] | C | B |

TABLE 1-continued

| Compd No | [M + H]+ | Structure | EC1.5 μM | % Fold Act. |
|---|---|---|---|---|
| 246 | 501 | 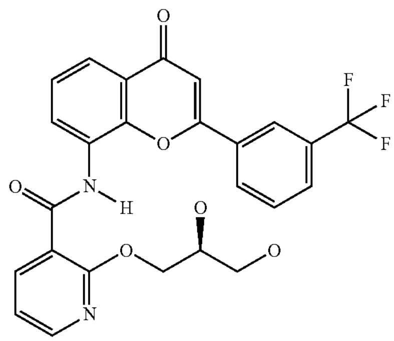 [SMILES: O=C(Nc1cccc2c(=O)cc(-c3cccc(C(F)(F)F)c3)oc12)c1cccnc1OC[C@@H](O)CO] | B | B |
| 247 | 501 | 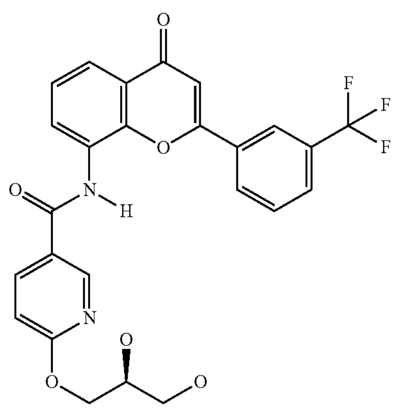 [SMILES: O=C(Nc1cccc2c(=O)cc(-c3cccc(C(F)(F)F)c3)oc12)c1ccc(OC[C@@H](O)CO)nc1] | C | B |
| 248 | 364 | 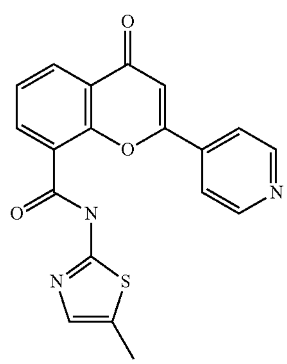 | C | B |
| 249 | 421 | 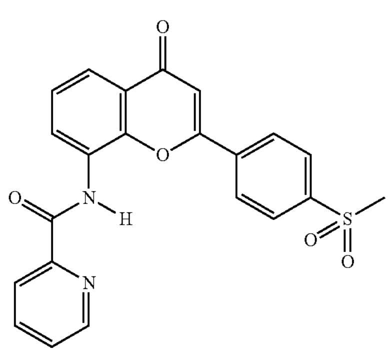 [SMILES: CS(=O)(=O)c1ccc(-c2cc(=O)c3cccc(NC(=O)c4ccccn4)c3o2)cc1] | C | B |

TABLE 1-continued

| Compd No | [M + H]+ | Structure | EC1.5 µM | % Fold Act. |
|---|---|---|---|---|
| 250 | 414 | *(structure)* | A | A |
| 251 | 411 | *(structure)* | A | A |
| 252 | 412 | *(structure)* | A | A |
| 253 | 412 | *(structure)* | A | A |

TABLE 1-continued

| Compd No | [M + H]+ | Structure | EC1.5 µM | % Fold Act. |
|---|---|---|---|---|
| 254 | 374 | 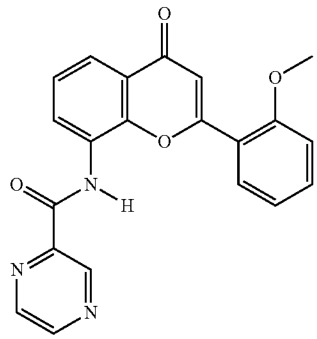 [SMILES: COc1ccccc1-c1cc(=O)c2cccc(NC(=O)c3cnccn3)c2o1] | C | B |
| 255 | 379 | 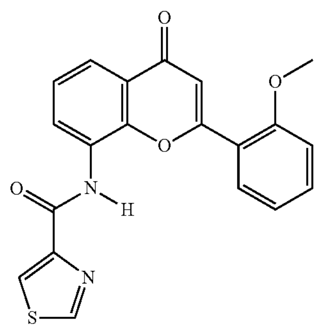 [SMILES: COc1ccccc1-c1cc(=O)c2cccc(NC(=O)c3cscn3)c2o1] | C | B |
| 256 | 414 | 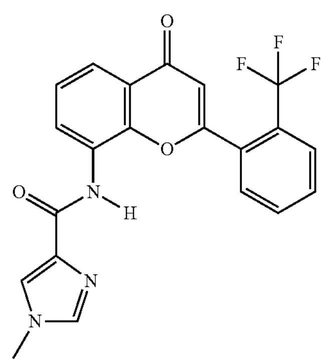 [SMILES: Cn1cnc(C(=O)Nc2cccc3c(=O)cc(-c4ccccc4C(F)(F)F)oc23)c1] | A | A |
| 257 | 414 | 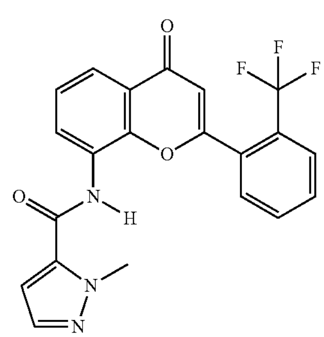 [SMILES: Cn1nccc1C(=O)Nc1cccc2c(=O)cc(-c3ccccc3C(F)(F)F)oc12] | A | A |

TABLE 1-continued

| Compd No | [M + H]+ | Structure | EC1.5 μM | % Fold Act. |
|---|---|---|---|---|
| 258 | 411 | 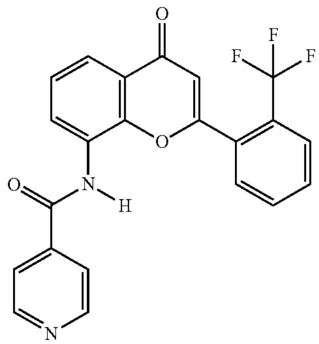 | B | A |
| 259 | 414 | 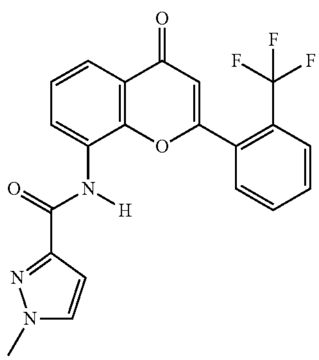 [SMILES: Cn1ccc(C(=O)Nc2cccc3c(=O)cc(-c4ccccc4C(F)(F)F)oc23)n1] | B | A |
| 260 | 412 | 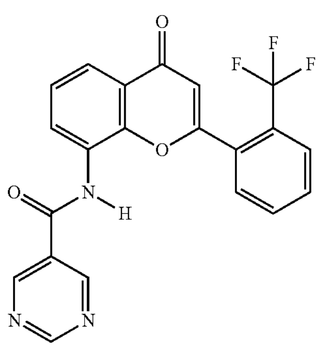 | C | B |
| 261 | 412 | 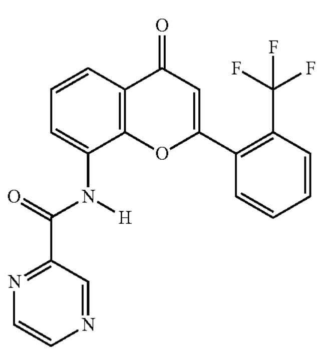 | A | A |

TABLE 1-continued

| Compd No | [M + H]+ | Structure | EC1.5 μM | % Fold Act. |
|---|---|---|---|---|
| 262 | 411 | 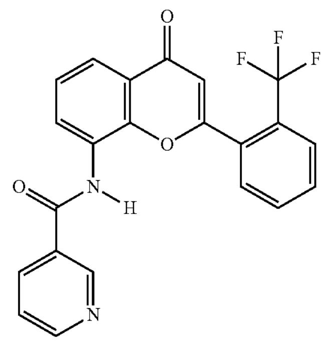 | B | B |
| 263 | 410 | 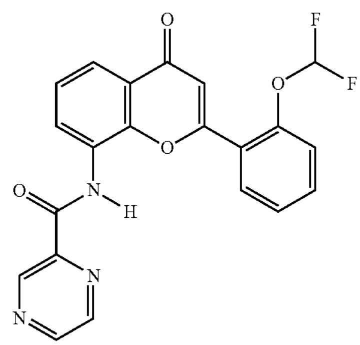 [SMILES: O=C(Nc1cccc2c(=O)cc(-c3ccccc3OC(F)F)oc12)c1cnccn1] | C | B |
| 264 | 415 | 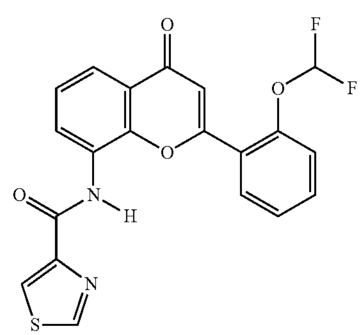 [SMILES: O=C(Nc1cccc2c(=O)cc(-c3ccccc3OC(F)F)oc12)c1cscn1] | C | B |
| 265 | 422 | 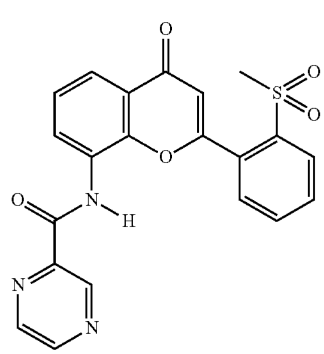 [SMILES: CS(=O)(=O)c1ccccc1-c1cc(=O)c2cccc(NC(=O)c3cnccn3)c2o1] | C | B |

TABLE 1-continued

| Compd No | [M + H]+ | Structure | EC1.5 μM | % Fold Act. |
|---|---|---|---|---|
| 266 | 427 | 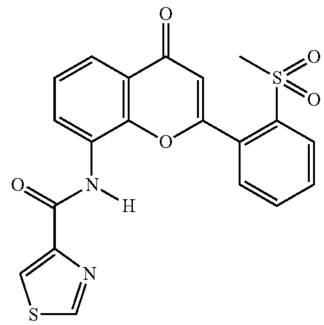 [SMILES: CS(=O)(=O)c1ccccc1-c1cc(=O)c2cccc(NC(=O)c3cscn3)c2o1] | B | B |
| 267 | 417 | 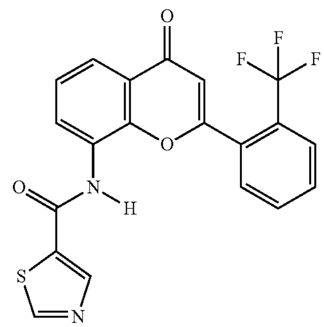 [SMILES: O=C(Nc1cccc2c(=O)cc(-c3ccccc3C(F)(F)F)oc12)c1cncs1] | B | A |
| 268 | 415 | 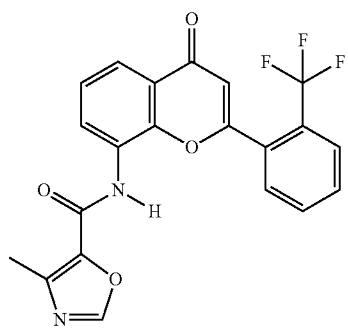 [SMILES: Cc1ncoc1C(=O)Nc1cccc2c(=O)cc(-c3ccccc3C(F)(F)F)oc12] | A | A |
| 269 | 414 | 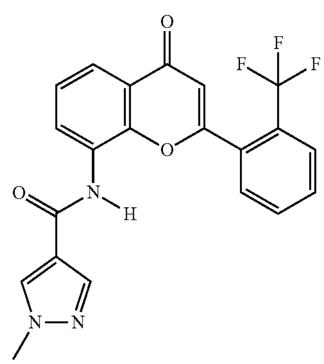 [SMILES: Cn1cc(C(=O)Nc2cccc3c(=O)cc(-c4ccccc4C(F)(F)F)oc23)cn1] | B | A |

TABLE 1-continued
| Compd No | [M + H]+ | Structure | EC1.5 μM | % Fold Act. |
|---|---|---|---|---|
| 270 | 397 | 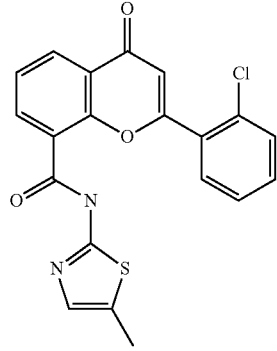 [SMILES: Cc1cnc(NC(=O)c2cccc3c(=O)cc(-c4ccccc4Cl)oc23)s1] | C | B |
| 271 | 381 | 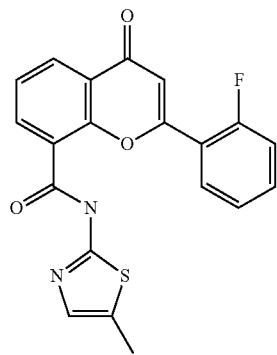 [SMILES: Cc1cnc(NC(=O)c2cccc3c(=O)cc(-c4ccccc4F)oc23)s1] | C | B |
| 272 | 401 | 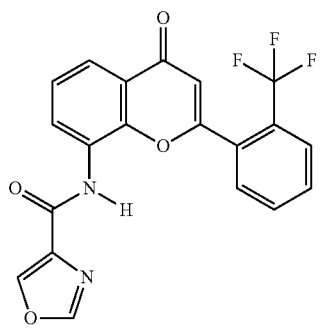 [SMILES: O=C(Nc1cccc2c(=O)cc(-c3ccccc3C(F)(F)F)oc12)c1cocn1] | B | A |
| 273 | 358 | 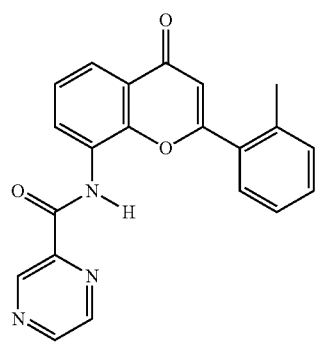 | A | A |

TABLE 1-continued
| Compd No | [M + H]+ | Structure | EC1.5 μM | % Fold Act. |
|---|---|---|---|---|
| 274 | 363 | 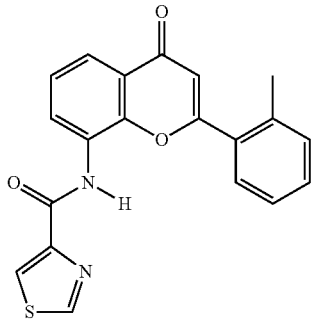 [SMILES: Cc1ccccc1-c1cc(=O)c2cccc(NC(=O)c3cscn3)c2o1] | C | B |
| 275 | 447 | 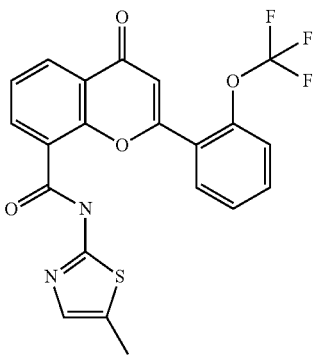 [SMILES: Cc1cnc(NC(=O)c2cccc3c(=O)cc(-c4ccccc4OC(F)(F)F)oc23)s1] | C | B |
| 276 | 431 | 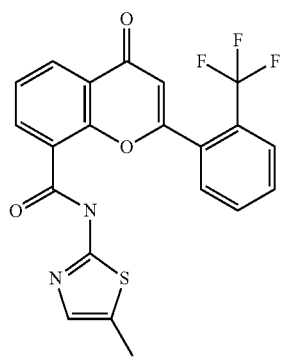 | C | B |
| 277 | 414 | 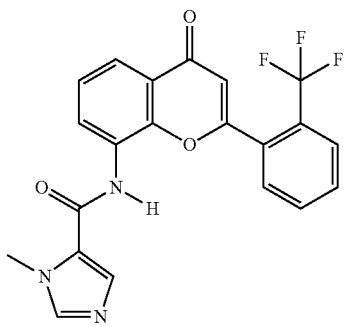 [SMILES: Cn1cncc1C(=O)Nc1cccc2c(=O)cc(-c3ccccc3C(F)(F)F)oc12] | B | A |

TABLE 1-continued
| Compd No | [M + H]+ | Structure | EC1.5 μM | % Fold Act. |
|---|---|---|---|---|
| 278 | 362 | 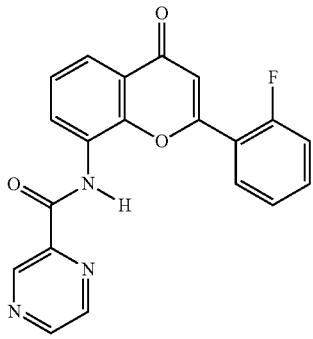 [SMILES: O=C(Nc1cccc2c(=O)cc(-c3ccccc3F)oc12)c1cnccn1] | C | B |
| 279 | 367 | 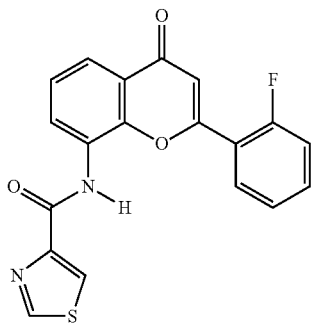 [SMILES: O=C(Nc1cccc2c(=O)cc(-c3ccccc3F)oc12)c1cscn1] | C | B |
| 280 | 378 | 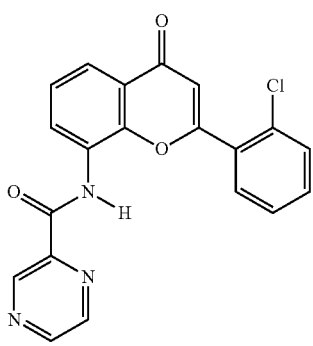 | A | A |
| 281 | 383 | 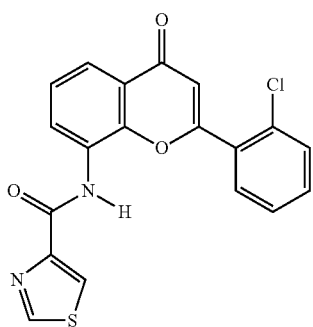 | A | A |

TABLE 1-continued

| Compd No | [M + H]+ | Structure | EC1.5 μM | % Fold Act. |
|---|---|---|---|---|
| 282 | 394 | 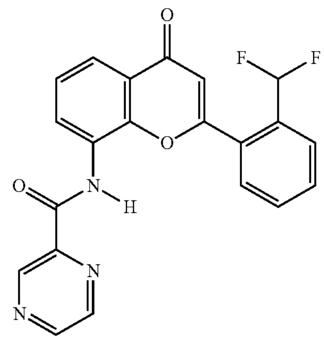 [SMILES: O=C(Nc1cccc2c(=O)cc(-c3ccccc3C(F)F)oc12)c1cnccn1] | A | A |
| 283 | 399 | 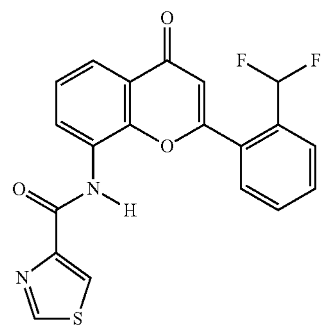 [SMILES: O=C(Nc1cccc2c(=O)cc(-c3ccccc3C(F)F)oc12)c1cscn1] | A | A |
| 284 | 413 | 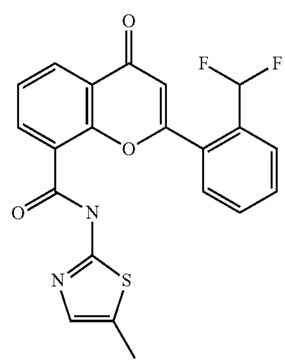 [SMILES: Cc1cnc(NC(=O)c2cccc3c(=O)cc(-c4ccccc4C(F)F)oc23)s1] | C | B |
| 285 | 405 | 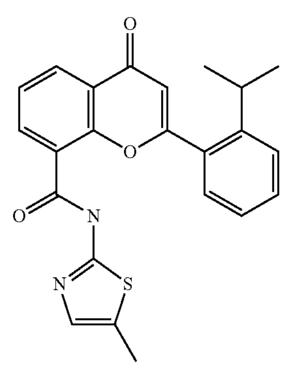 [SMILES: Cc1cnc(NC(=O)c2cccc3c(=O)cc(-c4ccccc4C(C)C)oc23)s1] | C | B |

TABLE 1-continued
| Compd No | [M + H]+ | Structure | EC1.5 µM | % Fold Act. |
|---|---|---|---|---|
| 286 | 386 | 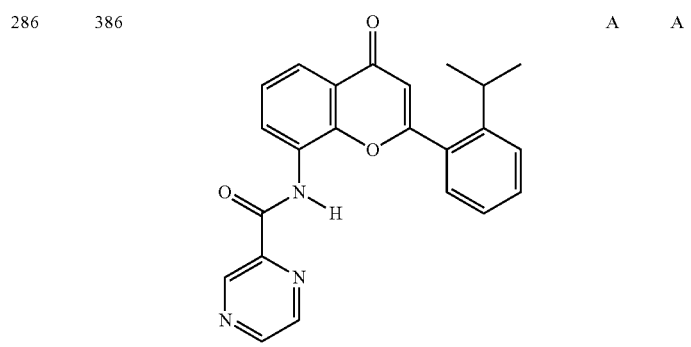 | A | A |
| 287 | 391 | 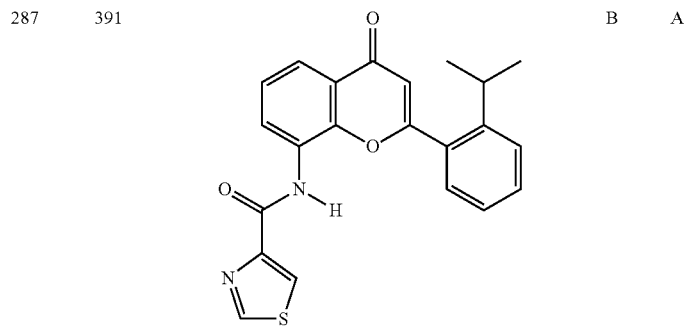 | B | A |
| 288 | 380 | 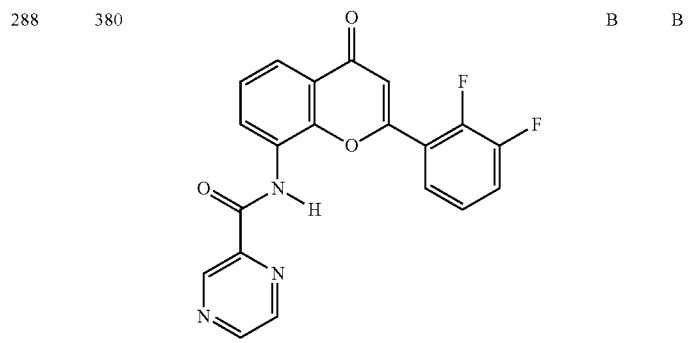 | B | B |
| 289 | 385 | 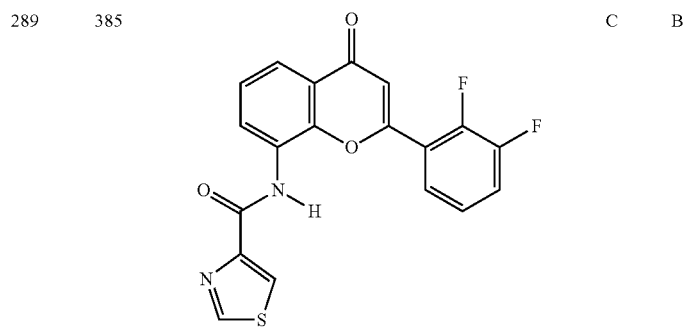 | C | B |

TABLE 1-continued
| Compd No | [M + H]+ | Structure | EC1.5 μM | % Fold Act. |
|---|---|---|---|---|
| 290 | 380 | 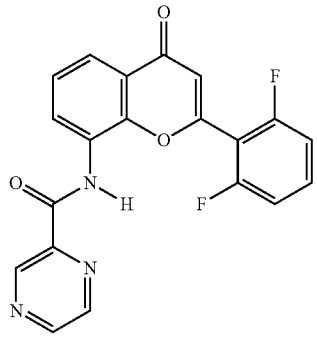 [SMILES: O=C(Nc1cccc2c(=O)cc(-c3c(F)cccc3F)oc12)c1cnccn1] | C | B |
| 291 | 385 | 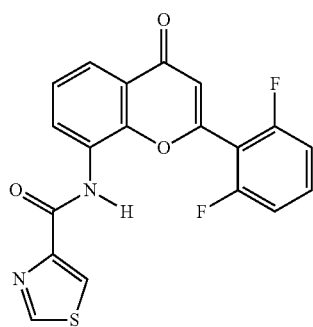 [SMILES: O=C(Nc1cccc2c(=O)cc(-c3c(F)cccc3F)oc12)c1cscn1] | B | B |
| 292 | 380 | 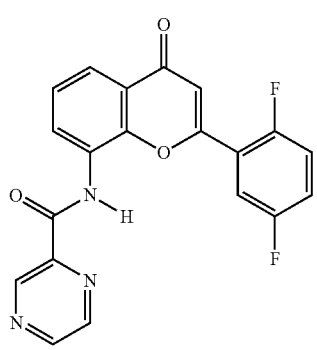 [SMILES: O=C(Nc1cccc2c(=O)cc(-c3cc(F)ccc3F)oc12)c1cnccn1] | C | B |
| 293 | 385 | 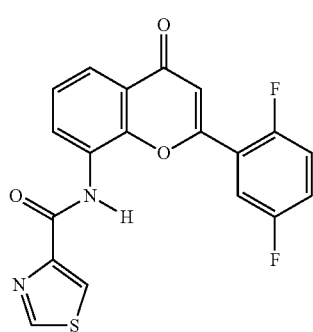 [SMILES: O=C(Nc1cccc2c(=O)cc(-c3cc(F)ccc3F)oc12)c1cscn1] | C | B |

TABLE 1-continued
| Compd No | [M + H]+ | Structure | EC1.5 µM | % Fold Act. |
|---|---|---|---|---|
| 294 | 429 | 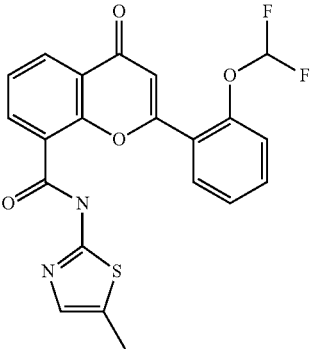 [SMILES: Cc1cnc(NC(=O)c2cccc3c(=O)cc(-c4ccccc4OC(F)F)oc23)s1] | B | B |
| 295 | 399 | 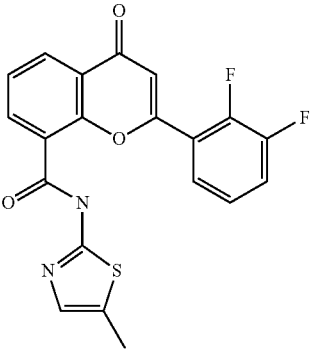 [SMILES: Cc1cnc(NC(=O)c2cccc3c(=O)cc(-c4cccc(F)c4F)oc23)s1] | C | B |
| 296 | 396 | 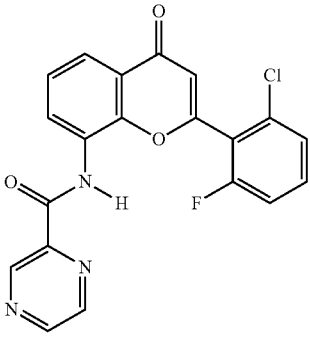 [SMILES: O=C(Nc1cccc2c(=O)cc(-c3c(F)cccc3Cl)oc12)c1cnccn1] | A | A |
| 297 | 401 | 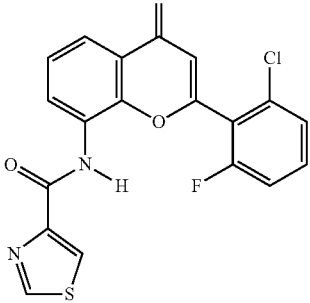 | B | A |

TABLE 1-continued
| Compd No | [M + H]+ | Structure | EC1.5 μM | % Fold Act. |
|---|---|---|---|---|
| 298 | 396 | 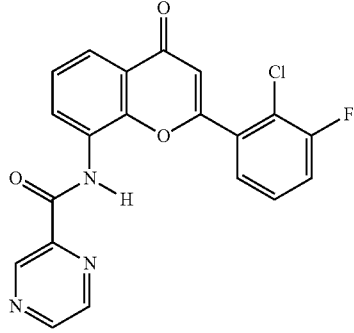 | B | B |
| 299 | 401 | 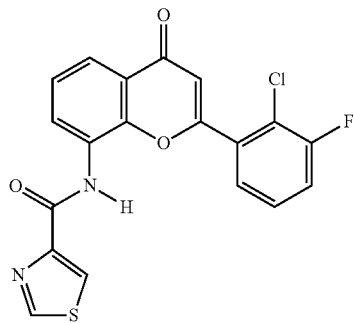 [SMILES: O=C(Nc1cccc2c(=O)cc(-c3cccc(F)c3Cl)oc12)c1cscn1] | C | B |
| 300 | 396 | 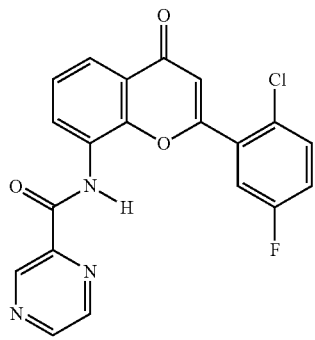 | C | B |
| 301 | 401 | 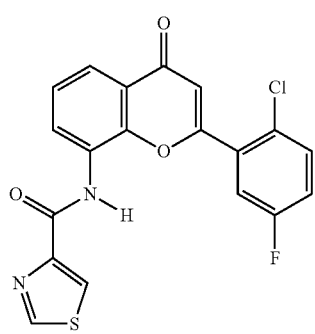 [SMILES: O=C(Nc1cccc2c(=O)cc(-c3cc(F)ccc3Cl)oc12)c1cscn1] | C | B |

TABLE 1-continued

| Compd No | [M + H]+ | Structure | EC1.5 μM | % Fold Act. |
|---|---|---|---|---|
| 302 | 412 | 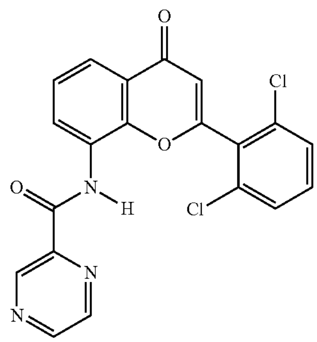 | B | A |
| 303 | 417 | 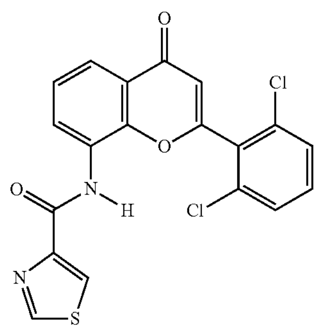 [SMILES: O=C(Nc1cccc2c(=O)cc(-c3c(Cl)cccc3Cl)oc12)c1cscn1] | B | A |
| 304 | 441 | 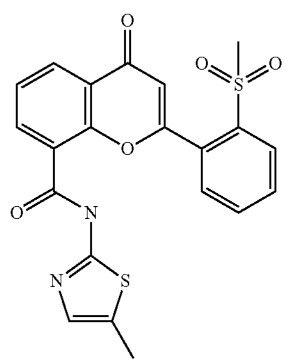 [SMILES: Cc1cnc(NC(=O)c2cccc3c(=O)cc(-c4ccccc4S(C)(=O)=O)oc23)s1] | C | B |
| 305 | 432 | 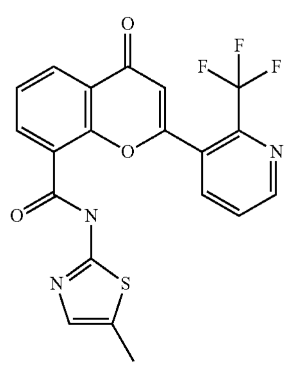 [SMILES: Cc1cnc(NC(=O)c2cccc3c(=O)cc(-c4cccnc4C(F)(F)F)oc23)s1] | C | B |

TABLE 1-continued
| Compd No | [M + H]+ | Structure | EC1.5 μM | % Fold Act. |
|---|---|---|---|---|
| 306 | 413 | 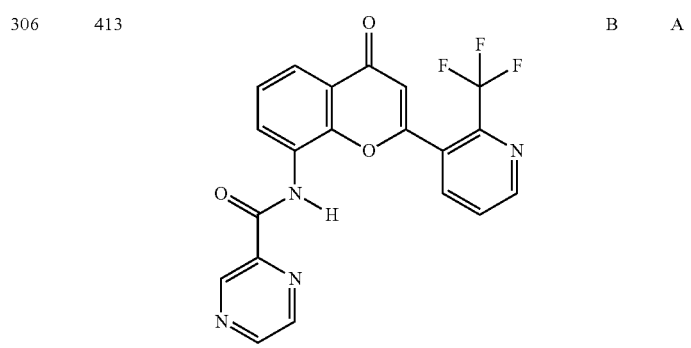 | B | A |
| 307 | 418 | 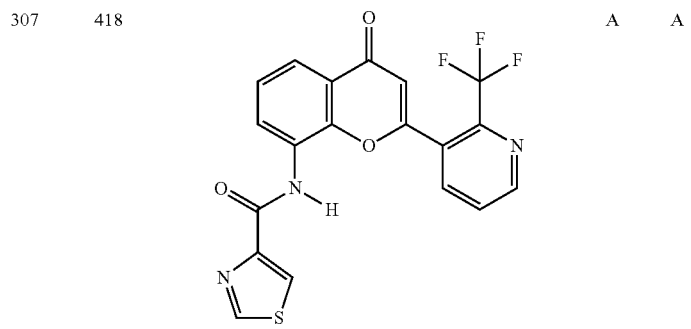 | A | A |
| 308 | 413 | 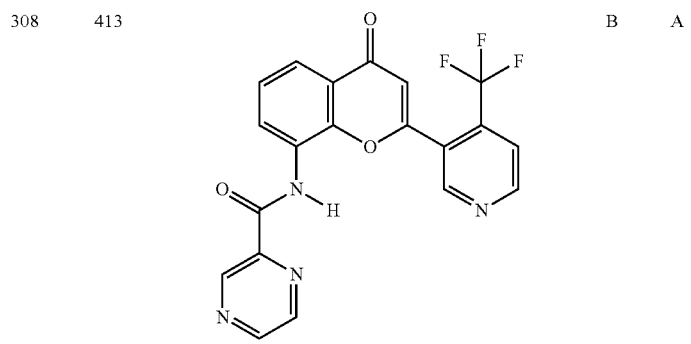 | B | A |
| 309 | 418 | 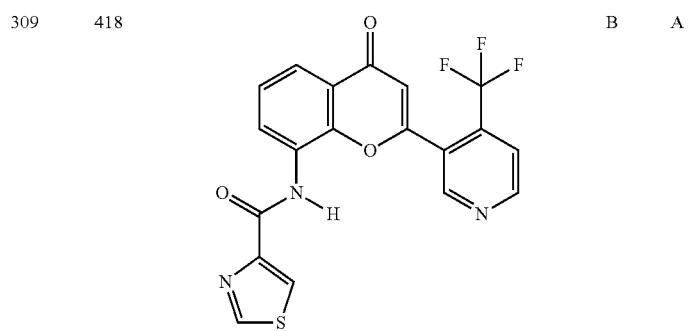 | B | A |

TABLE 1-continued
| Compd No | [M + H]+ | Structure | EC1.5 µM | % Fold Act. |
|---|---|---|---|---|
| 310 | 432 | 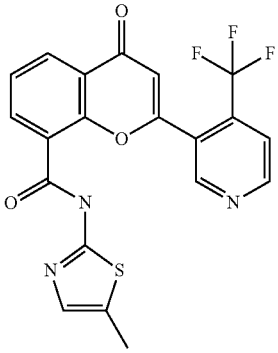 | B | B |
| 311 | 495 | 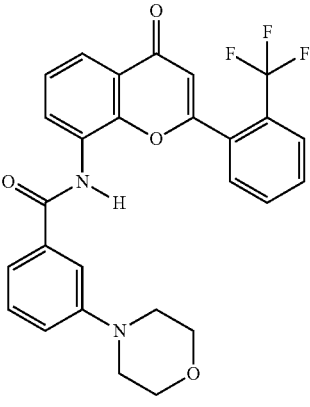 | B | A |
| 312 | 479 | 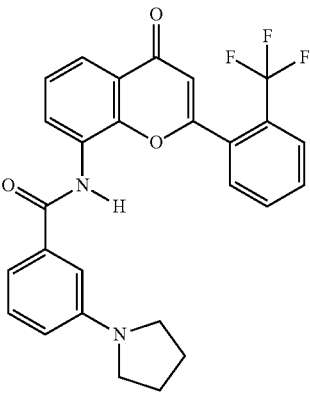 [SMILES: O=C(Nc1cccc2c(=O)cc(-c3ccccc3C(F)(F)F)oc12)c1cccc(N2CCCC2)c1] | B | A |
| 313 | 417 | 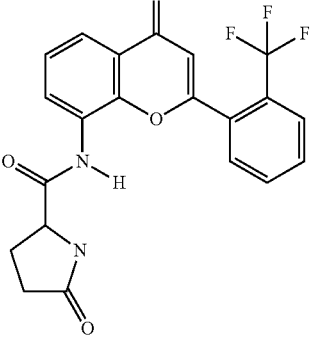 | B | A |

TABLE 1-continued
| Compd No | [M + H]+ | Structure | EC1.5 µM | % Fold Act. |
|---|---|---|---|---|
| 315 | 510 | 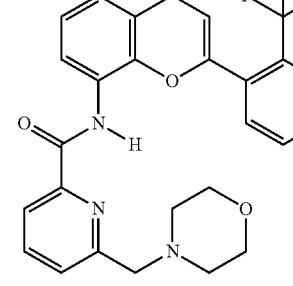 | A | A |
| 316 | 497 | 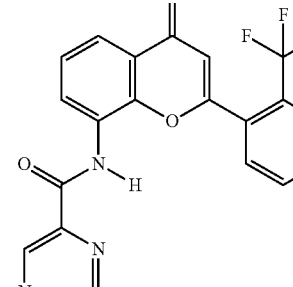 | A | A |
| 317 | 417 | 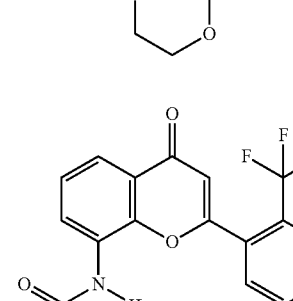 | B | B |
| 318 | 501 | 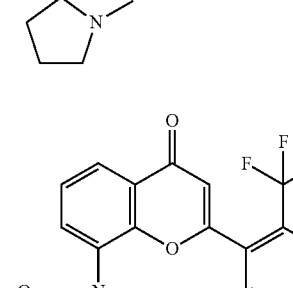 | A | A |

TABLE 1-continued

| Compd No | [M + H]+ | Structure | EC1.5 μM | % Fold Act. |
|---|---|---|---|---|
| 319 | 463 | 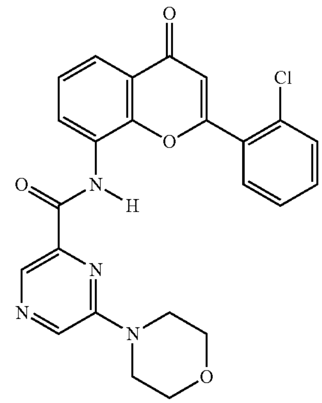 | A | A |
| 320 | 494 | 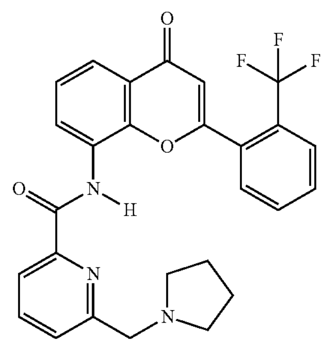 [SMILES: O=C(Nc1cccc2c(=O)cc(-c3ccccc3C(F)(F)F)oc12)c1cccc(CN2CCCC2)n1] | A | A |
| 321 | 501 | 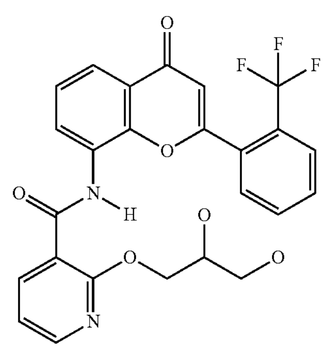 [SMILES: O=C(Nc1cccc2c(=O)cc(-c3ccccc3C(F)(F)F)oc12)c1cccnc1OCC(O)CO] | B | A |
| 322 | 496 | 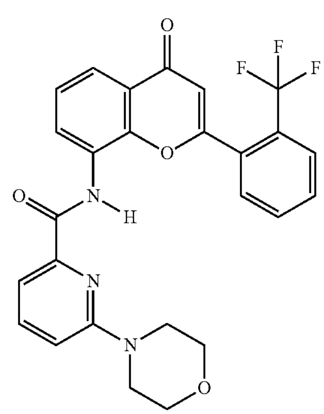 [SMILES: O=C(Nc1cccc2c(=O)cc(-c3ccccc3C(F)(F)F)oc12)c1cccc(N2CCOCC2)n1] | A | A |

TABLE 1-continued

| Compd No | [M + H]+ | Structure | EC1.5 μM | % Fold Act. |
|---|---|---|---|---|
| 323 | 480 | 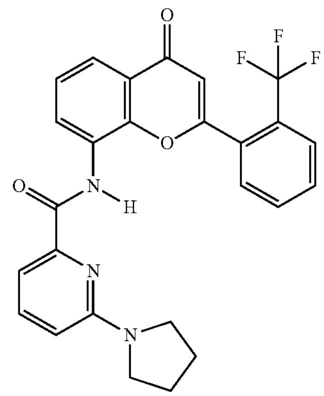 | A | A |
| 324 | 462 | 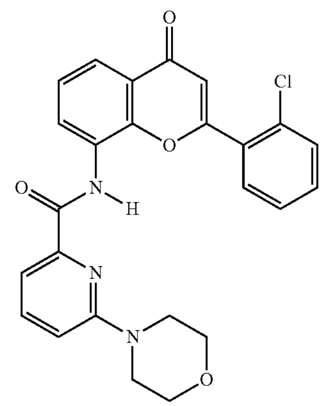 [SMILES: O=C(Nc1cccc2c(=O)cc(-c3ccccc3Cl)oc12)c1cccc(N2CCOCC2)n1] | A | A |
| 325 | 446 | 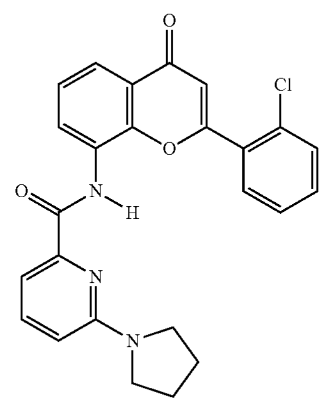 [SMILES: O=C(Nc1cccc2c(=O)cc(-c3ccccc3Cl)oc12)c1cccc(N2CCCC2)n1] | A | A |
| 326 | 447 | 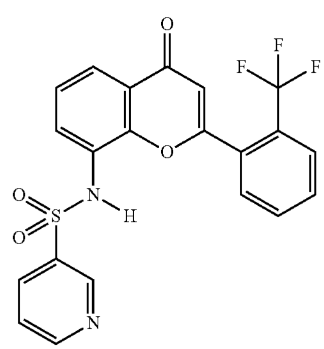 [SMILES: O=c1cc(-c2ccccc2C(F)(F)F)oc2c(NS(=O)(=O)c3cccnc3)cccc12] | C | B |

TABLE 1-continued
| Compd No | [M + H]+ | Structure | EC1.5 μM | % Fold Act. |
|---|---|---|---|---|
| 327 | 460 | 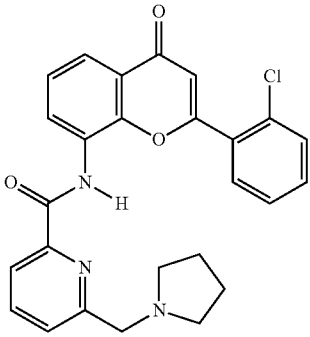 [SMILES: O=C(Nc1cccc2c(=O)cc(-c3ccccc3Cl)oc12)c1cccc(CN2CCCC2)n1] | A | A |
| 328 | 509 | 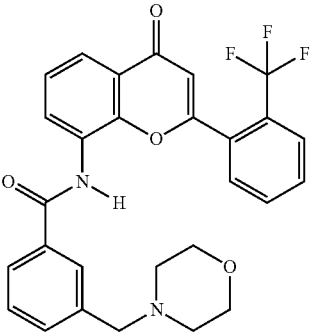 [SMILES: O=C(Nc1cccc2c(=O)cc(-c3ccccc3C(F)(F)F)oc12)c1cccc(CN2CCOCC2)c1] | B | A |
| 329 | 445 | 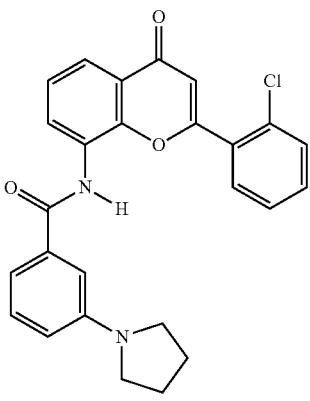 | A | A |
| 330 | 475 | 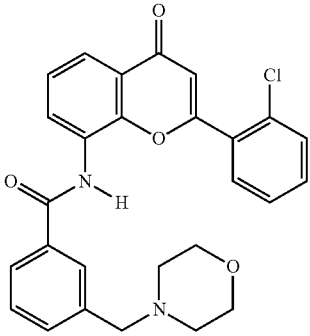 | B | A |

TABLE 1-continued
| Compd No | [M + H]+ | Structure | EC1.5 μM | % Fold Act. |
|---|---|---|---|---|
| 331 | 476 | 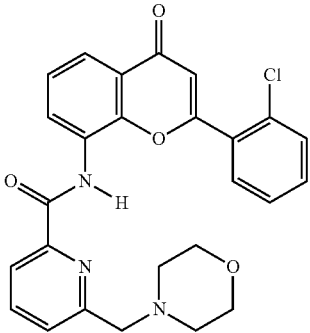 [SMILES: O=C(Nc1cccc2c(=O)cc(-c3ccccc3Cl)oc12)c1cccc(CN2CCOCC2)n1] | A | A |
| 332 | 467 | 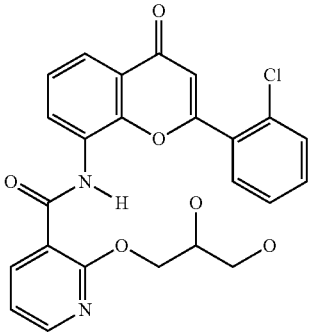 [SMILES: O=C(Nc1cccc2c(=O)cc(-c3ccccc3Cl)oc12)c1cccnc1OCC(O)CO] | B | A |
| 333 | 459 | 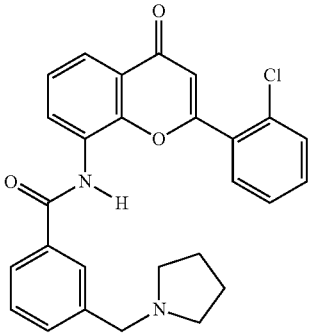 | B | A |
| 334 | 467 | 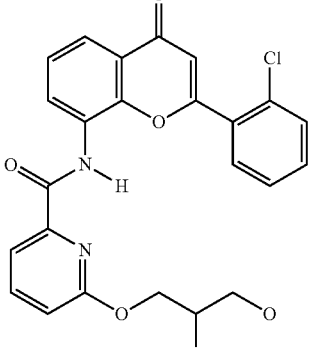 | A | A |

TABLE 1-continued

| Compd No | [M + H]+ | Structure | EC1.5 µM | % Fold Act. |
|---|---|---|---|---|
| 335 | 378 | 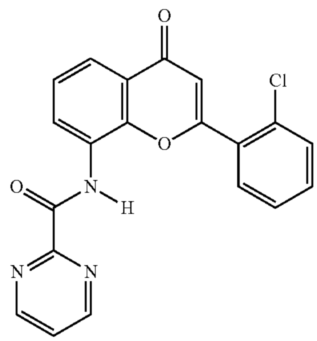 | A | A |
| 336 | 461 | 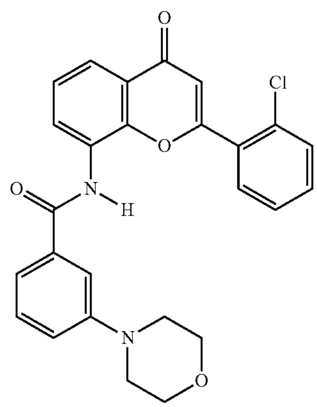 | B | A |
| 337 | 380 | 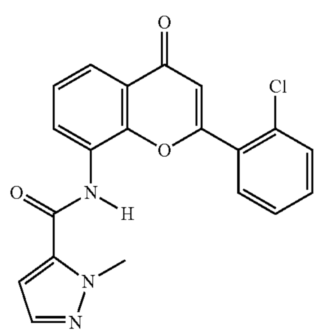 [SMILES: Cn1nccc1C(=O)Nc1cccc2c(=O)cc(-c3ccccc3Cl)oc12] | A | A |
| 338 | 483 | 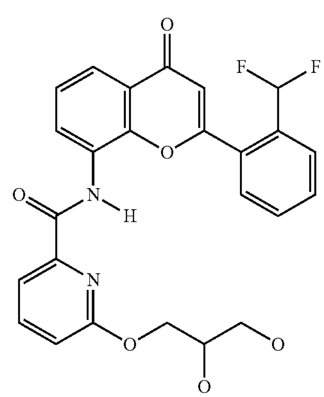 [SMILES: O=C(Nc1cccc2c(=O)cc(-c3ccccc3C(F)F)oc12)c1cccc(OCC(O)CO)n1] | A | A |

TABLE 1-continued

| Compd No | [M + H]+ | Structure | EC1.5 µM | % Fold Act. |
|---|---|---|---|---|
| 339 | 492 | 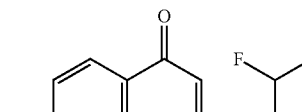 | A | A |

In one embodiment, the compound of this invention is selected from any one of compound numbers 227, 231, 234, 250, 251, 252, 253, 256, 257, 261, 268, 273, 280, 281, 282, 283, 286, 296, 307, 315, 316, 318, 319, 320, 322, 323, 324, 325, 327, 329, 331, 334, 335, 337, 338, or 339 from the table above. In one aspect, the compound of this invention is selected from any one of compound numbers 227, 231, 234, 251, 252, 253, 257, 261, 280, 296, 315, 323, or 337 from the table above.

EQUIVALENTS

The present invention provides among other things sirtuin-activating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

The invention claimed is:
1. A compound of the formula (II):

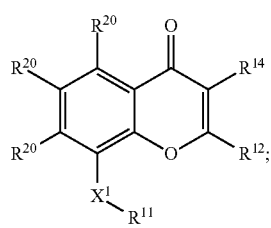

(II)

or a salt thereof:
wherein:
each $R^{20}$ is independently selected from hydrogen, halo, —C≡N, fluoro-substituted $C_1$-$C_2$ alkyl, —O—($C_1$-$C_2$) fluoro-substituted alkyl, —S—($C_1$-$C_2$) fluoro-substituted alkyl, $C_1$-$C_4$ alkyl, —S—($C_1$-$C_4$) alkyl, $C_3$-$C_7$ cycloalkyl, —($C_1$-$C_2$) alkyl-N($R^{13}$)($R^{13}$), —O—$CH_2CH(OH)CH_2OH$, —O—($C_1$-$C_3$)alkyl-N($R^{13}$)($R^{13}$), and —N($R^{13}$)($R^{13}$);
$R^{11}$ is selected from:

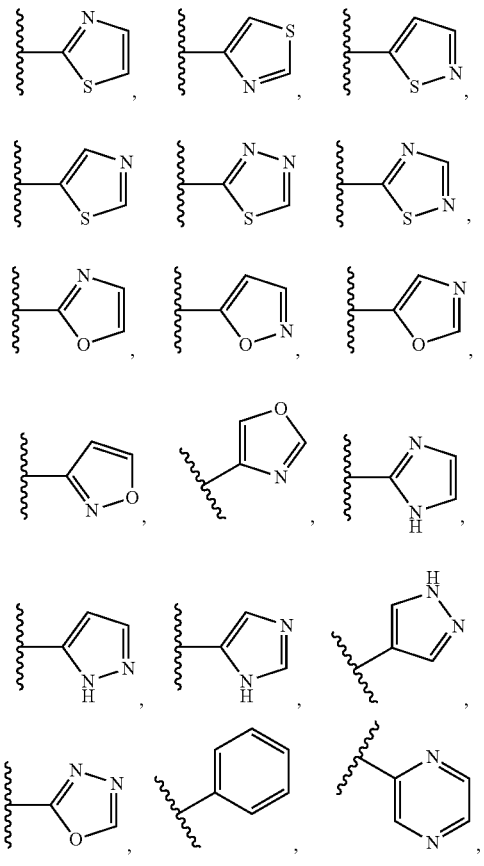

or
$R^{11}$ is selected from:
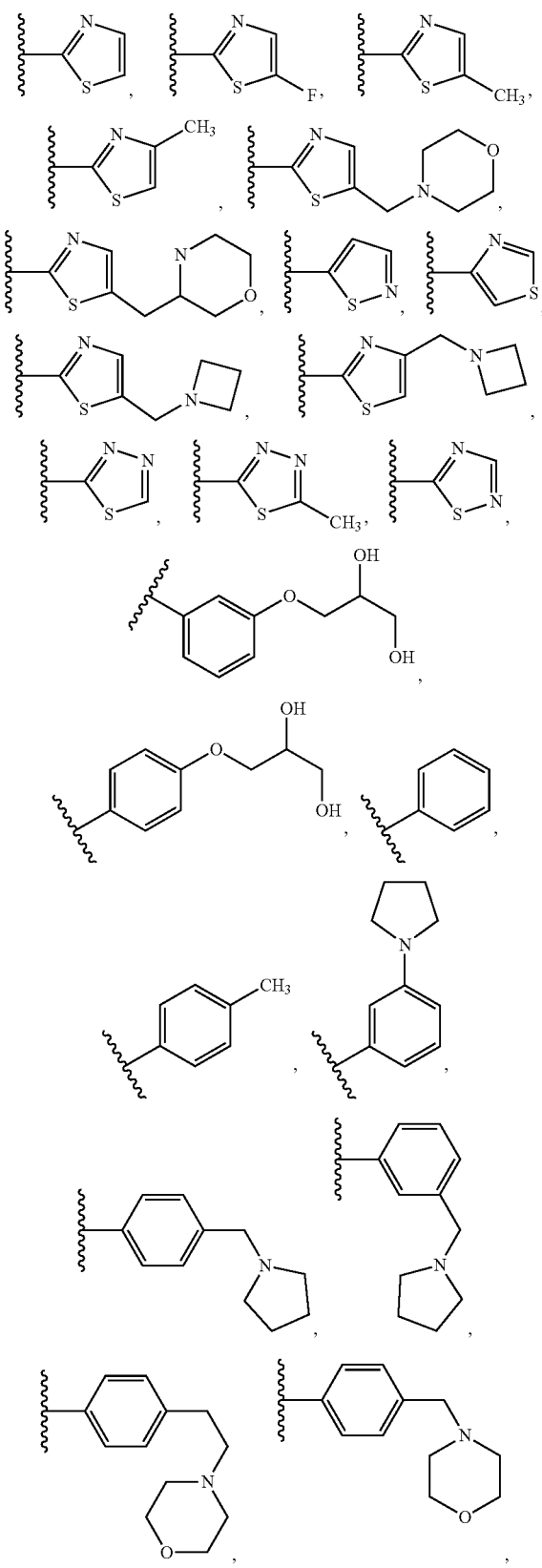
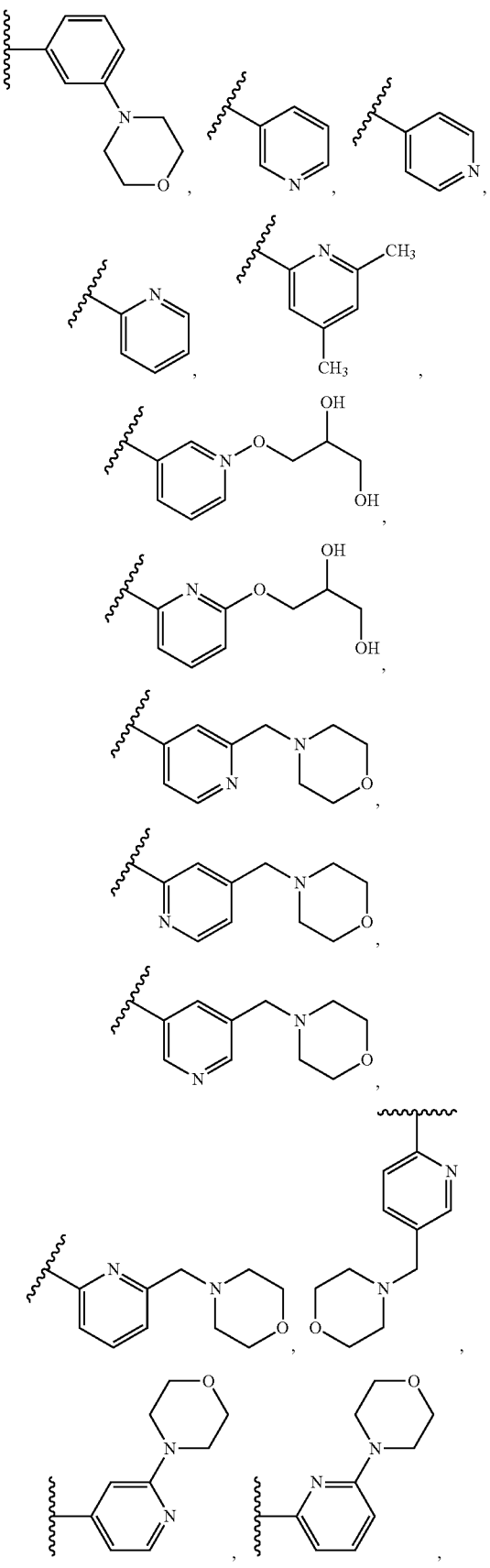
-continued

-continued
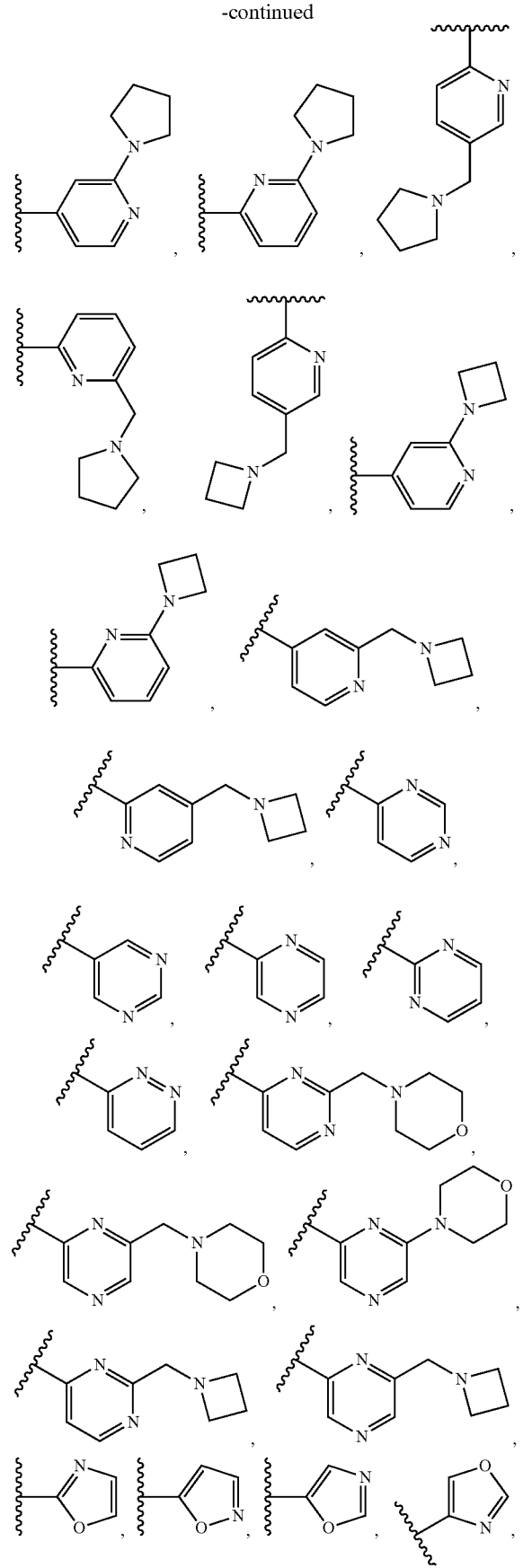
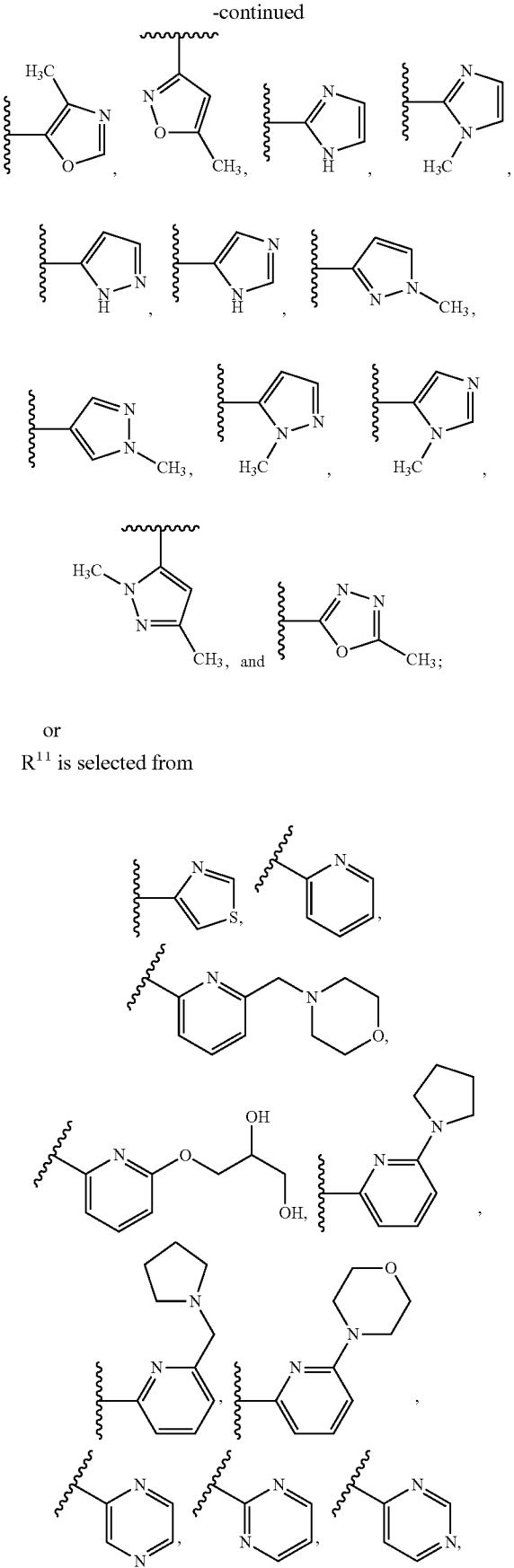
or
R[11] is selected from

-continued

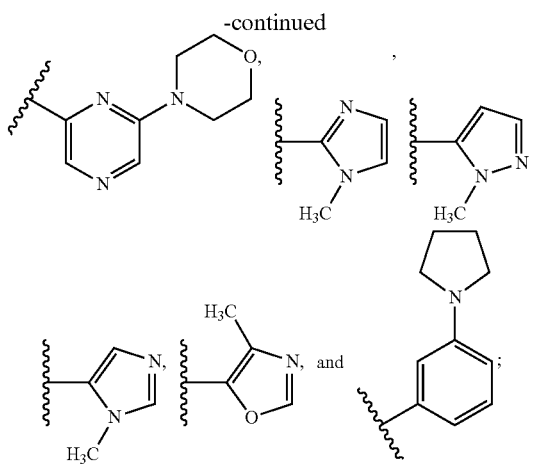

wherein:
R$^{11}$ is optionally substituted with one to two substitutents independently selected from halo, —C≡N, C$_1$-C$_4$ alkyl, =O, C$_3$-C$_7$ cycloalkyl, fluoro-substituted C$_1$-C$_4$ alkyl, —O—R$^{13}$, —S—R$^{13}$, —(C$_1$-C$_4$ alkyl)-N(R$^{13}$)(R$^{13}$), —N(R$^{13}$)(R$^{13}$), —O—(C$_1$-C$_4$ alkyl)-N(R$^{13}$)(R$^{13}$), —(C$_1$-C$_4$ alkyl)-O—(C$_1$-C$_4$ alkyl)-N(R$^{13}$)(R$^{13}$), —C(O)—N(R$^{13}$)(R$^{13}$), and —(C$_1$-C$_4$ alkyl)-C(O)—N(R$^{13}$)(R$^{13}$), and when R$^{11}$ is phenyl, R$^{11}$ is also optionally substituted with 3,4-methylenedioxy, fluoro-substituted 3,4-methylenedioxy, 3,4-ethylenedioxy, fluoro-substituted 3,4-ethylenedioxy, O-(saturated heterocycle), fluoro-substituted-O-(saturated heterocycle), or C$_1$-C$_4$ alkyl-substituted O-(saturated heterocycle);

wherein:
each R$^{13}$ is independently selected from hydrogen and —C$_1$-C$_4$ alkyl; or two R$^{13}$ are taken together with the nitrogen atom to which they are bound to form a 4- to 8-membered saturated heterocycle optionally comprising one additional heteroatomic unit selected from NH, S, S(=O), S(=O)$_2$, and O;

wherein:
when R$^{13}$ is alkyl, the alkyl is optionally substituted with one or more substituents selected from —OH, fluoro, —NH$_2$, —NH(C$_1$-C$_4$ alkyl), —N(C$_1$-C$_4$ alkyl)$_2$, —NH(CH$_2$CH$_2$OCH$_3$), and —N(CH$_2$CH$_2$OCH$_3$)$_2$ and when two R$^{13}$ are taken together with the nitrogen atom to which they are bound to form a 4- to 8-membered saturated heterocycle, the saturated heterocycle is optionally substituted at any carbon atom with —OH, —C$_1$-C$_4$ alkyl, fluoro, —NH$_2$, —NH(C$_1$-C$_4$ alkyl), —N(C$_1$-C$_4$ alkyl)$_2$, —NH(CH$_2$CH$_2$OCH$_3$), or —N(CH$_2$CH$_2$OCH$_3$)$_2$, and optionally substituted at any substitutable nitrogen atom with —C$_1$-C$_4$ alkyl, fluoro-substituted C$_1$-C$_4$ alkyl, or —(CH$_2$)$_2$—O—CH$_3$;

R$^{12}$ is selected from a 5-7 membered aryl or heteroaryl other than optionally substituted tetrazolyl;

wherein:
R$^{12}$ is optionally substituted with one or more substitutents independently selected from halo, —C≡N, C$_1$-C$_4$ alkyl, C$_3$-C$_7$ cycloalkyl, C$_1$-C$_2$ fluoro-substituted alkyl, —O—R$^{13}$, —S—R$^{13}$, —S(O)—R$^{13}$, —S(O)$_2$—R$^{13}$, —(C$_1$-C$_4$ alkyl)-N(R$^{13}$)(R$^{13}$), —N(R$^{13}$)(R$^{13}$), —O—(C$_1$-C$_4$ alkyl)-N(R$^{13}$)(R$^{13}$), —(C$_1$-C$_4$ alkyl)-O—(C$_1$-C$_4$ alkyl)-N(R$^{13}$)(R$^{13}$), —C(O)—N(R$^{13}$)(R$^{13}$), —(C$_1$-C$_4$ alkyl)-C(O)—N(R$^{13}$)(R$^{13}$), —O-phenyl, phenyl, and a second heterocycle, and when R$^{12}$ is phenyl, R$^{12}$ may also be optionally substituted with 3,4-methylenedioxy, fluoro-substituted 3,4-methylenedioxy, 3,4-ethylenedioxy, or fluoro-substituted 3,4-ethylenedioxy, or —O-(saturated heterocycle), wherein any phenyl, second heterocycle or saturated heterocycle portion of a substituent of R$^{12}$ is optionally substituted with halo, —C≡N, C$_1$-C$_4$ alkyl, fluoro-substituted C$_1$-C$_2$ alkyl, —O—(C$_1$-C$_2$) fluoro-substituted alkyl, —O—(C$_1$-C$_4$) alkyl, —S—(C$_1$-C$_4$) alkyl, —S—(C$_1$-C$_2$) fluoro-substituted alkyl, —NH—(C$_1$-C$_4$) alkyl and —N—(C$_1$-C$_4$)$_2$ alkyl;

R$^{14}$ is selected from hydrogen, C$_1$-C$_4$ alkyl, C$_1$-C$_4$ fluoro-substituted alkyl, C$_1$-C$_4$ alkyl-N(R$^{13}$)(R$^{13}$), C$_1$-C$_4$ alkyl-C(O)—N(R$^{13}$)(R$^{13}$), C$_1$-C$_4$ alkyl-O—R$^{13}$, and C$_1$-C$_4$ alkyl-NR$^{13}$—C(O)R$^{13}$;

X$^1$ is —NH—C(=O)-†; wherein:
† represents where X$^1$ is bound to R$^{11}$; and
each of R$^{15}$ and R$^{16}$ is independently selected from hydrogen, C$_1$-C$_4$ alkyl, —CF$_3$ and (C$_1$-C$_3$ alkyl)-CF$_3$ wherein:
when R$^{14}$ is C$_1$-C$_4$ alkyl, R$^{12}$ is other than optionally substituted phenyl.

2. A compound which is selected from:

| Compd No | [M + H]+ | Structure |
|---|---|---|
| 227 | 417 | ![structure] |
| 231 | 428 | ![structure] |

-continued
| Compd No | [M + H]+ | Structure |
|---|---|---|
| 234 | 428 | 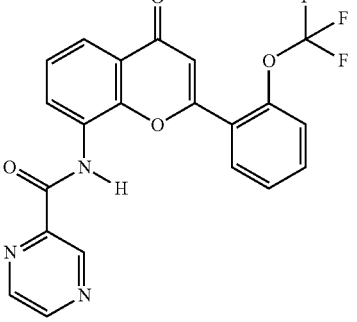 |
| 250 | 414 | 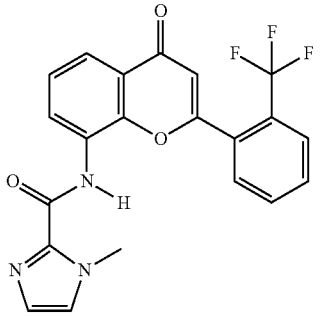 [SMILES: Cn1ccnc1C(=O)Nc1cccc2c(=O)cc(-c3ccccc3C(F)(F)F)oc12] |
| 251 | 411 | 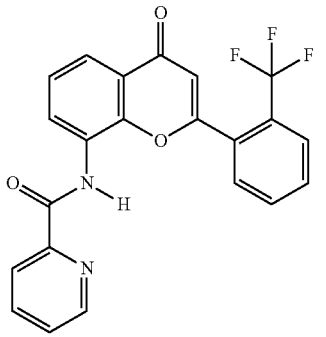 [SMILES: O=C(Nc1cccc2c(=O)cc(-c3ccccc3C(F)(F)F)oc12)c1ccccn1] |
| 252 | 412 | 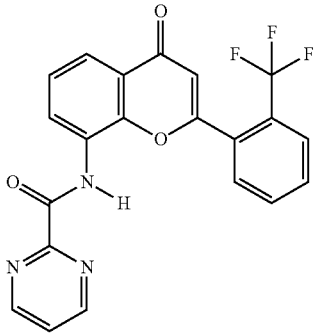 |
-continued
| Compd No | [M + H]+ | Structure |
|---|---|---|
| 253 | 412 | 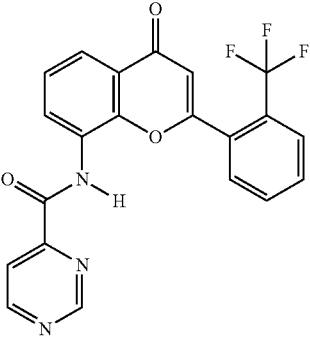 [SMILES: O=C(Nc1cccc2c(=O)cc(-c3ccccc3C(F)(F)F)oc12)c1ccncn1] |
| 256 | 414 | 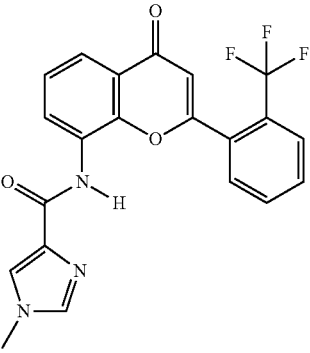 [SMILES: Cn1cnc(C(=O)Nc2cccc3c(=O)cc(-c4ccccc4C(F)(F)F)oc23)c1] |
| 257 | 414 | 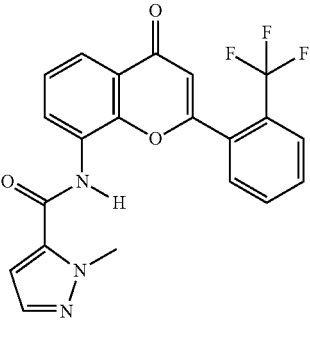 [SMILES: Cn1nccc1C(=O)Nc1cccc2c(=O)cc(-c3ccccc3C(F)(F)F)oc12] |
| 261 | 412 | 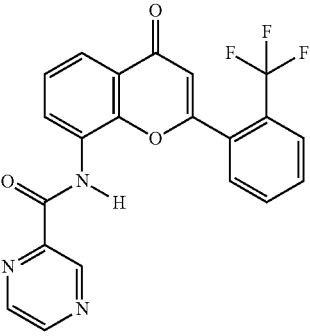 [SMILES: O=C(Nc1cccc2c(=O)cc(-c3ccccc3C(F)(F)F)oc12)c1cnccn1] |

-continued
| Compd No | [M + H]+ | Structure |
|---|---|---|
| 268 | 415 | 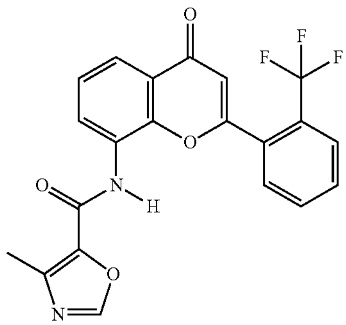 [SMILES: Cc1ncoc1C(=O)Nc1cccc2c(=O)cc(-c3ccccc3C(F)(F)F)oc12] |
| 273 | 358 | 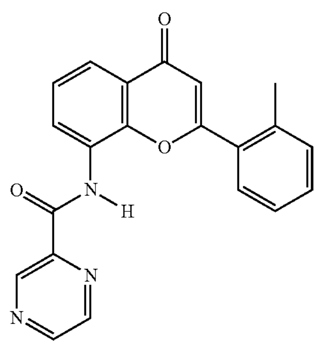 |
| 280 | 378 | 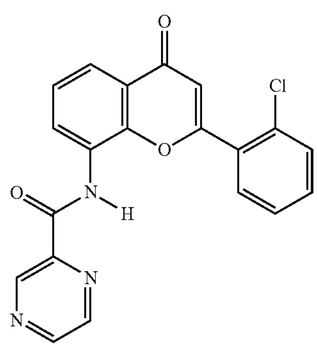 |
| 281 | 383 | 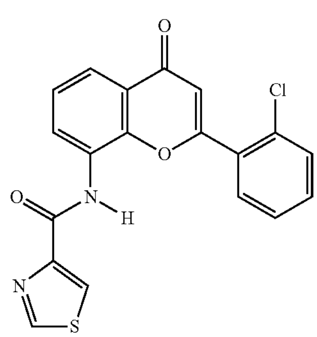 |
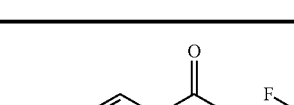
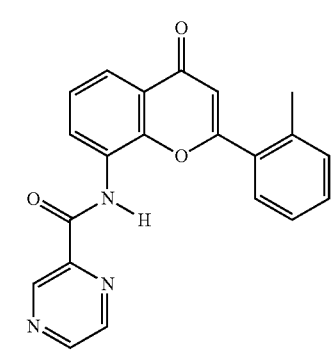
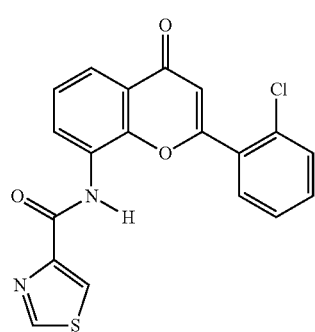 [SMILES: O=C(Nc1cccc2c(=O)cc(-c3ccccc3Cl)oc12)c1cscn1]
-continued
| Compd No | [M + H]+ | Structure |
|---|---|---|
| 282 | 394 | 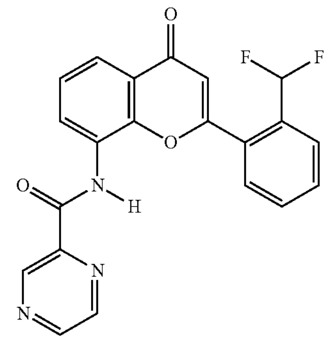 [SMILES: O=C(Nc1cccc2c(=O)cc(-c3ccccc3C(F)F)oc12)c1cnccn1] |
| 283 | 399 | 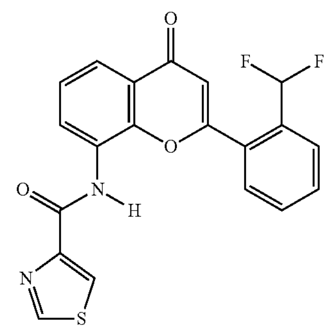 [SMILES: O=C(Nc1cccc2c(=O)cc(-c3ccccc3C(F)F)oc12)c1cscn1] |
| 286 | 386 | 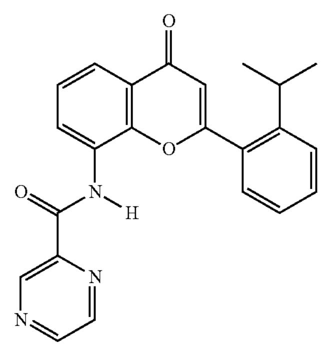 [SMILES: CC(C)c1ccccc1-c1cc(=O)c2cccc(NC(=O)c3cnccn3)c2o1] |
| 296 | 396 | 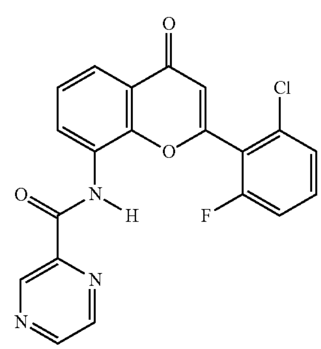 [SMILES: O=C(Nc1cccc2c(=O)cc(-c3c(F)cccc3Cl)oc12)c1cnccn1] |
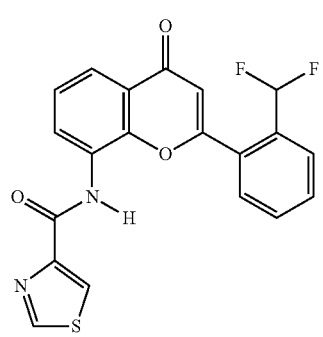
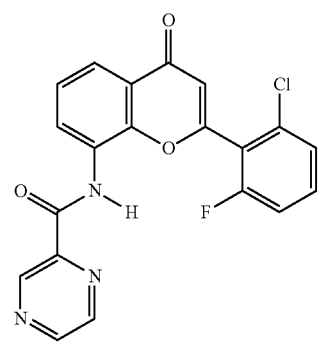

187
-continued
| Compd No | [M + H]+ | Structure |
|---|---|---|
| 307 | 418 | 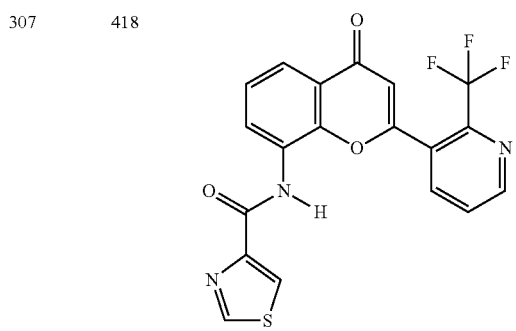 |
| 315 | 510 | 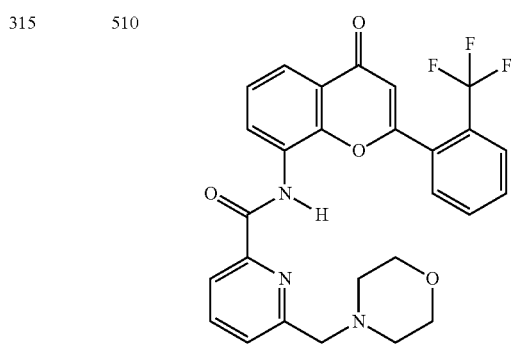 |
| 316 | 497 | 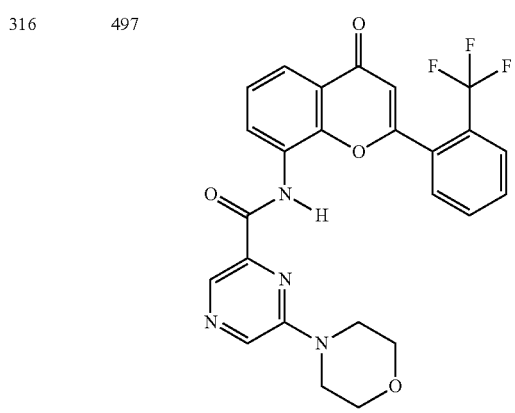 |
| 318 | 501 | 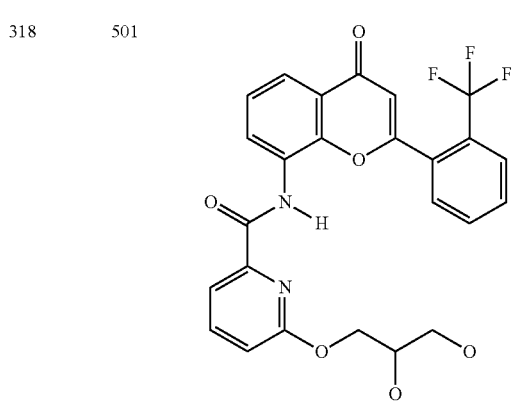 |
188
-continued
| Compd No | [M + H]+ | Structure |
|---|---|---|
| 319 | 463 | 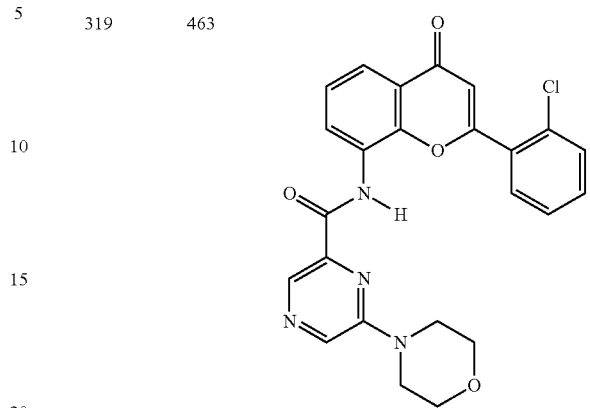 |
| 320 | 494 | 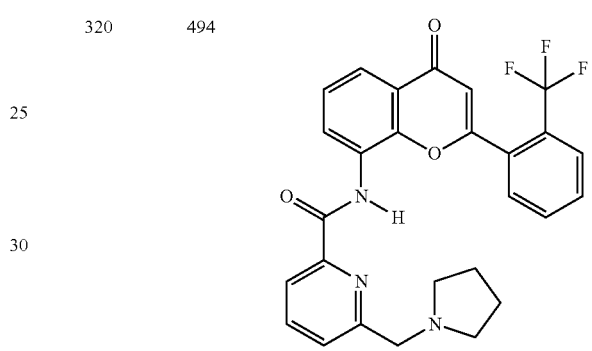 |
| 322 | 496 | 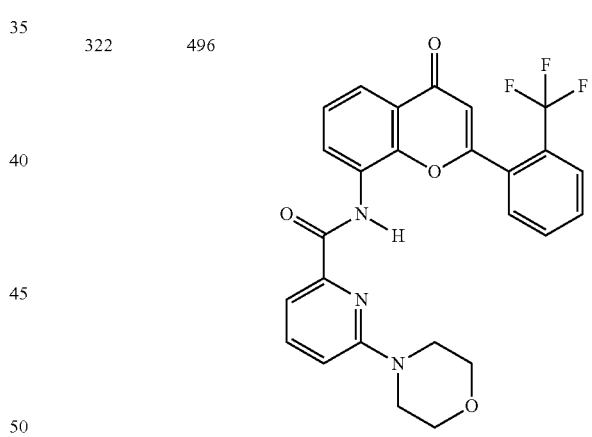 |
| 323 | 480 | 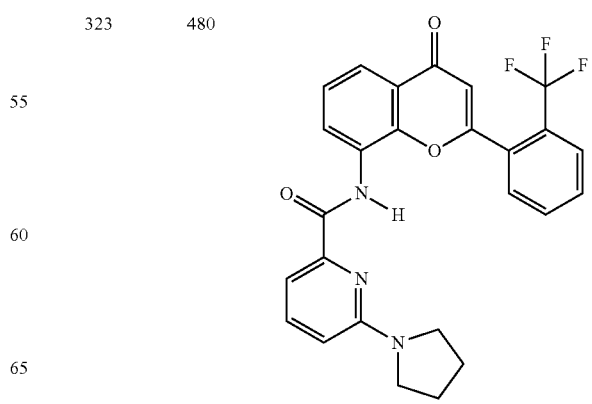 |

-continued
| Compd No | [M + H]+ | Structure |
|---|---|---|
| 324 | 462 | 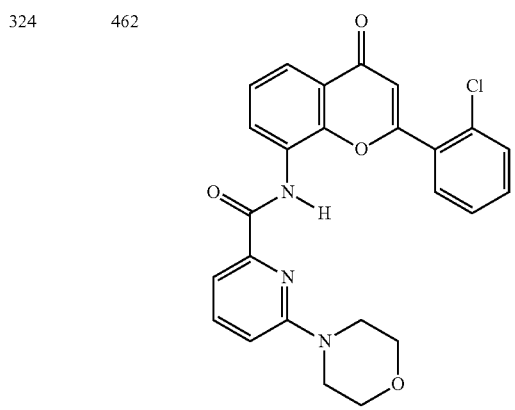 |
| 325 | 446 | 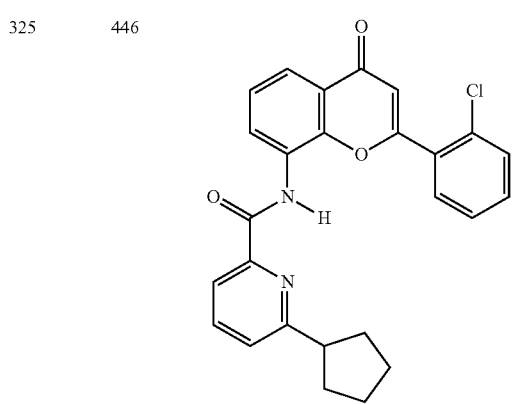 |
| 327 | 460 | 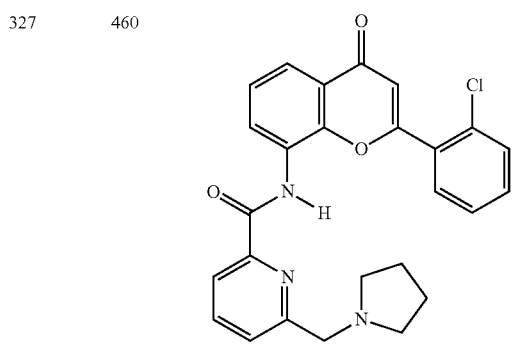 |
| 329 | 445 | 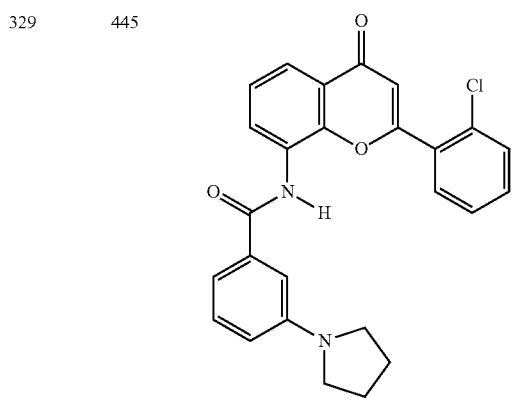 |
-continued
| Compd No | [M + H]+ | Structure |
|---|---|---|
| 331 | 476 | 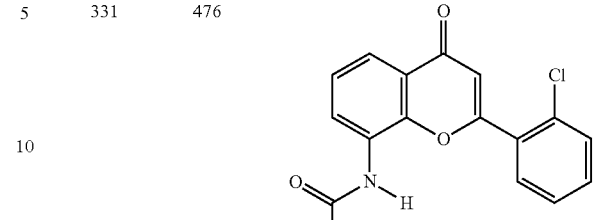 |
| 334 | 467 | 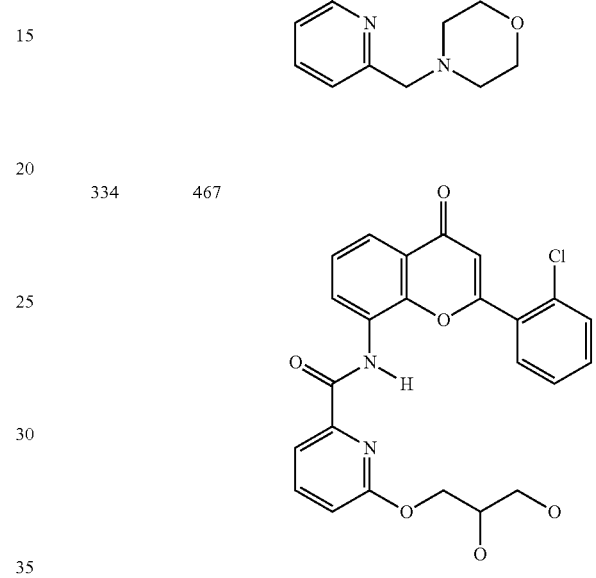 |
| 335 | 378 | 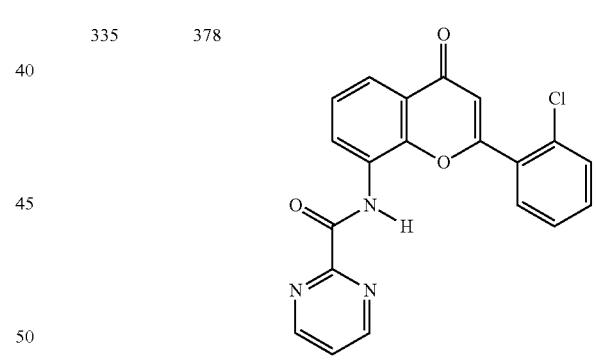 |
| 337 | 380 | 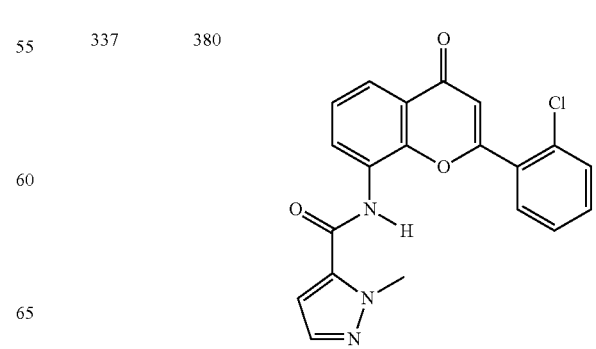 |

191
-continued
| Compd No | [M + H]+ | Structure |
|---|---|---|
| 338 | 483 | 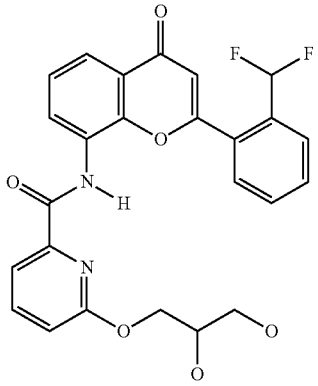 [SMILES: O=C(Nc1cccc2c(=O)cc(-c3ccccc3C(F)F)oc12)c1cccc(OCC(O)CO)n1] |
| 339 | 492 | 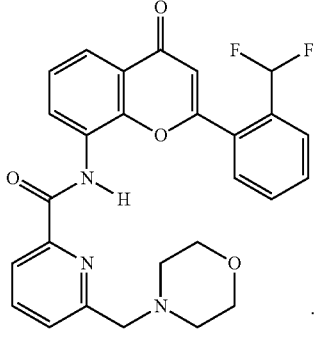 [SMILES: O=C(Nc1cccc2c(=O)cc(-c3ccccc3C(F)F)oc12)c1cccc(CN2CCOCC2)n1] |
3. The compound of claim 2 which is selected from:
| Compd No | [M + H]+ | Structure |
|---|---|---|
| 227 | 417 | 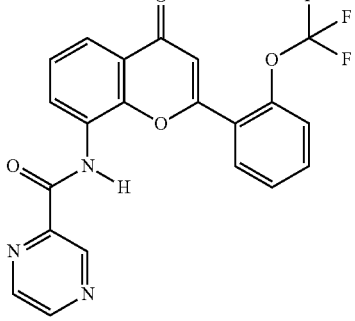 |
| 231 | 428 | 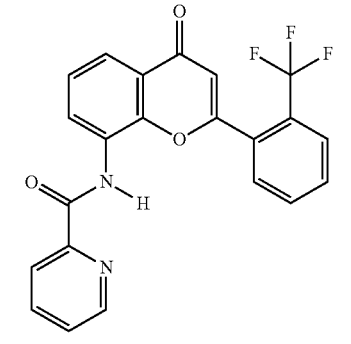 |
192
-continued
| Compd No | [M + H]+ | Structure |
|---|---|---|
| 234 | 428 | 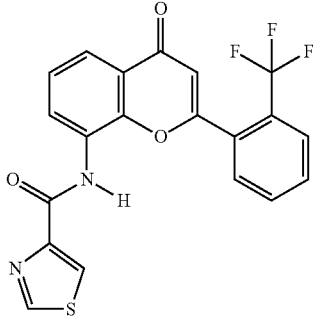 [SMILES: O=C(Nc1cccc2c(=O)cc(-c3ccccc3C(F)(F)F)oc12)c1cscn1] |
| 251 | 411 | 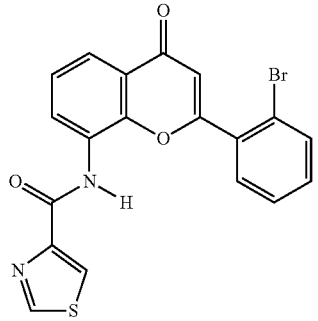 [SMILES: O=C(Nc1cccc2c(=O)cc(-c3ccccc3Br)oc12)c1cscn1] |
| 252 | 412 | 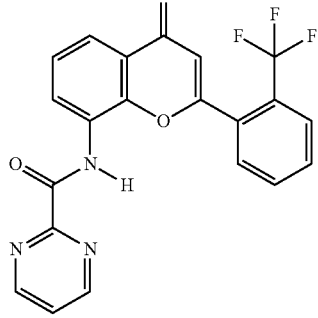 |
| 253 | 412 | 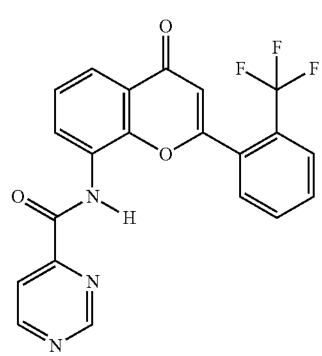 [SMILES: O=C(Nc1cccc2c(=O)cc(-c3ccccc3C(F)(F)F)oc12)c1ccncn1] |

| Compd No | [M + H]+ | Structure |
|---|---|---|
| 261 | 412 | 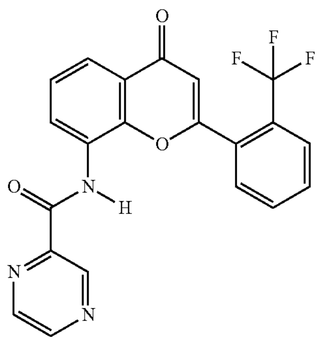 [SMILES: O=C(Nc1cccc2c(=O)cc(-c3ccccc3C(F)(F)F)oc12)c1cnccn1] |
| 280 | 378 | 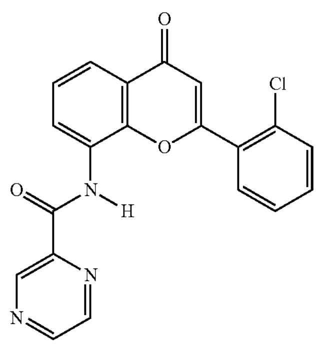 [SMILES: O=C(Nc1cccc2c(=O)cc(-c3ccccc3Cl)oc12)c1cnccn1] |
| 296 | 396 | 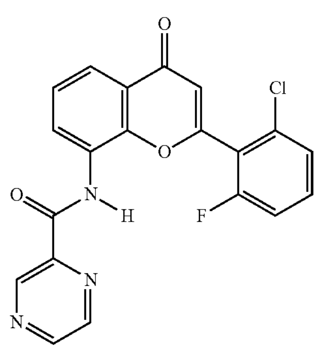 [SMILES: O=C(Nc1cccc2c(=O)cc(-c3c(F)cccc3Cl)oc12)c1cnccn1] |

| Compd No | [M + H]+ | Structure |
|---|---|---|
| 315 | 510 | 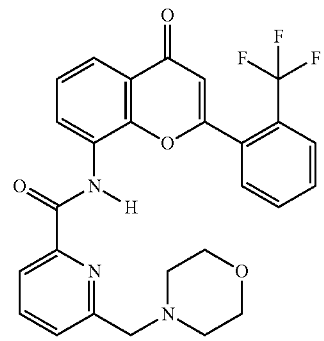 [SMILES: O=C(Nc1cccc2c(=O)cc(-c3ccccc3C(F)(F)F)oc12)c1cccc(CN2CCOCC2)n1] |
| 323 | 480 | 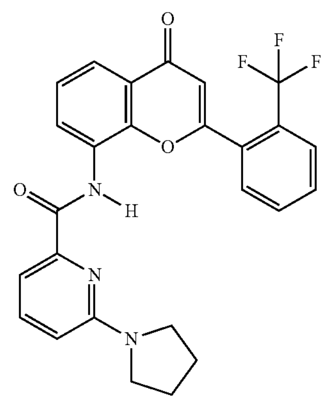 [SMILES: O=C(Nc1cccc2c(=O)cc(-c3ccccc3C(F)(F)F)oc12)c1cccc(N2CCCC2)n1] |
| 337 | 380 | 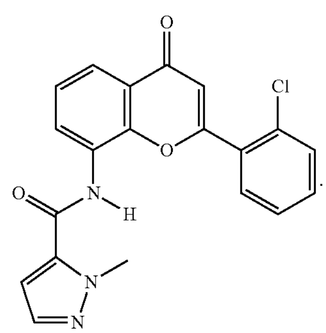 [SMILES: Cn1nccc1C(=O)Nc1cccc2c(=O)cc(-c3ccccc3Cl)oc12] |

4. A pharmaceutical composition comprising a pharmaceutically acceptable carrier or diluent; and a compound according to claim 1 or a pharmaceutical salt thereof.

* * * * *